US006221914B1

(12) United States Patent
Burgess et al.

(10) Patent No.: US 6,221,914 B1
(45) Date of Patent: Apr. 24, 2001

(54) SULFONAMIDE BRIDGING COMPOUNDS THAT INHIBIT TRYPTASE ACTIVITY

(75) Inventors: Laurence E. Burgess, Boulder; James P. Rizzi, Niwot, both of CO (US)

(73) Assignee: Array Biopharma Inc., Boulder, CO (US)

( * ) Notice: Subject to any disclaimer, the term of this patent is extended or adjusted under 35 U.S.C. 154(b) by 0 days.

(21) Appl. No.: 09/179,781

(22) Filed: Oct. 27, 1998

Related U.S. Application Data

(60) Provisional application No. 60/065,026, filed on Nov. 10, 1997.

(51) Int. Cl.[7] ........................... A61K 31/18; C07D 311/18
(52) U.S. Cl. ........................... 514/603; 514/602; 514/604; 564/80; 564/82; 564/84; 564/85; 564/86; 564/87; 564/88; 564/89; 564/90; 564/92; 564/93; 564/94
(58) Field of Search ..................................... 514/602, 603, 514/604; 564/80, 84, 85, 86, 87, 88, 89, 90, 92, 93, 94, 82

(56) References Cited

U.S. PATENT DOCUMENTS

| | | | |
|---|---|---|---|
| 2,773,765 | * 12/1956 | Sus et al. | 430/270.1 |
| 3,282,208 | * 11/1966 | Ruderman et al. | 101/456 |
| 3,883,653 | 5/1975 | Barth | 424/251 |
| 4,954,519 | 9/1990 | Powers et al. | 514/456 |
| 5,391,705 | 2/1995 | Neises et al. | 530/331 |
| 5,498,779 | 3/1996 | Neises et al. | 514/428 |
| 5,525,623 | 6/1996 | Spear et al. | 514/423 |
| 5,612,378 | * 3/1997 | Tianbao et al. | 514/602 |
| 5,656,660 | 8/1997 | Lum et al. | 514/467 |

FOREIGN PATENT DOCUMENTS

| | | |
|---|---|---|
| 0 503 674 A1 | 9/1962 | (EP) . |
| 0 504 064 A1 | 9/1992 | (EP) . |
| 0 696 585 A1 | 2/1996 | (EP) . |
| 1 288 376 | 9/1972 | (GB) . |
| 1 288 377 | 9/1972 | (GB) . |
| WO 94/20527 | 9/1994 | (WO) . |
| WO 94/27958 | 12/1994 | (WO) . |
| WO 95/32945 | 12/1995 | (WO) . |
| WO 96/09297 | 3/1996 | (WO) . |
| WO 98/01428 | 1/1998 | (WO) . |
| WO 98/04537 | 2/1998 | (WO) . |
| WO 98/45275 | 10/1998 | (WO) . |
| WO 99/12918 | 3/1999 | (WO) . |
| WO 99/12935 | 3/1999 | (WO) . |
| WO 99/26925 | 6/1999 | (WO) . |

OTHER PUBLICATIONS

Synthesis of some p,p'-bis(methyltosylamino)-m, m'-dimethyldiphenylmethanes, K.P. Agarwal and B. Paul, Chem. Abs., 55, 27206f. (Citing J. Sci. Ind. Research (India) 20C, pp147–50 (1961).)*

Alter, S.C., et al., Interactions of Human Mast Cell Tryptase with Biological Protease Inhibitors, *Arch. Biochem. Biophys.*, 276:26–31 (1990).
Burgess, L.E., et al., Potent Selective Nonpeptidic Inhibitors of Human Lung Tryptase, *Proc. Natl. Acad. Sci. USA* 96: 8348–8352 (1999).
Caughey, G.H., et al., Bis(5–amidino–2–benzimidazolyl)methane and Related Amidines are Potent, Reversible Inhibitors of Mast Cell Tryptases, *J. Pharmacol. Exp. Ther.*, 264: 676–682 (1993).
Chen, H., et al., Design of the First Highly Potent and Selective Aminopeptidase N (E.C. 3.4.11.2) Inhibitor, *Bioorg. Med. Chem. Lett.*, 9: 1511–1516 (1999).
Clark, J.M., et al., Tryptase Inhibitors Block Allergen–induced Airway and Inflammatory Responses in Allergic Sheep, *Am. J. Respir. Crit. Care Med.*, 152: 2076–2083 (1995).
Clark, J.M., et al., Tryptase Inhibitors: A New Class of Antiinflammatory Drugs, *Drugs of the Future* 21: 811–816 (1996).
Combrink, K.D., et al., 1,2–Benzisothiazol–3–one 1,1–Dioxide Inhibitors of Human Mast Cell Tryptase, *J. Med. Chem.* 41: 4854–4860 (1998).
Cregar, L., et al., Neutrophil Myeloperoxidase is a Potent and Selective Inhibitor of Mast Cell Tryptase, *Arch. Biochem. Biophys.*, 366: 125–130 (1999).
Elrod, K.C., et al., Lactoferrin, a Potent Tryptase Inhibitor, Abolishes Late–Phase Airway Responses in Allergic Sheep, *Am. J. Respir. Crit. Care Med.*, 156: 375–381 (1997).
He, S., et al., A Role for Tryptase in the Activation of Human Mast Cells: Modulation of Histamine Release by Tryptase and Inhibitors of Tryptase, *J. Pharmacol. Exper. Ther.*, 286: 289–297 (1998).
Katz, B.A., et al., Design of Potent Selective Zinc–Mediated Serine Protease Inhibitors, *Nature* 391: 608–612 (1998).
Nadel, J.A., Roles of Mast Cell Proteases in Airways, *Drugs*, 37: 51–55 (1989).
Schwartz, L.B., Tryptase, a Mediator of Human Mast Cells, *J. Allergy Clin. Immunol.*, 86: 594–598 (1990).
Stürzbecher, J., et al., Inhibition of Human Mast Cell Tryptase by Benzamidine Derivatives, *Biol. Chem. Hoppe–Seyler*, 373: 1025–1030 (1992).
Tidwell. R.R., et al., Diarylamidine Derivatives with One or Both of the Aryl Moieties Consisting of an Indole or Indole–like Ring. Inhibitors of Arginine–Specific Esteroproteases, *J. Med. Chem.*, 21: 613–623 (1978).

* cited by examiner

*Primary Examiner*—Laura L. Stockton
(74) *Attorney, Agent, or Firm*—McDonnel Boehnen Hulbert & Berghoff

(57) ABSTRACT

The present invention is directed to compounds which are capable of inhibiting the activity of tryptase. Such compounds are useful in the treatment or prevention of inflammatory disease, particularly those disease states which are mediated by mast cell activation. Also encompassed by the invention are formulations comprising the noted compounds, processes for preparing such compounds and methods for treating or preventing an inflammatory disease.

47 Claims, No Drawings

SULFONAMIDE BRIDGING COMPOUNDS THAT INHIBIT TRYPTASE ACTIVITY

This application claims the benefit of U.S. Provisional Application Ser. No. 60/065,026, filed Nov. 10, 1997, which is hereby incorporated by reference.

FIELD OF THE INVENTION

This invention relates to antiinflammatory and antiallergy agents and, more particularly, relates to novel compounds, formulations and methods for the prophylaxis and treatment of inflammation, allergy and pulmonary disorders. The invention particularly relates to compositions and methods that are efficacious for the treatment of tryptase-related and mast cell mediated inflammatory disorders.

BACKGROUND OF THE INVENTION

The disorders noted above include, among others, asthma and other inflammatory diseases of the pulmonary system like allergic rhinitis, chronic obstructive pulmonary disease, respiratory syncytial virus and smoker's emphysema where the methods and compositions described herein are useful. Furthermore, the compositions and methods are particularly useful in treating the underlying pathological changes in the airways associated with these diseases such as basement membrane thickening, cell hypertrophy and hyperplasia, inflammatory cell influx, and other tissue remodeling. Other inflammatory conditions, including, for example, rheumatoid arthritis, multiple sclerosis, inflammatory bowel disease, conjunctivitis, psoriasis, scleroderma, and related diseases can be treated with the compounds and methods described herein.

To better understand the invention, the following brief description of mast cell mediated disease, particularly asthma, is provided. Human asthma is a complex inflammatory disease. Genetic susceptibility and repeated allergen exposure from a variety of sources lead to allergen sensitization that, via IL-4 production from T-cells and mast cells, can ultimately induce B-cell derived IgE levels that are significantly elevated over normal levels. Subsequent exposure to allergen coupled with these newly elevated IgE levels can activate the FcERI high affinity IgE receptor on the surface of mast cells and other pro-inflammatory cells in the lung to induce degranulation/activation and thus trigger a cascade of inflammatory responses. This early phase of the response is characterized by severe bronchoconstriction that reaches its peak at about 15 minutes followed by a recovery of several hours. Many pre-formed substances are immediately released from the mast cell including histamine, heparin, cytokines (including, for example, IL-3, IL-4, IL-5, IL-6, and TNF-α), and proteases (including, for example, cathepsin G, chymase, carboxy peptidase A, tryptase). In relation to these other proteases, tryptase is released in very large amounts up to 35 pg per cell (see Caughey, *Am. J. Physiol.*, 257, L39–46 (1989) and Walls in "Asthma and Rhinitis" 1995, pp. 801–824). Furthermore, tryptase is long lived, and has been shown to have a myriad of significant effects as a peptidase, protease and cytokine that intensify the inflammatory response. For example, tryptase can cause further mast cell degranulation to amplify the allergen response (see Molinari et al., *J. Appl. Physiol.*, 79(6), 1966–70 (1995)) and induce eosinophil and neutrophil migration into the lung (see Walls et al., *Int. Arch. Allergy Immunol.*, 107, 372–3 (1995)). Also, tryptase can inactivate fibrinogen to act as a local anti-coagulant and promotes plasma extravasation bringing more circulating cells and mediators into the lung (see Schwartz et al, *J. Immunol.*, 135, 2762–7 (1985)). Further, tryptase can process high and low molecular weight kininogen to bradykinin and activates kallikrein to produce neurogenic inflammation (see Proud et al., *Biochem. Pharm.*, 37(8), 1473–80 (1988); Walls et al., *Biochem. Soc. Trans.*, 20, 260S (1992); Imamura et al., *Lab. Invest.*, 74, 861–70 (1996)) while degrading neurogenic feedback mechanisms like the bronchodilatory neuropeptides (for example, VIP, peptide histidine methionine and peptide histidine isoleucine) and further promote mucous secretion and bronchoconstriction (see Tam and Caughey, *Am. J. Respir. Cell Mol. Biol.* 3, 27–32 (1990)). Tryptase can amplify the effects of histamine to further enhance bronchoconstriction (see Molinari et al., *J. Appl. Physiol.*, 79(6), 1966–70 (1995); Sekizawa et al, *J. Clin. Invest.*, 83, 175–9 (1989); Johnson et al., Eur. Respir. J., 10, 38–43 (1997)). Tryptase is a mitogen/activator of fibroblast (see Ruoss et al., *J. Clin. Invest.*, 88, 493–9 (1991); Gruber et al., *J. Immunology*, 158, 2310–17 (1997)) and bronchial smooth muscle cells which can contribute to airway hyperresponsiveness to the lung as seen in a variety of pulmonary disorders (see Brown et al., *Chest*, 107(3), 95–6S (1995); Caughey et al., *Am. J. Respir. Cell Mol. Biol.*, 13, 227–36 (1995)). Further, tryptase is a mitogen for airway epithelial cells and induces IL-8 and ICAM-1 expression (see Cairns and Walls *J. Immunology*, 156, 275–83 (1996)) and recently tryptase has been shown to activate cellular receptors (see Molino et al., *J. Biol. Chem.*, 272(7), 4043–49 (1997)).

Following this early mast cell degranulation and release of tryptase, the activation of the arachidonic acid cascade resulting in the production of lipid mediators, such as the leukotrienes (LTD4, LTC4, LTE4, LTB4), the prostaglandins (PGD2) and platelet activating factor (PAF), occurs several minutes later. Six to twelve hours after initial allergen exposure, a late phase inflammatory response takes place in which bronchoconstriction is again visited upon the asthmatic. By this time the mast cell has begun to produce protein mediators like the cytokines (IL-1,3,4,5,6), chemokines (IL-8, MIP-1a) and growth factors (GM-CSF). This late phase response is associated with a significant influx of inflammatory cells, most notably eosinophils, neutrophils, and lymphocytes, into the lung tissue and airway space. These cells are activated and release even more mediators which can contribute to the significant tissue damage and development of hyperresponsiveness seen in chronic asthma.

The various activities of tryptase contribute to the early and late phase bronchoconstriction as well as to the development of airway hyperresponsiveness, a hallmark of asthma. Furthermore, in chronic asthma and other long term respiratory diseases, these activities cause profound changes to the airway such as desquamation of the epithelial lining, fibrosis and thickening of the underlying tissues. These changes are not treated by present therapeutics.

Tryptase can be detected in a variety of biological fluids and recently tryptase's relatively long biological half-life (vis a vis histamine) has become appreciated and clinicians now use circulating levels of tryptase as a marker of anaphylaxis (see Schwartz et al., *N. Engl. T. Med.*, 316, 1622–26 (1987)). Elevated levels of tryptase can be detected in lavage fluid from allergen challenged atopic asthmatics as well as in cigarette smokers, where there is significant lung damage (see Castells et al., *J. Allerg. Clin. Immunol.*, 82, 348–55 (1988); Wenzel et al., *Am. Rev. Resp. Dis.*, 141 563–8 (1988); Kalenderian et al., *Chest*, 94, 119–23 (1988)).

Tryptase can process prostromelysin to mature stromelysin (MMP-3) which can further activate collagenase (MM- 1). Thus tryptase could play a significant role in the tissue remodeling of various pulmonary disorders (most notably asthma) but also in rheumatoid and osteo-arthritis.

Tryptase is stored in the mature form as a homotetramer within the secretory granules of the mast cell and probably is held in an inactivated form by the low pH of this intracellular media. When released it is stabilized by interactions with heparin. This unique assembly of 4 catalytically active subunits could also be considered to be a dimer of dimers because computational models indicate that two adjacent active sites may face one another.

Being a member of the tryptic-like serine protease family, human tryptase prefers an arginine or lysine in the P1 subsite of a substrate. Because of this well recognized preference for basic residues at S1 there have been reports of inhibitors that incorporate physiologically protonated basic chemical moieties. (See, for example, benzamidines (see Caughey et al., J. Pharm. Exp. Therap., 264, 676–82 (1993); Tidwell, et al., J. Med. Chem. 21(7), 613 (1978); Dominguez et al., WO 9801428 and references cited therein)); benzguanidines, benzylamines (see Rice et al., WO 9609297); and, modified peptides incorporating an arginine (see Spear et al., WO 9420527)). (See also Lum, e a., WO 95/32945 (based on U.S. Ser. No. 08/252,099, filed Jun. 1, 1994, now issued as U.S. Pat. No. 5,656,660 (granted Aug. 12, 1997)); Neises et al., U.S. Pat. No. 5,391,705 (granted Feb. 21, 1995); Neises et al., U.S. Pat. No. 5,498,779 (granted Mar. 12, 1996); Neises et al. EP A 0504064 (published Sep. 16, 1992); Powers et Al., U.S. Pat. No. 4,954,519 (granted Sep. 4, 1990); Von der Saal et Al., Wo 94/27958 (published Dec. 8, 1994) and Spear et al., U.S. Pat. No. 5,525,623 (granted Jun. 11, 1996)).

SUMMARY OF THE INVENTION

As noted, the present invention provides novel compounds which inhibit tryptase activity. Also provided are formulations containing the novel compounds and methods of using the compounds to treat a patient in need thereof. More specifically, there are provided methods for the treatment of a patient suffering from a mast cell mediated disorder, including for example, asthma, allergic rhinitis, rheumatoid arthritis, dermatological diseases, multiple sclerosis, conjunctivitis, inflammatory bowel disease, anaphylaxis, osteoarthritis, peptic ulcers, cardiovascular disease, or other disease state in which mast cells and, in particular, tryptase activation is involved. In addition, there are described processes for preparing the inhibitory compounds of the invention.

The present invention relates to tryptase inhibitors, pharmaceutically acceptable salts and prodrugs thereof useful in the treatment or prophylaxis of inflammatory diseases, particularly asthma and other related inflammatory diseases. The especially preferred compounds of the invention are characterized as bisaryl benzamidine sulfonamides and amides. The invention also encompasses pharmaceutical compositions and methods for prophylaxis and treatment of asthma, pulmonary disorders and related inflammatory, mast-cell mediated diseases, particularly those which involve activation of tryptase. Also provided are processes for making such compounds as well as intermediates useful in such processes.

DETAILED DESCRIPTION OF THE INVENTION

As noted, the present invention provides compounds useful for the treatment or prophylaxis of inflammatory diseases. In particular, a compound of formula (I):

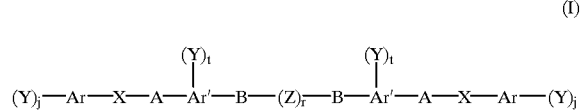

(I)

wherein

Ar or Ar' is aryl, heteroaryl, or a 5-membered to 7-membered carbocyclic or heterocyclic ring;

A is $-[(CH_2)_m-C(O)]_r-NR^2-(CH_2)_m-$ or $-[(CH_2)_m-C(O)]_r-NR^2-(CH(COOH))-$;

B is $-[(D)_r-(CH_2)_m]-$, or $-(CH_2)_m-$, provided that if B is $-[(D)_r-(CH_2)_m]-$, m in $-[(D)_r-(CH_2)_m]-$ is not zero;

D is $-O-$, $-S-$, $-SO_2-$, $-C(O)-$ or $-NH-$;

X is $-C(O)-$, $-(CH_2)_m-$ or $-SO_2-$;

Y is $R^1HN-C(=NH)-$, $R^1HN-CO-NH-$, $N\equiv C-$ or $R^1HN-(CH_2)_v-$, $CH_3SO_2NH-(CH_2)_v-$, $-OH$, $-SH$, $-CF_3$, $-F$, $-Cl$, $-Br$, $-I$, $-H$, $-O(C_1-C_4)$alkyl, aryl, heteroaryl, $(C_1-C_4)$acyloxy, $(C_1-C_4)$alkyl, $(C_1-C_4)$alkylthio, $-NO_2$;

Z is $-(CH_2)_m-$, $-O-$, $-S-$, $-SO_2-$, $-NH-$, $-(CH_2)_v-C=C-(CH_2)_v-$, $-(CH_2)_v-C\equiv C-(CH_2)_v-$, $-C(O)-$, or

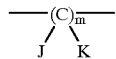

in which J and K, independently, are $-H$, $-(C_1-C_6)$alkyl—COOH, $-(C_1-C_4)$alkyl, a $-(C_3-C_6)$ carbocyclic ring wherein the $-(C_3-C_6)$carbocyclic ring optionally is substituted with one or more —COOH or $-O(C_1-C_4)$alkyl groups, or J and K, when taken together with the carbon to which they are attached, form a 3-membered to 8-membered carbocyclic or heterocyclic ring;

$R^1$ is $-H$, $(C_1-C_4)$alkyl—O—CO—, $(C_1-C_4)$alkyl—O— or HO—;

$R^2$ is $-H$ or $-(C_1-C_4)$ alkyl;

j is an integer from 1 to 5, inclusive;

m is an integer between 0 and 10, inclusive;

r is 0 or 1;

t is an integer from 1 to 5, inclusive;

v is an integer between 0 and 6, inclusive;

wherein which each Y, Ar, Ar', X, A, B, j, m, r, t or v is the same or different, provided that if Ar is benzofuran, then r is not zero and X is not $-(CH_2)_m-$; or, a pharmaceutically acceptable salt, ester, or solvate thereof, is useful for the treatment or prophylaxis of an inflammatory disease, particularly a mast-cell mediated inflammatory disease, especially one in which tryptase is activated.

Preferred compounds of Formula (I) are those in which Ar and Ar' are phenyl and in which each Y is $R^1HN-C(=NH)-$. Especially preferred are those compounds of Formula (I) in which each X is $-SO_2-$ or $-C(O)-$. An especially preferred embodiment of the invention include those compounds in which each X is $-C(O)-$.

Thus, a compound of Formula (I) represented by Formula (Ie):

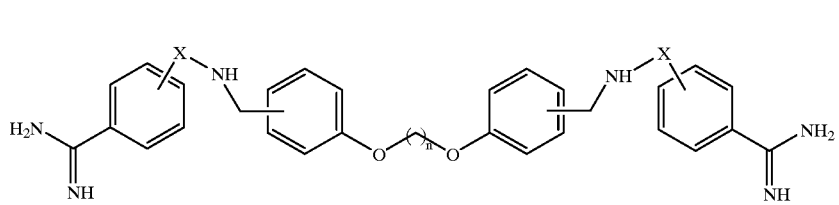

(Ie)

wherein X is —SO$_2$— or —C(O)—, particularly —C(O)—, is a most preferred embodiment of the invention.

The term "alkyl" refers to a univalent saturated, straight- or branched-chain alkyl group containing the designated number of carbon atoms. Thus, the term "C$_1$–C$_6$ alkyl" refers to a univalent saturated, straight—or branched-chain alkyl group which can contain from one to six carbon atoms, for example, methyl, ethyl, n-propyl, isopropyl, n-butyl, sec-butyl, t-butyl, n-pentyl, 2-methylbutyl, 3-methyl-butyl, n-hexyl, 2-methylpentyl, 3-methylpentyl, 4-methylpentyl, 2,2-dimethylbutyl, 2,3-dimethylbutyl, and the like.

The term alkoxy refers to an alkyl group bonded through an oxygen atom to another substituent. Thus, the term "C$_1$–C$_4$ alkoxy" refers to a C$_1$–C$_4$ alkyl group bonded through an oxygen atom to another substituent and includes, for example, methoxy, ethoxy, n-propoxy, n-butoxy, t-butoxy and isobutoxy.

The term "carbocyclic" refers to an organic cyclic moiety in which the cyclic skeleton is comprised of only carbon atoms whereas the term "heterocyclic" refers to an organic cyclic moiety in which the cyclic skeleton contains one or more heteroatoms selected from nitrogen, oxygen, or sulfur and which may or may not include carbon atoms.

Thus, the term "cycloalkyl" refers to a carbocyclic moiety containing the indicated number of carbon atoms. The term "C$_3$–C$_6$ cycloalkyl", therefore, refers to an organic cyclic substituent in which three to six carbon atoms form a three, four, five, or six-membered ring, including, for example, a cyclopropyl, cyclobutyl, cyclopentyl, or cyclohexyl ring.

"Aryl" refers to an aromatic carbocyclic group having a single ring, for example, a phenyl ring, multiple rings, for example, biphenyl, or multiple condensed rings in which at least one ring is aromatic, for example, naphthyl, 1,2,3,4,-tetrahydronaphthyl, anthryl, or phenanthryl, which can be unsubstituted or substituted with one or more substituents selected from halogen, lower (C$_1$–C$_4$) alkyl, lower (C$_1$–C$_4$) alkoxy, lower (C$_1$–C$_4$) alkylthio, trifluoromethyl, lower (C$_1$–C$_4$) acyloxy, aryl, heteroaryl and hydroxy. The substituents attached to a phenyl ring portion of an aryl moiety (i.e. either or both of Ar or Ar') in the compounds of Formula (I) may be configured in the ortho-, meta- or para- orientations, with the meta- and para- orientations being preferred.

Examples of typical aryl moieties included in the scope of the present invention may include, but are not limited to, the following:

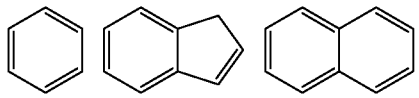

-continued

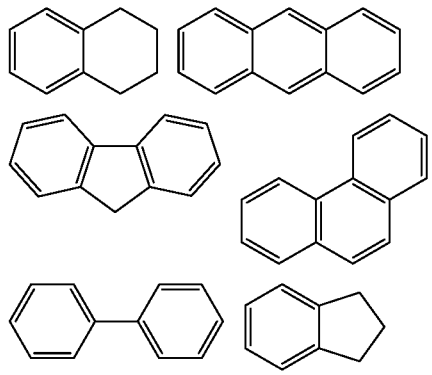

"Heterocycle" or "heterocyclic" refers to a saturated, unsaturated or aromatic carbocyclic group having a single ring, multiple rings or multiple condensed rings, and having at least one hetero atom such as nitrogen, oxygen or sulfur within at least one of the rings. "Heteroaryl" refers to a heterocycle in which at least one ring is aromatic. Any of the heterocyclic or heteroaryl groups can be unsubstituted or optionally substituted with one or more groups selected from halogen, lower (C$_1$–C$_4$) alkyl, lower (C$_1$–C$_4$) alkoxy, lower (C$_1$–C$_4$) alkylthio, trifluoromethyl, lower (C$_1$–C$_4$) acyloxy, and hydroxy.

As one skilled in the art will appreciate such heterocyclic moieties may exist in several isomeric forms, all of which are to be encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

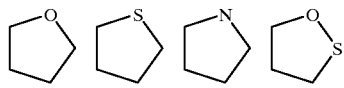

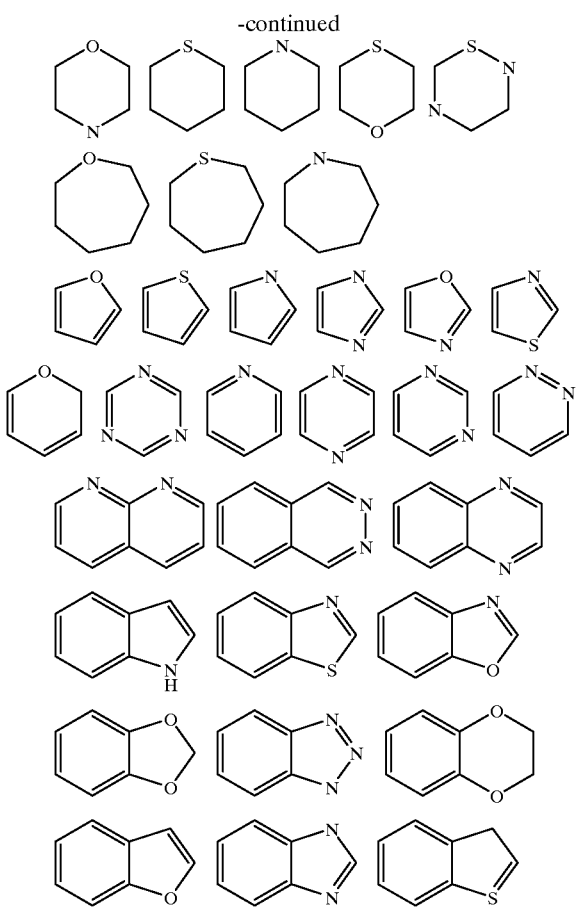

The term "halo" refers to a halogen atom which may include fluoro, chloro, bromo and iodo. Preferred halo groups include chloro, bromo and fluoro with chloro and fluoro being especially preferred.

"Pharmaceutically acceptable salt", as used herein, refers to an organic or inorganic salt which is useful in the treatment of a warm-blooded animal. Such salts can be acid or basic addition salts, depending on the nature of the compound of Formula (I). As used herein, "warm blooded animal" includes a mammal, including a member of the human, equine, porcine, bovine, murine, canine or feline species.

In the case of an acidic moiety in a compound of Formula (I), a salt may be formed by treatment of a compound of Formula (I) with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of Formula (I).

With respect to basic moieties, a salt is formed by the treatment of a compound of Formula (I) with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, paratoluenesulfonic, sorbic, puric, benzoic, cinnamic and the like organic acids. An especially preferred salt of this type is a hydrochloride or sulfate salt of a compound of Formula (I).

Also encompassed in the scope of the present invention are pharmaceutically acceptable esters of a carboxylic acid or hydroxyl containing group, including a metabolically labile ester or a prodrug form of a compound of Formula (I). A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. Esters of a compound of Formula (I), may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$–$C_4$)alkyloxy)ethyl; for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$–$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Additionally, the compounds of the instant invention may have one or more asymmetrical carbon atoms and, therefore, may exist in stereoisomeric forms. All stereoisomers are intended to be included within the scope of the present invention. As used, "stereoisomer" or "stereoisomeric" refers to a compound which has the same molecular weight, chemical composition, and constitution as another, but with the atoms grouped such that their orientation in three-dimensional space is different. Such stereoisomers may exist as enantiomeric mixtures, diastereomers or may be resolved into individual stereoisomeric components e.g. specific enantiomers) by methods familiar to one skilled in the art.

Likewise, the compounds of Formula (I) may exist as isomers, that is compounds of the same molecular formula but in which the atoms, relative to one another, are arranged differently. In particular, the bridging portions of the compounds of Formula (I), including for example the portions of the molecule defined by A, B and, or Z are normally and preferably arranged as indicated in the definitions for each of these groups, being read from left to right. However, in certain cases, one skilled in the art will appreciate that it will possible to prepare compounds of Formula (I) in which these substituents are reversed in orientation relative to the other atoms in the molecule. That is, the definitions of any of these substituents may be read from right to left. One skilled in the art will appreciated that these isomeric forms of the compounds of Formula (I) are to be construed as encompassed within the scope of the present invention.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

In another aspect, the compounds of the invention are useful for the therapeutic or prophylactic treatment of an inflammatory disease state in warm-blooded animals. For example, as noted, the compounds of the invention may be used as anti-inflammatory agents in an inflammatory disease, especially a mast-cell mediated disease, for example, asthma, allergy or pulmonary disorders.

While it may be possible to administer a compound of the invention alone, normally it will be present as an active ingredient in a pharmaceutical formulation. Thus, in one another embodiment of the invention, there is provided a formulation comprising a compound of Formula (I) in combination, admixture, or associated with a pharmaceutically acceptable carrier, diluent or excipient therefor.

The composition used in the noted therapeutic methods can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Considerations for preparing appropriate formulations will be familiar to one skilled in the art and are described, for example, in Goodman and Gilman's: "The Pharmacological Basis of Therapeutics", 8th Ed., Pergamon Press, Gilman et al. eds. (1990); and "Remington's Pharmaceutical Sciences", 18th Ed., Mack Publishing Co., A. Gennaro, ed. (1990). Methods for administration are discussed therein, eg. for oral, topical, intravenous, intraperitoneal, or intramuscular administration. Pharmaceutically acceptable carriers, diluents, and excipients, likewise, are discussed therein. Typical carriers, diluents, and excipients may include water (for example, water for injection), buffers, lactose, starch, sucrose, and the like.

As noted, a compound of the invention can be administered orally, topically or parenterally (e.g. intravenously, intraperitoneally, intramuscularly, subcutaneously, etc.), or inhaled as a dry powder, aerosol, or mist, for pulmonary delivery, for example, in the treatment or prophylaxis of asthma. Such forms of the compounds of the invention may be administered by conventional means for creating aerosols or administering dry powder medications using devices such as for example, metered dose inhalers, nasal sprayers, dry powder inhaler, jet nebulizers, or ultrasonic nebulizers. Such devices optionally may be include a mouthpiece fitted around an orifice. In certain circumstances, it may be desirable to administer the desired compound of the invention by continuous infusion, such as through a continuous infusion pump, or using a transdermal delivery device, such as a patch.

Typically, when the compounds of the invention are to be used in the treatment of asthma or allergic rhinitis, they will be formulated as aerosols. The term "aerosol" includes any gas-borne suspended phase of a compound of the invention which is capable of being inhaled into the bronchioles or nasal passages. Specifically, aerosol includes a gas-borne suspension of droplets of the desired compound, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

For solutions used in making aerosols of the invention, the preferred range of concentration of the compounds of the invention is 0.1–100 milligrams (mg)/milliliter (mL), more preferably 0.1–30 mg/mL, and most preferably 1–10 mg/mL. Usually the solutions are buffered with a physiologically compatible buffer such as phosphate or bicarbonate. The usual pH range is from about 5 to about 9, preferably from about 6.5 to bout 7.8, and more preferably from about 7.0 to about 7.6. Typically, sodium chloride is added to adjust the osmolarity to the physiological range, preferably within 10% of isotonic. Formulation of such solutions for creating aerosol inhalants is discussed, for example, in Remington's, supra; See, also, Ganderton and Johens, "Drug Delivery to the Respiratory Tract, Ellis Horwood (1987); Gonda, "Critical Review in Therapeutic Drug Carrier Systems" 6 273–313 (1990); and Raeburn et al. J. Pharmacol. Toxicol. Methods. 27 143–159 (1992).

Solutions of a compound of the invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the invention connected to or contained within any of the conventional means for creating aerosols in asthma medication, such as metered dose inhalers, jet nebulizers, or ultrasonic nebulizers. Optionally such devices may include a mouthpiece fitted around the orifice.

In the treatment of allergic rhinitis, a device may comprise a solution of a compound of the instant invention in a nasal sprayer.

A dry powder comprising a compound of the invention, optionally with an excipient is another embodiment. This may be administered by a drug powder inhaler containing the described powder.

One skilled in the art will appreciate that the methods of the invention can be used in combination with other agents for the treatment of mast cell mediated inflammatory disorders, and particularly, asthma. β-Adrenergic agonists are especially useful in these combinations, because they provide symptomatic relief of the initial asthmatic response, whereas the compounds of the present invention may provide relief and be better suited to treating the late asthmatic response. Preferred β-adrenergic agonists in these solutions include any of the usual β-agonists employed for the relief of asthma, for example, albuterol, terbutaline, bitolterol mesylate, or the like.

Other agents useful in combination with the compounds of the invention include anticholinergics, such as ipratropium bromide, and antiinflammatory corticosteroids (adrenocortical steroids) such as beclomethasone, triamcinolone, flurisolide, or dexamethasone.

Further, a compound of the invention may be used in the treatment of immunomediated inflammatory skin conditions, such as urticaria and angioedema, eczematous dermatitis, and hyperproliferative skin disease, for example, psoriasis. In such cases, a compound of the invention could be administered topically so as treat the condition involved. Thus, by treating the animal with a topical preparation comprising a compound of the invention, one would expect a decrease in scaling, erythema, size of the plaques, pruritus and other symptoms associated with the skin condition. The dosage of medicament and the length of time required for treating each patient may vary, but one skilled in the art will recognize that variations may occur from patient to patient and adjust the treatment regimen accordingly.

Thus, in a further embodiment of the invention, there is provided a pharmaceutical preparation for topical application comprising a compound of the invention, typically in concentrations in the range of from about 0.001% to about 10%, in combination with a pharmaceutically acceptable carrier, excipient, or diluent therefor. Such topical preparations can be prepared by combining the compound of the invention with conventional pharmaceutical diluents and carriers commonly used in topical dry, liquid, cream and aerosol formulations. Ointment and creams may be formulated, for example, with an aqueous or oily base with the addition of suitable thickening and/or gelling agents. Such bases may include water and/or an oil such as a liquid paraffin or a vegetable oil such as peanut oil or castor oil. Thickening agents which may be used according to the characteristics of the base may include, for example, soft paraffin, aluminum stearate, cetostearyl alcohol, propylene glycol, polyethylene glycols, woolfat, hydrogenated lanolin, beeswax, and the like.

Lotions may be formulated with an aqueous or oily base and will include also, in general, one or more of the following: stabilizing agents emulsifying agents, dispersing agents, suspending agents, thickening agents, coloring agents, perfumes, and the like.

Powders may be formed with the aid of any suitable powder bases, for example, talc, lactose, starch and the like. Drops may be formulated with an aqueous base or non-aqueous base also comprising one or more dispersing agents, suspending agents solubilizing agents, and the like.

Any of the formulations of the invention may also include one or more preservatives or bacteriostatic agents, for example, methyl hydroxybenzoate, ethyl hydroxybenzoate, propyl hydroxybenzoate, chlorocresol, benzalkonium chlorides, and the like. Additionally, the formulations may contain other active ingredients such as antimicrobial agents, particularly antibiotics, anesthetics, analgesics and antipruritic agents.

The pharmaceutical formulations of the invention may be administered by parenteral or oral administration for prophylactic and/or therapeutic treatment. The pharmaceutical compositions can be administered in a variety of unit dosage forms depending on the method of administration. For example, unit dosage forms suitable for oral administration may include, powders, tablets, pills, capsules and dragees.

The pharmaceutical formulations can be administered intravenously. Therefore, the invention further provides formulations for intravenous administration which comprise a compound of the invention dissolved or suspended in a pharmaceutically acceptable carrier or diluent therefor. A variety of aqueous carriers can be used, for example, water, buffered water or other buffer solutions, saline, and the like. The resulting aqueous solutions can be packaged for use as is, or lyophilized, the lyophilized preparation being combined with a sterile aqueous solution prior to administration. The sterile aqueous solution for the lyophilized product can be packaged as a kit for use with the lyophilized formulation. The compositions can contain pharmaceutically acceptable substances to aid in administration and more closely mimic physiological conditions. Such substances, can include, for example, pH adjusting substances such as acids, bases or buffering agents, tonicity adjusting agents, wetting agents and the like. Such substances may include but are not limited to, for example, sodium hydroxide, hydrochloric acid, sulfuric acid, sodium acetate, sodium lactate, sodium chloride, potassium chloride, calcium chloride, sorbitan monolaurate, triethanolamine oleate, and the like or any other means familiar to one skilled in the art for maintaining pH at a desired level.

For solid formulations, carriers, diluents, and excipients known to one skilled in the art may be used. Such carriers, diluents and excipients may include, for example, mannitol, lactose, starch magnesium stearate, sodium saccharin, talcum, cellulose, glucose, sucrose, or other solid polyol sugar, magnesium carbonate, and the like. For oral administration, a pharmaceutically acceptable formulation is prepared by admixing any of the usual carrier, diluents, and excipients, such as those noted, with from about 0.1 to about 95% of a compound of the invention.

Generally, the compounds of Formula (I) may be prepared according to the following procedures. In particular, for the preferred compounds of Formula (I), a compound of Formula (II):

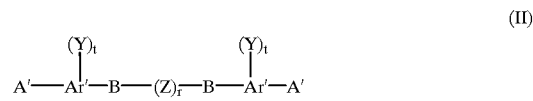
(II)

is reacted with a compound of Formula (III):

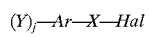

wherein A' is $[(CH_2)_m-C(O)]_r-NHR^2$, and Ar, Ar', $R^2$, Y, B, Z, j, t and r, X is $-SO_2-$ or $-C(O)-$ and Hal is a halogen, all as defined previously, and, if desired, isolating the product.

In a further optional step, if desired for an appropriate compound of Formula (I), the product of the reaction may be salified to prepare a pharmaceutically acceptable salt of the invention. Alternatively, and/or additionally, in a further embodiment for an appropriate compound of Formula (I), the product of the reaction may be esterified to prepare a pharmaceutically acceptable ester of the invention as previously defined.

In an especially preferred embodiment, the compounds of Formula (I) are prepared by reacting a compound of Formula (IIb):

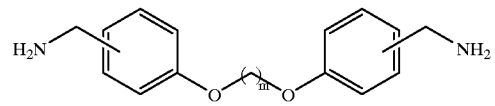
(IIb)

with a compound of Formula (III):

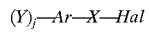

wherein m, Y, j, Ar, X, and Hal are as defined previously, and, optionally isolating the product and/or esterifying and/or salifying the product.

The following alternate general methods for preparing the compounds of Formula (I) are provided to further describe the invention. In the noted processes provided herein, "P" represents a protecting group as known to one skilled in the art and defined below:

Alternate Scheme I:

A compound of the formula:

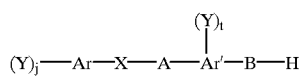

is reacted with a compound of the formula:

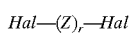

By way of example only this alternate synthetic scheme can be represented by the following reaction:

A compound of the formula:

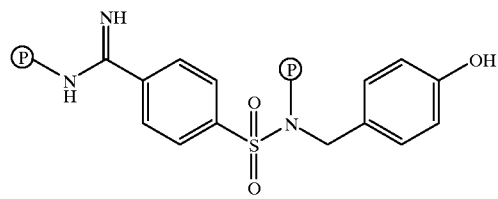

is reacted with a di-halo derivative, for example the di-bromo compound, of the formula:

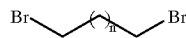

under basic conditions, for example using potassium carbonate in DMF, in accordance with procedures outlined in, for example, D. Dhif et. al., *Heterocycles*, 29, 1149 (1989).

In an alternate method following the scheme noted above, the di-halo derivative noted may be instead a di-hydroxy derivative, for example:

In such a case, the coupling reaction may be performed in the presence of triphenylphosphine and diisopropyl diazodicarboxylate ("DIAD") in, for example, THF according to the procedure of O. Mitsunobu, Synthesis, 1 (1981).

Alternate Scheme II:

In an alternate synthetic scheme, a compound of the formula:

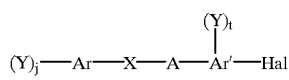

is reacted with a compound of the formula:

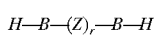

Representative of this synthetic scheme is the following reaction wherein a compound of the formula:

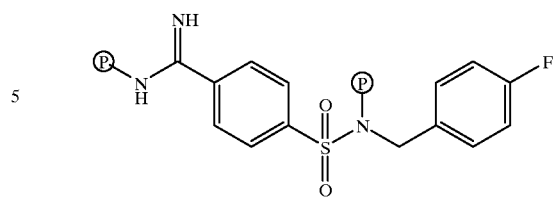

is reacted with the di-hyroxy compound of the formula:

in the presence of base, for example, aqueous sodium hydroxide, according to the method described in C. Ziegler et al. *J. Het. Chem.* 26, 1141 (1989).

In the case where B is a nitrogen atom, the following alternate scheme may be used:

A compound of the formula:

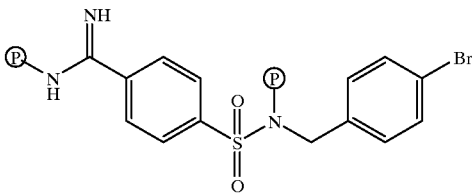

is reacted with a di-amino derivative of the formula:

in the presence of a catalyst, for example PdCl$_2$(PAr$_3$)$_2$, wherein Ar is an aryl moiety such as phenyl, in the presence of a base, for example sodium t-butoxide in toluene, in accordance with procedures provided in, for example, A. Guran, et al., Angew. Chem. 12 1456 (1995).

Alternate Scheme III:

In a further alternative reaction scheme, a compound of the formula:

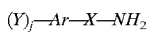

is reacted with a compound of the formula:

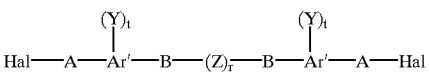

Exemplary of this reaction is the reaction of a compound of the formula:

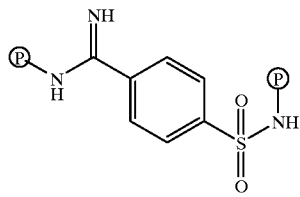

with a di-aryl-di-halo compound of the formula:

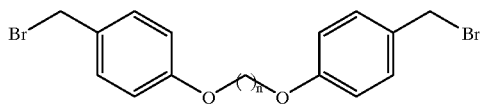

in the presence of base, for example potassium carbonate in DMF, in accordance with the procedure described in, for example, F. Chavez, et al., *J. Org. Chem.*, 54(12), 2990 (1989).

Alternate Scheme IV:

In yet a further alternate method for preparing the compounds of the invention, a compound of the formula:

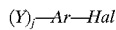

is reacted with a compound of the formula:

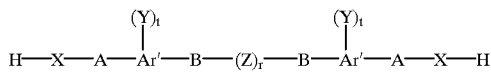

Exemplary of this reaction is the reaction of a compound of the formula:

with a compound of the formula:

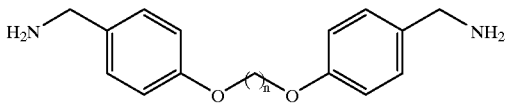

in the presence of carbon monoxide and a catalyst, for example, $PdCl_2(PPh_3)_2$, in accordance with the procedures described in F. Ozawa, et al., *J. Am. Chem. Soc.*, 107(11) 3235 (1985).

In each of Alternate Schemes I–IV, Y, t, r, j, Ar, Ar', A, B, X, Z and Hal are as defined previously. Further, the processes may optionally include isolating the product and/or esterifying and/or salifying the product.

The reactions used to prepare the compounds of Formula (I) may be carried out in any number of solvents in which the reactants may be mutually soluble, including, for example, tetrahydrofuran, benzene, toluene, chloroform, dichloromethane, N,N-dimethylformamide, ethyl ether, dioxane, acetonitrile, or the like. Generally the reaction is carried out at a temperature of between −80° and 150° C., preferably, however, at room temperature.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC using, for example, dilute trifluoroacetic acid in water, acetonitrile, or methanol mixtures as eluent), column chromatography, flash chromatography, radial chromatography, trituration, and the like.

The compounds of Formula (I) in which the portion of the molecule between Ar and Ar' is an amine linkage can be prepared according to the process defined above for the amide compounds followed by a suitable reducing agent such as lithium aluminum hydride, sodium tetrahydroborate, 9-BBN, lithium trethylborohydride, diethyl aluminum hydride, and the like. Such reductions generally are performed at −80° C. to room temperature under anhydrous conditions.

A typical reaction scheme for preparing the preferred compounds of Formula (I) is provided below:

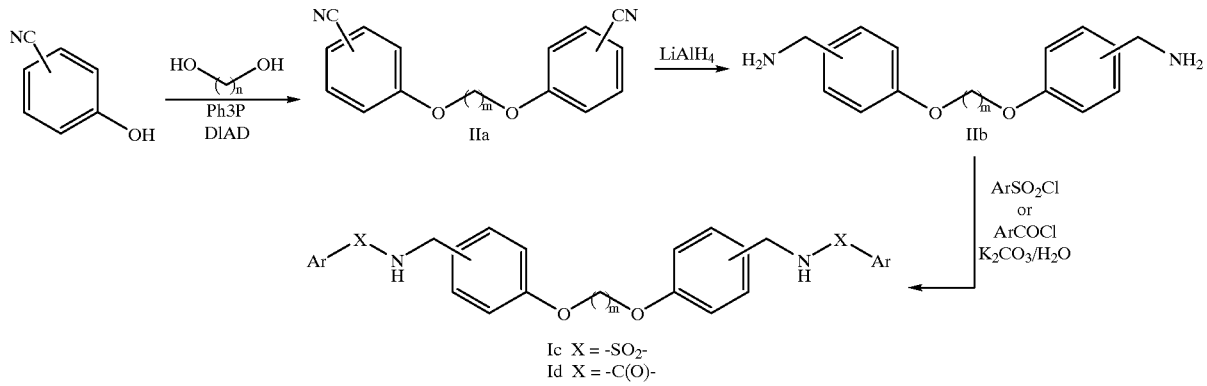

In the preparation of the compounds of the invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, Ed., Plenum Press, New York, New York; and "Protective Groups in Organic Synthesis," Greene, Ed., John Wiley & Sons, New York, N.Y. (1981) for the teaching of protective groups which may be useful in the preparation of compounds of the present invention.

Alternate means beyond those described above for preparing the compounds of the invention will be apparent to one skilled in the art and the noted general procedures are not to be construed as limiting the invention. To more fully understand the invention, including methods of preparing compounds of the invention, the following non-limiting examples are provided. The reader will appreciate that starting materials not otherwise described herein are either available commercially or can be prepared by methods known in the art. The symbols used to denote $^1$H NMR signals are as follows: s=singlet, d=doublet, t=triplet, q=quartet, p=pentet, dd=doublet of doublets, dt=doublet of triplets, br s=broad singlet, br d=broad doublet, br t=broad triplet, m=multiplet, c=complex.

EXAMPLE 1

Preparation of Dibenzonitrile Compounds

The synthesis of the dibenzonitrile compounds of Formula (IIa):

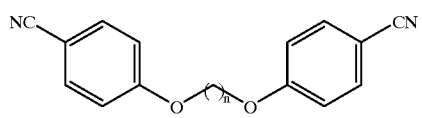

is generally exemplified by the following procedure wherein n is 6:

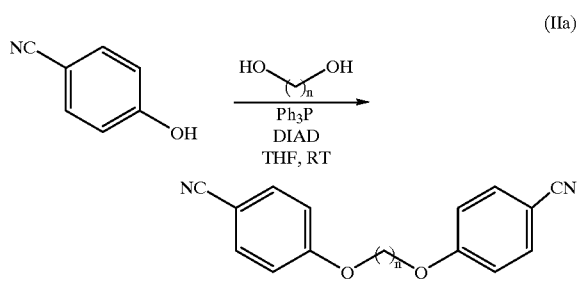

4,4'-Hexanediyldioxy-dibenzonitrile (Formula (IIa), n=6)

To a cooled (0° C.), stirred solution of triphenylphosphine (8.88 g; 33.8 mmol) in dry THF (50 mL) was added, via syringe, diisopropylazodicarboxylate (6.66 mL; 33.8 mmol) under an atmosphere of argon. After ten minutes, a tan precipitate formed and more THF (20 mL) was added. After stirring for thirty minutes, a solution of 1,6-hexanediol (2.00 g; 16.9 mmol) in dry THF (25 mL) was added via syringe. The resulting cloudy solution was allowed to warm to room temperature and stir for one hour. This solution was then transferred to an addition funnel and added dropwise over forty-five minutes to a stirred solution of 4-cyanophenol (4.03 g; 33.8 mmol) in dry THF (40 mL) at room temperature. The resulting clear yellow solution was stirred at room temperature for forty hours. The reaction mixture was diluted with ethyl acetate (300 mL) and washed successively with 1 N aqueous HCl (2×100 mL), 1 N aqueous NaOH (2×100 mL), and brine (150 mL) then dried (MgSO$_4$), filtered and concentrated in vacuo to provide the crude diether. Purification via flash chromatography on silica gel (neat CH$_2$Cl$_2$ eluent) returned the pure diether as a white solid (3.3 g; 61% yield).

LRMS (electrospray) m/z: 321 (M+1), 338 (M+18).

$^1$H NMR (CDCl$_3$): δ7.60 (d, 4H, J=8.0 Hz), 6.95 (d, 4H, J=9.0 Hz), 4.03 (t, 4H, J=6.3 Hz), 1.86 (c, 4H), 1.57 (C, 4H).

EXAMPLE 2

4,4'-Heptanediyldioxy-dibenzonitrile (Formula (IIa), n=7)

The noted compound was prepared according to the procedure defined in Example 1 using 1,7-heptanediol to provide the pure diether as a white solid (60% yield). $^1$H NMR (CDCl$_3$): δ7.58 (d, 4H, J=8.5 Hz), 6.94 (d, 4H, J=9.0 Hz), 4.02 (t, 4H, J=6.3 Hz), 1.84 (c, 4H), 1.51 (c, 6H).

EXAMPLE 3

4,4'-Pentanediyldioxy-dibenzonitrile (Formula (IIa). n=5)

The noted compound was prepared according to the procedure defined in Example 1 using 1,5-pentanediol to provide the pure diether as a white solid (54% yield) LRMS (electrospray) m/z: 307 (M+1), 324 (M+18). $^1$H NMR (CDCl$_3$): δ7.59 (d, 4H, J=8.5 Hz), 6.95 (d, 4H, J=8.5 Hz), 4.06 (t, 4H, J=6.3 Hz), 1.90 (c, 4H), 1.69 (c, 2H).

$^{13}$C NMR (CDCl$_3$): δ162.2, 133.9, 119.2, 115.0, 103.6, 68.0, 28.6, 22.5.

EXAMPLE 4

4,4'-Butanediyldioxy-dibenzonitrile (Formula (IIa), n=4)

The noted compound was prepared according to the procedure outlined in Example 1 using 1,4-butanediol to provide the pure diether as a white solid (52% yield).

LRMS (electrospray) m/z: 293 (M+1), 310 (M+18).

$^1$H NMR (CDCl$_3$): δ7.60 (d, 4H, J=9.0 Hz), 6.96 (d, 4H, J=9.0 Hz), 4.11 (t, 4H, J=5.3 Hz), 2.04 (c, 4H).

EXAMPLE 5

4,4'-Propanediyldioxy-dibenzonitrile(Formula (IIa), n=3)

The noted compound was prepared according to the procedure outlined in Example 1 using 1,3-propanediol to provide the pure diether as a white solid (63% yield).

19

Alternative Preparation:

4,4'-Propanediyldioxy-dibenzonitrile (n=3)

To a solution of 4-cyanophenol (20.0 g; 0.16 mol) in DMF (350 mL) was added powdered potassium carbonate (34.8g; 0.25 mol) under an atmosphere of argon. This mixture was stirred at room temperature for 15 minutes. To the reaction mixture was added 1,3-dibromopropane (8.52 mL; 0.08 mol) via syringe, and the mixture stirred at room temperature for 16 hours. The solvent was removed by high vacuum distillation and the remaining white solid was taken up in 200 mL of EtOAc. HCl (1N in water) was then added and a white precipitate formed. This precipitate was collected by filtration, washed several times with diethyl ether, and then dried under vacuum. A total of 20.2 g of a white solid were obtained (90% yield).

LRMS (electrospray) m/z: 279 (M+1).

$^1$H NMR (D$_8$ THF): δ7.65 (d, 4H, J=9.0 Hz), 7.09 (d, 4H, J=8.5 Hz), 4.28 (t, 4H, J=6.1 Hz), 2.32 (p, 2H, J=6.1 Hz).

EXAMPLE 6

4,4'-Ethanediyldioxy-dibenzonitrile (Formula (IIa), n=2)

The noted compound was prepared according to the procedure outlined in Example 1 using ethylene glycol to provide the pure diether as a white solid (28% yield).

LRMS (electrospray) m/z: 282.2(M+18).

$^1$H NMR (CD$_3$OD): δ7.69 (d, 4H, J=9.0 Hz), 7.14 (d, 4H, J=8.0 Hz), 4.46 (s, 4H).

EXAMPLE 7

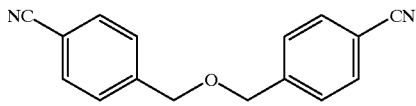

4,4'-(2-Oxa-propanediyl)-di-benzonitrile

To a cooled (0° C.), stirred solution of 4-cyanobenzyl alcohol (637 mg, 4.8 mmol) in dry THF (15 mL) was added a dispersion of sodium hydride in mineral oil (60%; 192 mg, 4.8 mmol), portionwise over five minutes under an argon atmosphere. The resulting milky white solution was allowed to warm to room temperature and stirred for three hours (bubbling was observed). To the resulting light green mixture was added dry dimethylformamide (3 mL) to improve homogeneity. After stirring for an additional hour, the 4-cyanobenzyl bromide (930 mg, 4.8 mmol) was added. The resulting yellow, cloudy mixture was stirred at room temperature overnight. The reaction was then carefully quenched with the addition of 1 N aqueous HCl (15 mL) and extracted with ether (3×30 mL). The combined ethereal extracts were washed with water and brine then dried (MgSO$_4$), filtered and concentrated in vacuo to provide the desired ether as a light yellow solid (1.06 g, 89%). No further purification was necessary.

LRMS (electrospray) m/z: 266.2 (M+18).

$^1$H NMR (CDCl$_3$): δ7.69 (d, 4H, J=8.3 Hz), 7.50 (d, 4H, J=8.5 Hz), 4.67 (s, 4H).

20

PREPARATION OF THE BIS-BENZYLAMINES

The synthesis of the benzylamine compounds of Formula (IIb):

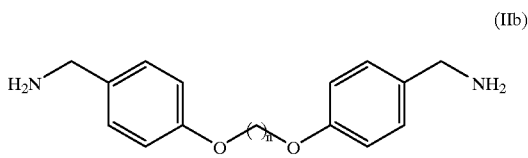

is generally exemplified by the following procedure wherein n is 7:

EXAMPLE 8

4-[7-(4-Aminomethyl-phenoxy)-heptyloxy]-benzylamine (Formula (IIb), n=7)

To a vigorously stirred solution of bis-nitrile prepared according to Example 2 (0.22 g; 0.64 mmol) in dry THF (7 mL) was added a solution of lithium aluminum hydride (1.9 mL; 1.0 M in THF; 1.9 mmol) via syringe at room temperature under argon atmosphere. The resulting yellow solution was refluxed for 5 hours (after a precipitate forms, another 10 mL of THF was added to provide a slurry). After cooling to room temperature the reaction mixture was carefully quenched with the successive addition of water (0.07 mL), 15% aqueous NaOH (0.07 mL) and water (0.22 mL) [CAUTION: vigorous hydrogen gas evolution]. The resulting mixture was dried (Na$_2$SO$_4$), filtered and concentrated in vacuo to provide the desired diamine as a white solid (0.22 g; 91% yield). No further purification was necessary. $^1$H NMR (CDCl$_3$): δ7.21 (d, 4H, J=8.8 Hz), 6.83 (d, 4H, J=8.5 Hz), 3.96 (t, 4H, J=6.5 Hz), 3.73 (s, 4H), 1.78 (c, 4H), 1.53 (c, 6H).

EXAMPLE 9

4-[6-(4-Aminomethyl-phenoxy)-hexyloxyl-benzylamine (Formula IIb, n=6)

The noted compound was prepared according to the procedure of Example 8 using the bis-benzonitrile of Example 1 to provide the desired diamine as a white solid (90% yield).

LRMS (electrospray) m/z: 329 (M+1).

$^1$H NMR (CD$_3$OD): δ7.24 (d, 4H, J=8.5 Hz), 6.88 (d, 4H, J=8.5 Hz), 3.98 (t, 4H, J=5.9 Hz), 3.72 (s, 4H), 1.81 (c, 4H), 1.56 (c, 4H).

EXAMPLE 10

4-r5-(4-Aminomethyl-phenoxy)-Dentyloxyl-benzylamine (Formula IIb, n=5)

The noted compound was prepared according to the procedure of Example 8 using the bis-benzonitrile of Example 3 to provide the desired diamine as a white solid (98% yield).

LRMS (electrospray) m/z: 315 (M+1).

$^1$H NMR (THF-d$_8$): δ7.22 (d, 4H, J=8.8 Hz), 6.84 (d, 4H, J=8.5 Hz), 3.99 (t, 4H, J=6.4 Hz), 3.74 (s, 4H), 1.86 (c, 4H), 1.68 (c, 2H).

EXAMPLE 11

4-[4-(4-Aminomethyl-phenoxy)-butoxyl-benzylamine (Formula IIb, n=4)

The noted compound was prepared according to the procedure described in Example 8 using the bis-benzonitrile prepared in Example 4 to provide the desired diamine as a white solid (80% yield).

LRMS (electrospray) m/z: 301 (M+1).

$^1$H NMR (CD$_3$OD): δ7.24 (d, 4H, J=8.5 Hz), 6.89 (d, 4H, J=8.5 Hz), 4.05 (t, 4H, J=5.5 Hz), 3.73 (s, 4H), 1.96 (c, 4H).

EXAMPLE 12

4,4'[3-(4-Aminomethyl-phenoxy)-propoxyl-benzylamine (Formula IIb, n=3)

The noted compound was prepared according to the procedure described in Example 8 using the bis-benzonitrile prepared in Example 5 to provide the desired diamine as a white solid (99% yield).

LRMS (electrospray) m/z: 287 (M+1).

$^1$H NMR (THF-d$_8$): δ7.22 (d, 4H, J=8.3 Hz), 6.86 (d, 4H, J=8.8), 4.15 (t, 4H, J=6.2 Hz), 3.73 (s, 4H), 2.23 (c, 2H).

EXAMPLE 13

4-[2-(4-Aminomethyl-phenoxy)-ethoxy]-benzylamine (Formula IIb, n=2)

The noted compound was prepared according to the procedure described in Example 8 using the bis-benzonitrile prepared in Example 6 to provide the desired diamine as a light yellow solid (43% yield).

$^1$H NMR (THF—d$_8$): δ7.25 (d, 4H, J=8.5 Hz), 6.90 (d, 4H, J=8.5 Hz), 4.30 (s, 4H), 3.75 (s, 4H), 2.46 (br s, 4H).

EXAMPLE 14

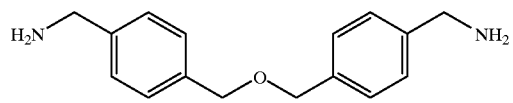

4-(4-Aminomethyl-benzyloxymethyl)-benzylamine

The noted compound was prepared according to the procedure describe in Example 8 using the bis-benzonitrile prepared in Example 7 to provide the desired diamine as a white solid (89% yield). $^1$H NMR (DMSO-d$_6$): δ7.31 (d, 4H, J=8.3 Hz), 7.27 (d, 4H, J=8.5 Hz), 4.48 (s, 4H), 3.69 (s, 4H), 3.33 (br s, 4H).

PREPARATION OF BIS-SULFONYLAMINO COMPOUNDS

The synthesis of the bis-sulfonylamino compounds of Formula (Ic):

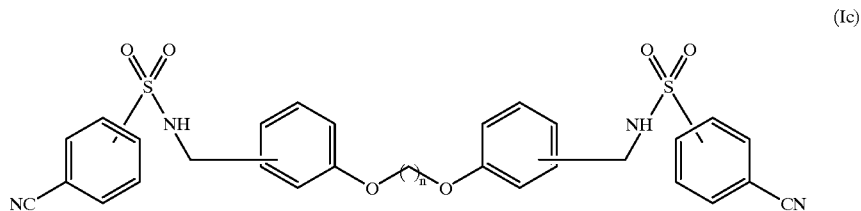

(Ic)

is exemplified by the following general procedure which is provided in detail in Example 15 in which n is 7:

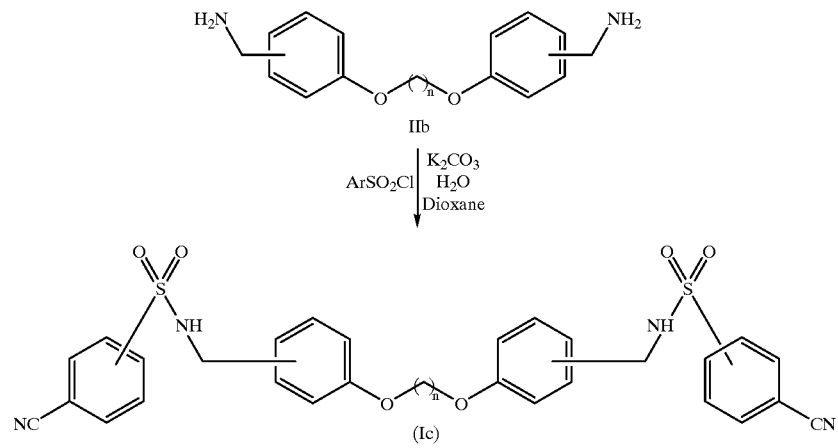

EXAMPLE 15

1,7-Bis-{4-[(4-cyano-benzenesulfonylamino)-methyl]-phenoxy}-heptane (Formula (Ic), n=7)

To a clear, colorless, vigorously stirred solution of the bis-benzylamine prepared in Example 8 (0.99 g; 2.9 mmol) in 10% aqueous potassium carbonate (22 mL; 15.9 mmol) and 1,4-dioxane (15 mL) was added 4-cyano-benzene sulfonyl chloride (1.17 g; 5.8 mmol). The initially resulting mixture became a clear yellow solution then, upon further stirring, became a slurry. After stirring for 20 hours, the reaction was acidified to pH 1 with 1 N aqueous HCl and extracted with ethyl acetate (4×100 mL). The organic extracts were combined, washed with brine (75 mL), dried (MgSO$_4$), filtered and concentrated in vacuo to provide the desired bis-sulfonamide as a white solid (1.88 g; 97%). No further purification was necessary.

$^1$H NMR (THF—d$_8$): δ7.95 (d, 4H, J=8.0 Hz), 7.87 (d, 4H, J=8.0 Hz), 7.21 (br s, 2H), 7.09 (d, 4H, J=8.5 Hz), 6.78 (d, 4H, J=8.5 Hz), 4.05 (d, 4H, J=5.5 Hz), 3.94 (d, 4H, J=6.5 Hz), 1.76 (c, 4H), 1.49 (c, 6H).

One skilled in the art will note that compounds derived from benzylamines of lower molecular weight are less soluble in ethyl acetate so the acidified reaction mixture may be simply filtered, rather than extracted, to provide the desired product.

EXAMPLE 16

1,7-Bis-{4-(3-cyano-benzenesulfonylamino)-methyl]-phenoxy}-heptane (Formula (Ic), n=7)

The noted compound is prepared according to the procedure of Example 15 using the bis-benzylamine of Example 8 and 3-cyanobenzene sulfonyl chloride to provide the crude disulfonamide which was purified by radial chromatography (6 mm plate with dichloromethane eluent) to provide the desired product as a white solid (54% yield).

$^1$H NMR (THF—d$_8$): δ8.12 (t, 2H, J=1.8 Hz), 8.08 (dt, 2H, J=1.5, 8.0 Hz), 7.93 (dt, 2H, J=1.5, 7.5 Hz), 7.70 (t, 2H, J=7.8 Hz), 7.25 (br t, 2H, J=6.5 Hz), 7.12 (d, 4H, J=8.5 Hz), 6.80 (d, 4H, J=9.0 Hz), 4.07 (d, 4H, J=6.0 Hz), 3.96 (t, 4H, J=6.5 Hz), 1.78 (c, 4H), 1.50 (c, 4H).

EXAMPLE 17

1,6-Bis-{4-(4-cyano-benzenesulfonylamino)-methyl]-phenoxy}-hexane (Formula (Ic). n=6)

The noted compound is prepared according to the procedure of Example 15 using the bis-benzylamine prepared according to Example 9 and 4-cyanobenzene sulfonyl chloride to provide the disulfonamide as a light yellow solid (81% yield).

$^1$H NMR (THF—d$_8$): δ7.96 (d, 4H, J=8.0 Hz), 7.89 (d, 4H, J=8.0 Hz), 7.11 (d, 4H, J=8.5 Hz), 6.80 (d, 4H, J=8.5 Hz), 4.07 (s, 4H), 3.97 (t, 4H, J=6.5 Hz), 1.81 (c, 4H), 1.57 (c, 4H).

EXAMPLE 18

1,6-Bis-{4-[(3-cyano-benzenesulfonylamino)-methyl]-phenoxy}-hexane (Formula (Ic), n=6)

The noted compounds is prepared according to the general procedure provided in Example 15 using the bis-benzylamine of Example 9 and 3-cyanobenzene sulfonyl chloride to provide the disulfonamide as a white solid (95% yield).

$^1$H NMR (THF—d$_8$): δ8.12 (s, 2H), 8.07 (d, 2H, J=8.0 Hz), 7.93 (d, 2H, J=7.8 Hz), 7.70 (t, 2H, J=7.8 Hz), 7.11 (d, 4H, J=8.8 Hz), 6.80 (d, 4H, J=8.8 Hz), 4.07 (d, 4H, J=5.8 Hz), 3.97 (t, 4H, J=6.4 Hz), 1.84 (c, 4H), 1.57 (c, 4H).

EXAMPLE 19

1,5-Bis-{4-[(4-cyano-benzenesulfonylamino)-methyl]-phenoxy}-pentane (Formula (Ic), n=5)

The noted compound is prepared according to the general procedure described in Example 15 using the bis-benzylamine prepared in Example 10 and 4-cyanobenzene sulfonyl chloride to provide the disulfonamide as a light yellow solid (89% yield)

LRMS (electrospray) m/z: 662 (M+18).

$^1$H NMR (CD$_3$OD): δ7.87 (d, 4H, J=8.0 Hz), 7.82 (d, 4H, J=8.5 Hz), 7.05 (d, 4H, J=8.5 Hz), 6.75 (d, 4H, J=8.5 Hz), 4.09 (s, 4H), 3.98 (t, 4H, J=6.5 Hz), 1.84 (c, 4H), 1.67 (c, 2H).

EXAMPLE 20

1,5-Bis-{4-[(3-cyano-benzenesulfonylamino)-methyl]-phenoxy}-pentane (Formula (Ic), n=5)

The noted compound is prepared according to the general procedure described in Example 15 using the bis-benzylamine prepared according to Example 10 and 3-cyanobenzene sulfonyl chloride to provide the disulfonamide as a light yellow solid (88% yield).

$^1$H NMR (THF—d$_8$): δ8.11 (s, 2H), 8.06 (d, 2H, J=8.0 Hz), 7.91 (d, 2H, J=8.0 Hz), 7.69 (t, 2H, J=7.8 Hz), 7.11 (d, 4H, J=8.5 Hz), 6.80 (d, 4H, J=8.5 Hz), 4.08 (d, 4H, J=6.0 Hz), 3.99 (t, 4H, J=6.3 Hz), 1.85 (c, 4H), 1.67 (c, 2H).

EXAMPLE 21

1,4-Bis-{4-[(4-cyano-benzenesulfonylamino)-methyl]-phenoxy}-butane (Formula (Ic), n=4)

The noted compound was prepared according to the procedure described in Example 15 using the bis-benzylamine prepared in Example 11 and 4-cyanobenzene sulfonyl chloride to provide the disulfonamide as a yellow solid (78% yield).

$^1$H NMR (DMSO-d$_6$): 8 8.41 (t, 2H, J=6.5 Hz), 8.01 (d, 4H, J=8.5 Hz), 7.87 (d, 4H, J=8.5 Hz), 7.07 (d, 4H, J=8.8 Hz), 6.79 (d, 4H, J=8.8 Hz), 3.97 (di 8H, J=5.3 Hz), 1.84 (c, 4H).

EXAMPLE 22

1,4-Bis-{4-[(3-cyano-benzenesulfonylamino)-methyl]-phenoxy}-butane (Formula (Ic), n=4)

The noted compound was prepared according to the general procedure provided in Example 15 using the bis-benzylamine of Example 11 and 3-cyanobenzene sulfonyl chloride to provide the disulfonamide as a yellow solid (94% yield).

LRMS (electrospray) m/z: 648 (M+18).

$^1$H NMR (THF—$_8$): δ8.12 (s, 2H), 8.07 (d, 2H, J=8.0 Hz), 7.92 (d, 2H, J=7.5 Hz), 7.70 (t, 2H, J=7.9 Hz), 7.12 (d, 4H, J=8.5 Hz), 6.82 (d, 4H, J=8.8 Hz), 4.08—4.02 (m, 8H), 1.95 (c, 4H) .

EXAMPLE 23

1,3-Bis-{4-[(4-cyano-benzenesulfonylamino)-methyl]-phenoxy}-propane (Formula (Ic), n=3)

The noted compound was prepared according to the procedure of Example 15 using the bis-benzylamine of Example 12 and 4-cyanobenzene sulfonyl chloride to provide the disulfonamide as a white solid (90% yield)

¹H NMR (THF—d$_8$): δ7.96 (d, 4H, J=8.3 Hz), 7.89 (d, 4H, J=8.3 Hz), 7.22 (br s, 2H), 7.11 (d, 4H, J=8.8 Hz), 6.84 (d, 4H, J=8.5 Hz), 4.14 (t, 4H, J=6.3 Hz), 4.06 (d, 4H, J=5.8 Hz), 2.22 (c, 2H).

EXAMPLE 24

1,3-Bis-{4-[(3-cyano-benzenesulfonylamino)-methyl]-phenoxy}-propane (Formula (Ic), n=3)

The noted compound was prepared according to the procedure of Example 15 using the bis-benzylamine of Example 12 and 3-cyanobenzene sulfonyl chloride to provide the disulfonamide as a yellow solid (93% yield).

¹H NMR (THF—d$_8$): δ8.10 (t, 2H, J=1.6 Hz), 8.06 (dt, 2H, J=1.4, 8.0 Hz), 7.89 (dd, 2H, J=1.4, 7.8 Hz), 7.67 (t, 2H, J=7.9 Hz), 7.12 (d, 4H, J=8.5 Hz), 6.83 (d, 4H, J=8.5 Hz), 4.15 (t, 4H, J=6.3 Hz), 4.08 (d, 4H, J=5.8 Hz), 2.22 (c, 2H).

EXAMPLE 25

1,2-Bis-{4-[(4-cyano-benzenesulfonylamino)-methyl]-phenoxy}-ethane (Formula (Ic), n=2)

The noted compound was prepared according to the procedure described in Example 15 using the bis-benzylamine of Example 13 and 4-cyanobenzene sulfonyl chloride to provide the disulfonamide as a light yellow solid (96% yield).

¹H NMR (DMSO—d$_6$): δ8.42 (t, 2H, J=6.0 Hz), 8.04 (d, 4H, J=8.0 Hz), 7.90 (d, 4H, J=8.0 Hz), 7.12 (d, 4H, J=8.5 Hz), 6.86 (d, 4H, J=8.5 Hz), 4.25 (s, 4H), 3.98 (d, 4H, J=6.3 Hz), 3.40 (br s, 4H).

EXAMPLE 26

1,2-Bis-{4-[(3-cyano-benzenesulfonylamino)-methyl]-phenoxy}-ethane (Formula (Ic), n=2)

The noted compound was prepared according to the procedure of Example 15 using the bis-benzylamine of Example 13 and 3-cyanobenzene sulfonyl chloride to provide the disulfonamide as a yellow solid (93% yield).

¹H NMR (DMSO-d$_6$): δ8.08—8.02 (c, 6H), 7.76 (t, 2H, J=8.3 Hz), 7.11 (d, 4H, J=8.8 Hz), 6.85 (d, 4H, J=8.5 Hz), 4.25 (s, 4H)₁ 4.00 (s, 4H).

EXAMPLE 27

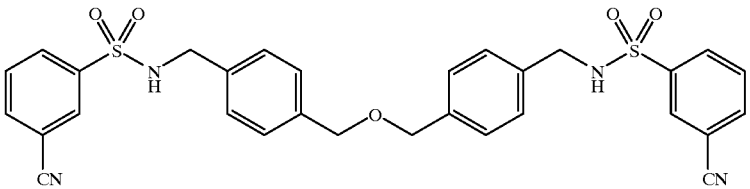

1,3-Bis-{4-[(3-cyano-benzenesulfonylamino)-methyl]-phenyl}-2-oxapropane

The noted compound was prepared according to the procedure described in Example 15 using the bis-benzylamine of Example 14 and 3-cyanobenzene sulfonyl chloride to provide the disulfonamide as a yellow solid (93% yield).

LRMS (positive electrospray) m/z: 604.0 (M+18).
LRMS (negative electrospray) m/z: 585.2 (M−1).

¹H NMR (DMSO—d$_6$): δ8.43 (t, 2H, J=5.8 Hz), 8.09— 8.03 (c, 6H), 7.75 (t, 2H, J=7.8 Hz), 7.22 (d, 4H, J=8.3 Hz), 7.19 (d, 4H, J=8.5 Hz), 4.44 (s, 4H), 4.07 (d, 4H, J=66.3 Hz).

PREPARATION OF BIS-AMIDO COMPOUNDS

The synthesis of the bis-amido compounds of Formula (Ib):

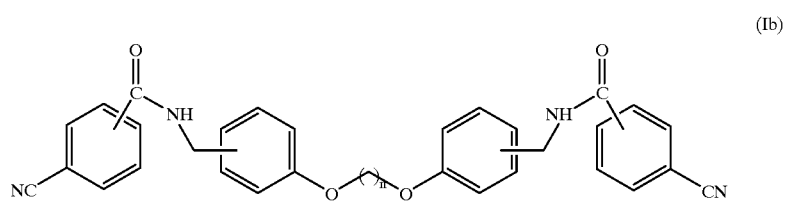

(Ib)

is exemplified by the following general procedure which is provided in detail in Example 28 in which n is 3:

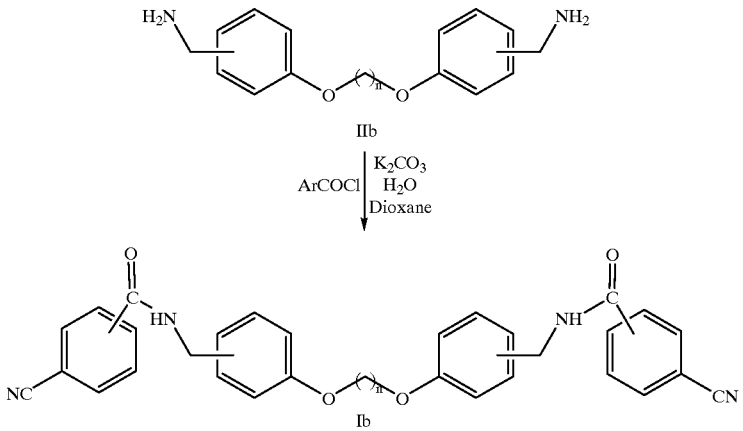

EXAMPLE 28

1,3-Bis-{4-[(3-cyano-benzoylamino)-methyl]-phenoxy}-propane (Formula (Ib), n=3)

To a clear, colorless, vigorously stirred solution of the bis-benzylamine of Example 12 (0.23 g; 0.80 mmol) in 10% aqueous potassium carbonate (6.1 mL; 4.4 mmol) and 1,4-dioxane (10 mL) was added 3-cyanobenzoyl chloride (0.27 g; 1.6 mmol). The initially resulting mixture became a clear solution then, upon further stirring, became cloudy. After stirring for 20 hours, the reaction was acidified to pH 1 with 1 N aqueous HCl and the resulting solids were trapped on a Buchner funnel with suction. The solids were dried further in vacuo to provide the desired bis-amide as a white solid (0.41 g; 94%). No further purification was necessary.

$^1$H NMR (THF—$d_8$): δ8.20 (d, 2H, J=1.5 Hz), 8.17 (dt, 2H, J=1.5, 8.0 Hz), 7.84 (dt, 2H, J=1.4, 7.8 Hz), 7.62 (t, 2H, J=7.8 Hz), 7.28 (d, 4H, J=8.5 Hz), 6.89 (d, 4H, J=8.5 Hz), 4.53 (d, 4H, J=6.0 Hz), 4.16 (t, 4H, J=6.2 Hz), 2.23 (c, 2H).

One skilled in the art will appreciate that other preparations with higher molecular weight diamines were more soluble, so extraction with four portions of ethyl acetate, followed by washing with brine, drying (MgSO$_4$), filtering and concentrating in vacuo provided the desired product.

EXAMPLE 29

1,3-Bis-{4-[(4-cyano-benzoylamino)-methyl]-phenoxy}-propane (Formula (Ib), n=3)

The noted compounds was prepared according to the general procedure outlined in Example 28 using the bis-benzylamine of Example 12 and 4-cyanobenzoyl chloride to provide the diamide as a light yellow solid (88% yield).

$^1$H NMR (THF-$d_8$): δ8.15 (br s, 2H), 8.01 (d, 4H, J=8.3 Hz), 7.81 (d, 4H, J=8.0 Hz), 7.28 (d, 4H, J=8.3 Hz), 6.89 (d, 4H, J=8.5 Hz), 4.52 (d, 4H, J=5.8 Hz), 4.16 (t, 4H, J=6.2 Hz), 2.24 (c, 2H).

EXAMPLE 30

1,7-Bis-{4-[(4-cyano-benzenecarbonylamino)-methyl]-phenoxy}-heptane (Formula (Ib), n=7)

The noted compound was prepared according to the procedure described in Example 28 using 4-cyanobenzoyl chloride and the bis-benzyl amine of Example 8 to provide the desired bis-amide as a light yellow solid (82% yield).

$^1$H NMR (DMSO—$d_6$): δ9.24 (t, 2H, J=6.0 Hz), 8.02 (d, 4H, J=6.5 Hz), 7.96 (d, 4H, J=6.5 Hz), 7.21 (d, 4H, J=9.1 Hz), 6.86 (d, 4H, J=9.1 Hz), 4.40, (d, 4H, J=6.0 Hz), 3.92 (m, 4H), 1.6 (m, 4H), 1.38 (m, 6H).

EXAMPLE 31

1,7-Bis-{4-[(3-cyano-benzenecarbonylamino)-methyl]-phenoxy}-heptane (Formula (Ib), n=7)

The noted compound was prepared according to the procedure outlined in Example 28 using 3-cyanobenzoyl chloride and the bis-benzyl amine of Example 8 to provide the bis-amide as a white solid (60% yield).

$^1$H NMR (DMSO—$d_6$): δ9.17 (t, 2H, J=5.6 Hz), 8.29 (s, 2H), 8.17 (d, 2H, J=7.0 Hz), 8.00 (d, 2H, J=7.0 Hz), 7.69 (t, 2H, J=7.0 Hz), 7.30 (d, 4H, J=8.0 Hz), 7.23 (d, 4H, J=8.0 Hz), 4.40 (d, 4H, J=5.6 Hz), 3.92 (m, 4H), 1.68 (m, 4H), 1.38 (m, 6H).

EXAMPLE 32

1,6-Bis-{4-[(4-cyano-benzenecarbonylamino)-methyl]-phenoxy}-hexane (Formula (Ib), n=6)

The noted compound was prepared according to the procedure described in Example 28 using 4-cyanobenzoyl chloride and the bis-benzyl amine of Example 9 to provide the desired bis-amide as a white solid (50% yield).

$^1$H NMR (CDCl$_3$): δ7.87 ( d, 4H, J=8.0 Hz), 7.73 (d, 4H, J=8.0 Hz), 7.26 (d, 4H, 8.0 Hz), 6.88 (d, 4H, J=8.0 Hz), 6.39 (br s. 2H), 4.56 (d, 4H, J=5.6 Hz), 3.97 (t, 4H, J=6.5), 1.82 (m, 4H), 1.55 (m, 4H).

EXAMPLE 33

1,6-Bis-{4-[(3-cyano-benzenecarbonylamino)-methyl]-phenoxy}-hexane (Formula (Ib), n=6)

The noted compound was prepared according to the general procedure outlined in Example 28 using 3-cyanobenzoyl chloride and the bis-benzyl amine of Example 9 to provide the desired bis-amide as a white solid (34% yield).

$^1$H NMR (CDCl$_3$): δ8.06 (s, 2H), 8.02(d, 2H, J=8.0 Hz), 7.78 (d, 2H, 7.5 Hz), 7.57 (t, 2H, J=8.0, 7.5 Hz), 5 7.24 (4H), 6.98 (d, 4H, J=8.5 Hz). 6.35 (br s , 2H), 4.58 (d, 4H, J=5.1 Hz), 3.99 (t, 4H, J=6.0 Hz), 1.82 (m, 4H), 1.55 (m, 4H).

EXAMPLE 34

1,5-Bis-{4-[(4-cyano-benzenecarbonylamino)-methyl]-phenoxy}-pentane (Formula (Ib) n=5)

The noted compound was prepared according to the general procedure outlined in Example 28 using 4-cyanobenzoyl chloride and the bis-benzyl amine of Example 10 to provide the desired bis-amide as a pale yellow solid (83% yield).

$^1$H NMR (DMSO—$d_6$): δ9.29 (t, 2H, J=3.5 Hz), 8.01 (d, 4H, J=8.0 Hz), 7.94 ( d, 4H, J=8.0 Hz), 7.21 (d, 4H, J=8.6 Hz), 6.86 (d, 4H, J=8.6 Hz), 4.39 (d, 4H, J=3.5 Hz), 3.92 (t, 4H, J=6.3 Hz), 1.72 (m, 4H), 1.52 (m, 2H).

EXAMPLE 35

1,5-Bis-{4-[(3-cyano-benzenecarbonylamino)-methyl]-phenoxy}-pentane (Formula (Ib), n=S)

The noted compound was prepared according to the procedure outlined in Example 28 using 3-cyanobenzoyl chloride and the bis-benzyl amine of Example 10 to provide the desired bis-amide as a tan solid (99% yield).

$^1$H NMR (DMSO—$d_6$): δ9.20 (m, 2H), 8.30 (s, 2H), 8.18 (d, 2H, J=8.0 Hz), 8.01 (d, 2H, J=8.0 Hz), 7.69 (t, 2H, J=8.0 Hz) 7.23 (d, 4H, J=8.5 Hz), 6.87 (d, 4H, J=8.5 Hz), 4.41 (d, 4H, J=3.5 Hz), 3.95 (t, 4H, J=7.5 Hz), 1.75 (m, 4H), 1.54 (m, 2H).

EXAMPLE 36

1,4-Bis-{4-[(4-cyano-benzenecarbonylamino)-methyl]-phenoxy}-butane (Formula (Ib), n=4)

The noted compound was prepared according to the procedure described in Example 28 using 4-cyanobenzoyl chloride and the bis-benzyl amine of Example 11 to provide the desired bis-amide as a white solid (74% yield).

$^1$H NMR (DMSO—$d_6$): δ8.01 (m, 8H), 7.23 (d, 4H, J=9.0 Hz), 6.88 (d, 4H, J=9.0 Hz), 4.4 (br s, 4H), 3.98 (br s, 4H), 1.82 (br s, 2H).

EXAMLE 37

1,4-Bis-{4-[(3-cyano-benzenecarbonylamino)-methyl]-phenoxy}-butane (Formula (Ib), n=4)

The noted compound was prepared according to the procedure described in Example 28 using 3-cyanobenzoyl chloride and the bis-benzyl amine of Example 11 to provide the desired bis-amide as a white solid (60% yield).

$^1$H NMR (DMSO—$d_6$): δ9.21 (m, 2H), 8.30 (s, 2H), 8.18 (d, 2H, J=8.0 Hz), 8.01 (d, 2H, J=8.0 Hz), 7.70 (t, 2H, J=8.0 Hz), 7.24 (d, 4H, J=9.0 Hz) , 6.89 ( d, 4H, J=9.0 Hz), 4.41 (d, 4H, J=4.0 Hz), 3.98 (m, 4H), 1.83 (m, 4H).

EXAMPLE 38

1,2-Bis-{4-[(4-cyano-benzenecarbonylamino)-methyl]-phenoxy}-ethane (Formula (Ib), n=2)

The noted compound was prepared according to the procedure outlined in Example 28 using the bis-benzylamine of Example 13 and 4-cyanobenzoyl chloride to provide the desired bis-amide as a light yellow solid (62% yield).

$^1$H NMR (DMSO—$d_6$): δ9.26 (br s, 2H), 8.03 (d, 4H, J=8.5 Hz), 7.97 (d, 4H, J=8.5 Hz), 7.26 (d, 4H, J=8.8 Hz), 6.94 (d, 4H, J=8.5 Hz), 4.42 (d, 4H, J=5.8 Hz), 4.27 (s, 4H).

EXAMPLE 39

1,2-Bis-{4-[(3-cyano-benzenecarbonylamino)-methyl]-phenoxyl}-ethane (Formula (Ib), n=2)

The noted compound was prepared according to the procedure of Example 28 using 3-cyanobenzoyl chloride and the bis-benzyl amine of Example 13 to provide the desired bis-amide as a white solid (72% yield).

$^1$H NMR (DMSO—$d_6$): δ9.20 (t, 2H, J=5.6 Hz), 8.30 (s, 2H), 8.19 (d, 2H, J=8.0 Hz), 8.02 (d, 2H, J=7.8 Hz), 7.71 (t, 2H, J=7.8 Hz), 7.27 (d, 4H, J=8.5 Hz), 6.95 (d, 4H, J=8.5 Hz), 4.43 (d, 4H, J=5.8 Hz), 4.28 (s, 4H).

EXAMPLE 40

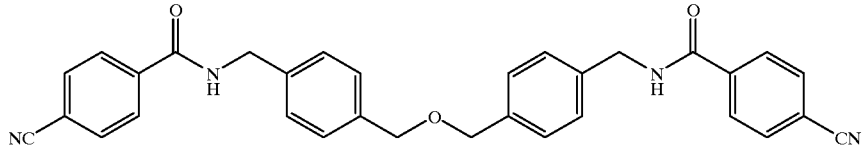

1,3-Bis-{4-[(3-cyano-benzenecarbonylamino)-methyl]-phenyl}-2-oxapropane

The noted compound was prepared according to the procedure outlined in Example 28 using the bis-benzylamine of Example 14 and 4-cyanobenzoyl chloride to provide the desired bis-amide as a light yellow solid (49% yield).

LRMS (positive electrospray) m/z: 532.0 (M+18).

LRMS (negative electrospray) m/z: 513.2 (M−1).

$^1$H NMR (DMSO—$d_6$): δ9.31 (br s, 2H), 8.04 (d, 4H, J=8.3 Hz), 7.98 (d, 4H, J=8.5 Hz), 7.31 (s, 8H), 4.50—4.49 (c, 8H).

PREPARATION OF BIS-AMIDINE COMPOUNDS

The synthesis of the bis-amidine compounds of Formula (I), that is, compounds of Formula (Ie):

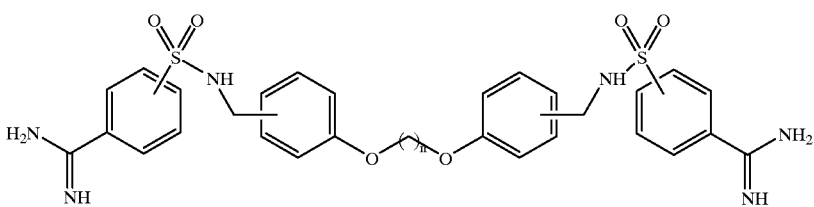

is exemplified by the following general procedure which is provided in detail in Example 41 in which n is 5:

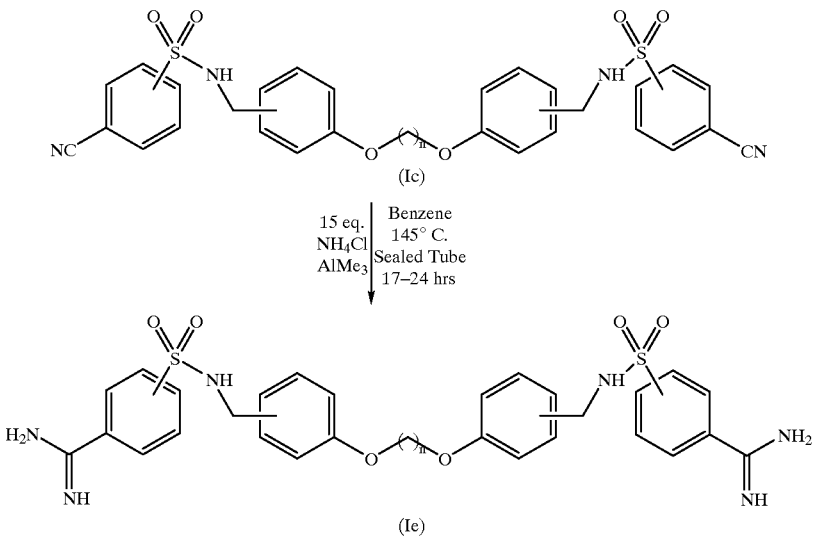

EXAMPLE 41

1,5-Bis-{4-[(3-carbamimidoyl-benzenesulfonylamino)-methyl]-phenoxy}-pentane (Formula (Ie), n=5)

The bis-amidino compounds of Formula (Ie) are prepared using a modified Weinreb reaction. See, e.g., Garigipati, Tetrahedron Lett. 31(14) 1969 (1990); Sidler et al., J.Org.Chem. 59 1231 (1994); Levin et al. Synth. Commun. 12(13) 989 (1982).

Preparation of Weinreb Reagent:

To a vigorously stirred suspension of anhydrous ammonium chloride (1.33 g; 25 mmol) in dry benzene (100 mL) was slowly added a solution of trimethyl aluminum (12.5 mL of 2.0 M solution in toluene; 25 mmol) dropwise via syringe at room temperature under an argon atmosphere. (Caution: vigorous methane gas evolution.] The resulting clear solution was then allowed to stir at room temperature for 45 minutes while gas evolution eventually diminished.

To this stirred solution is added the bis-nitrile sulfonamide of Example 20 (1.6 g; 2.5 mmol) and the resulting mixture is stirred for 30 minutes then transferred to a thick walled pressure tube equipped with a magnetic stirring bar and capped. The closed system is then carefully heated with stirring behind a blast shield in an oil bath to 150° C. for 24 hours. The reaction is then allowed to cool and then quenched with the careful addition of silica gel (~50 g) followed by a 1:1 mixture of chloroform and methanol (250 mL). The resulting mixture is stirred at room temperature for one hour then filtered through a coarse glass frit with suction (the residue is washed with methanol, ~50 mL). The combined filtrates are concentrated in vacuo to provide the crude bis-amidine, some mono-amidine by-product and ammonium chloride (~2.6 g). These solids are washed with chloroform (3×100 mL), hot acetonitrile (250 mL) and water (3×5 mL) on a medium glass frit with suction. The residue is dissolved in methanol and concentrated in vacuo to provide the desired bis-amidine as a tan solid (1.25 g; 74%).

LRMS (electrospray) m/z: 340 (M/2+1).

MALDI m/z: 679.95 (M+1).

$^1$H NMR (DMSO—d$_6$): δ9.58 (br s, 3H), 9.30 (br s, 3H), 8.30 (t, 2H, J=6.1 Hz), 8.21 (s, 2H), 8.09 (d, 2H, J=8.0 Hz), 8.05 (d, 2H, J =7.8 Hz), 7.82 (t, 2H, J=7.8 Hz), 7.13 (d, 4H, J=8.5 Hz), 6.83 (d, 4H, J=8.5 Hz), 3.95 (t, 8H, J=5.6 Hz), 1.76 (c, 4H), 1.55 (c, 2H).

EXAMPLE 42

1,5-Bis-{4-[(4-carbamimidoyl-benzenesulfonylamino)-methyl]-phenoxy}-pentane (Formula (Ie), n=5)

The noted compound was prepared according to the general procedure described in Example 41 using the bis-para-nitrile sulfonamide of Example 19 to provide the desired bis-amidine compound as a white solid (25% yield).

LRMS (electrospray) m/z: 340 (M/2+1).

MALDI m/z: 679.54 (M+1).

$^1$H NMR (CD$_3$OD): δ8.04 (d, 4H, J=8.0 Hz), 7.93 (d, 4H, J=8.5 Hz), 7.12 (d, 4H, J=8.5 Hz), 6.81 (d, 4H, J=8.5 Hz), 4.07 (s, 4H), 3.97 (t, 4H, J=6.3 Hz), 1.82 (c, 4H), 1. 65 (c, 2H).

EXAMPLE 43

1,6-Bis-{4-[(3-carbamimidoyl-benzenesulfonylamino)-methyl]-phenoxy}-hexane (Formula (Ie), n=6)

The noted compound was prepared according to the general procedure outlined in Example 41 using the bis-meta-nitrile sulfonamide of Example 18 to provide the desired bis-amidine as a white solid (69% yield).

LRMS (electrospray) m/z: 347 (M/2+1).

MALDI m/z: 693.32 (M+1).

$^1$H NMR (DMSO—$d_6$): δ9.55 (br s, 3H), 9.21 (br s, 3H), 8.32 (t, 2H, J=6.2 Hz), 8.18 (s, 2H), 8.09 (d, 2H, J=7.8 Hz), 8.03 (d, 2H, J=7.8 Hz), 7.83 (t, 2H, J=7.9 Hz), 7.13 (d, 4H, J=8.5 Hz), 6.82 (d, 4H, J=8.5 Hz), 3.95—3.91 (m, 8H), 1.70 (c, 4H), 1.46 (c, 4H).

EXAMPLE 44

1,6-Bis-{4-[(4-carbamimidoyl-benzenesulfonylamino)-methyl]-phenoxy}-hexane (Formula (Ie), n=6)

The noted compounds was prepared according to the general procedure outlined in Example 41 using the bis-para-nitrile sulfonamide of Example 17 to provide the desired bis-amidine as a white solid (64% yield).

LRMS (electrospray) m/z: 347 (M/2+1).

MALDI m/z: 693.60 (M+1).

$^1$H NMR (DMSO—$d_6$): δ9.48 (br s, 3H), 9.27 (br s, 3H), 7.99 (d, 4H, J=8.5 Hz), 7.96 (d, 4H, J=8.8 Hz), 7.13 (d, 4H, J=8.5 Hz), 6.83 (d, 4H, J=8.3 Hz), 3.94—3.89 (m, 8H), 1.71 (c, 4H), 1.45 (c, 4H).

EXAMPLE 45

1,7-Bis-{4-[(3-carbamimidoyl-benzenesulfonylamino)-methyl]-phenoxy}-heptane (Formula (Ie), n=7)

The noted compound was prepared according to the general procedure outlined in Example 41 using the bis-meta-nitrile sulfonamide of Example 16 to provide the desired bis-amidine as a white solid (99% yield).

LRMS (electrospray) m/z: 354.2 (M/2+1).

MALDI m/z: 707.46 (M+1).

$^1$H NMR (DMSO—d6): δ8.17 (s, 2H), 8.10 (d, 2H, J=7.5 Hz), 8.03 (d, 2H, J=7.8 Hz), 7.84 (t, 2H, J=7.8 Hz), 7.13 (d, 4H, J=8.0 Hz), 6.83 (d, 4H, J=8.5 Hz), 3.94—3.88 (c, 8H), 1.70 (m, 4H), 1.40 (m, 6H).

EXAMPLE 46

1,7-Bis-{4-[(4 -carbamimidoyl-benzenesulfonylamino)-methyl]-phenoxy}-heptane (Formula (Ie), n=7)

The noted compound was prepared according to the procedure of Example 41 using the bis-para-nitrile sulfonamide of Example 15 to provide the desired bis-amidine as a white solid (30% yield).

LRMS (electrospray) m/z: 354 (M/2+1).

MALDI m/z: 707.80 (M+1).

$^1$H NMR (CD$_3$OD): δ8.01 (d, 4H, J=7.8 Hz), 7.95 (d, 4H, J=7.8 Hz), 7.10 (d, 4H, J=7.8 Hz), 6.77 (d, 4H, J=7.5 Hz), 4.07 (s, 4H), 3.93 (t, 4H, J=6.3 Hz), 1.77 (c, 4H), 1. 47 (C, 6H).

EXAMPLE 47

1,4-Bis-{4-[(3-carbamimidoyl-benzenesulfonylamino)-methyl]-phenoxy}-butane (Formula (Ie), n=4)

The noted compound was prepared according to the procedure of Example 41 using the bis-meta-nitrile sulfonamide of Example 22 to provide the desired bis-amidine as a yellow solid (28% yield).

LRMS (electrospray) m/z: 333 (M/2+1).

MALDI m/z: 665.25 (M+1).

$^1$H NMR (DMSO—$d_6$): δ9.52 (br s, 3H), 9.11 (br s, 3H), 8.31 (t, 2H, J=4.3 Hz), 8.17 (s, 2H), 8.10 (d, 2H, J=8.5 Hz), 8.02 (d, 2H, J=7.8 Hz), 7.84 (t, 2H, J=7.2 Hz), 7.14 (d, 4H, J=8.5 Hz), 6.85 (d, 4H, J=8.8 Hz), 3.99—3.93 (m, 8H), 1.84 (c, 4H).

EXAMPLE 48

1,4-Bis-{4-[(4-carbamimidoyl-benzenesulfonylamino)-methyl]-phenoxy}-butane (Formula (Ie), n=4)

The noted compound was prepared according to the procedure of Example 41 using the bis-para-nitrile sulfonamide of Example 21 to provide the desired bis-amidine as a yellow solid (56% yield).

LRMS (electrospray) m/z: 333 (M/2+1).

MALDI m/z: 665.99 (M+1).

$^1$H NMR (DMSO—$d_6$): δ9.50 (br S, 3H), 9.20 (br s, 3H),8.40 (t, 2H, J=7.7 Hz), 7.99 (d, 4H, J=8.0 Hz), 7.96 (d, 4H, J=9.0 Hz), 7.14 (d, 4H, J=8.5 Hz), 6.85 (d, 4H, J=8.0 Hz), 3.99—3.93 (m, 8H), 1.84 (c, 4H).

EXAMPLE 49

3,1-Bis-{4-[(3-carbamimidoyl-benzenesulfonylamino)-methyl]-phenoxy}-propane (Formula (Ie), n=3)

The noted compound was prepared according to the procedure of Example 41 using the bis-meta-nitrile sulfonamide of Example 24 to provide the desired bis-amidine as a yellow solid (95% yield).

LRMS (electrospray) m/z: 326 (M/2+1).

MALDI m/z: 651.41 (M+1).

$^1$H NMR (DMSO—$d_6$): δ9.49 (br s, 3H), 9.26 (br s, 3H), 8.28 (br s, 2H), 8.19 (s, 2H), 8.10 (d, 2H, J=7.8 Hz), 8.06 (d, 2H, J=7.8 Hz), 7.83 (t, 2H, J=8.0 Hz), 7.14 (d, 4H, J=8.5 Hz), 6.86 (d, 4H, J=8.5 Hz), 4.09 (t, 4H, J=6.1 Hz), 3.96 (s, 4H), 2.16 (c, 2H).

EXAMPLE 50

1,3-Bis-{4-[(4-carbamimidoyl-benzenesulfonylamino)-methyl]-phenoxy}-propane (Formula (Ie), n=3)

The noted compound was prepared according to the general procedure provided in Example 41 using the bis-para-nitrile sulfonamide of Example 23 to provide the desired bis-amidine as a yellow solid (95% yield).

LRMS (electrospray) m/z: 326 (M/2+1).

MALDI m/z: 651.44 (M+1).

$^1$H NMR (DMSO—$d_6$ & $CD_3OD$): δ7.71 (d, 4H, J=8.3 Hz), 7.66 (d, 4H, J=8.5 Hz), 6.80 (d, 4H, J=8.5 Hz), 6.51 (d, 4H, J=8.5 Hz), 3.81—3.73 (m, 8H), 1.87 (c, 2H).

EXAMPLE 51

1,2-Bis-{4-[(3-carbamimidoyl-benzenesulfonylamino)-methyl]-phenoxy}-ethane (Formula (Ie), n=2)

The noted compound was prepared according to the procedure of Example 41 using the bis-meta-nitrile sulfonamide of Example 26 to provide the desired bis-amidine as a yellow solid (58% yield).

LRMS (electrospray) m/z: 319.2 (M/2+1), 637.0 (M+1).

MALDI m/z: 637.26 (M+1).

$^1$H NMR (DMSO—$d_6$): δ9.55 (br s, 3H), 9.18 (br s, 3H), 8.34 (t, 2H, J=6.4 Hz), 8.18 (s, 2H), 8.10 (d, 2H, J=7.0 Hz), 8.03 (d, 2H, J=6.8 Hz), 7.84 (t, 2H, J=7.8 Hz), 7.16 (d, 4H, J=8.5 Hz), 6.89 (d, 4H, J=8.5 Hz), 4.26 (s, 4H), 3.96 (d, 4H, J=6.0 Hz).

EXAMPLE 52

1,2-Bis-{4-[(4-carbamimidoyl-benzenesulfonylamino)-methyl]-phenoxy}-ethane (Formula (Ie), n=2)

The noted compound was prepared according to the general procedure described in Example 41 using the bis-para-nitrile sulfonamide of Example 25 to provide, following reverse phase HPLC, the desired bis-amidine as a white solid (5% yield).

LRMS (electrospray) m/z: 319.3 (M/2+1), 637.1 (M+1).

MALDI m/z: 636.91 (M+1).

$^1$H NMR ($CD_3OD$): δ8.01 (d, 4H, J=7.3 Hz), 7.95 (d, 4H, J=8.3 Hz), 7.13 (d, 4H, J=7.3 Hz), 6.87 (d, 4H, J=8.3 Hz), 4.26 (d, 4H, J=7.3 Hz), 4.07 (d, 4H, J=5.5 Hz). $^{13}$C NMR ($CD_3OD$): δ165.0, 157.1, 144.9, 130.6, 128.2, 127.8, 127.3, 126.2, 113.0, 65.3.

EXAMPLE 53

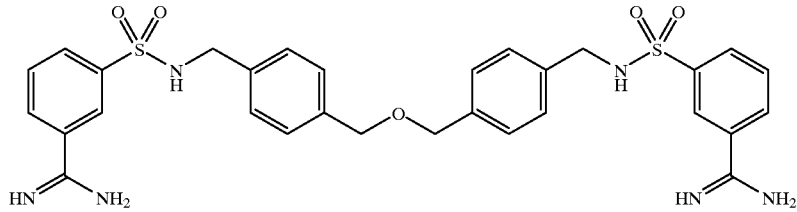

1,3-Bis-{4-[(3-carbamimidoyl-benzenesulfonylamino)-methyl]-phenyl}-2-oxapropane The noted compound was prepared according to the general procedure outlined in Example 41 using the bis-meta-nitrile sulfonamide of Example 27 to provide, following reverse phase chromatography, the desired bis-amidine as a white solid (25% yield).

LRMS (positive electrospray) m/z: 311.2 (M/2+1), 621.2 (M+1).

MALDI m/z: 620.98 (M+1).

$^1$H NMR ($CD_3OD$): δ7.48 (t, 2H, J=1.5 Hz), 7.45 (d, 2H, J=8.5 Hz), 7.26 (d, 2H, J=7.8 Hz), 7.06 (t, 2H, J=7.9 Hz), 6.57—6.52 (c, 8H), 3.80 (s, 4H), 3.47 (s, 4H). $^{13}$C NMR ($CD_3OD$): δ167.4, 143.9, 138.7, 138.0, 133.0, 132.6, 131.5, 130.6, 129.2, 129.1, 127.5, 72.9, 47.6.

The synthesis of the carbonylamino derivatives of Formula (I) were prepared in a manner analogous to the procedure described in Example 41 for the sulfonylamino derivatives. In particular, the synthesis of the bis-amidine compounds of Formula (If):

(If)

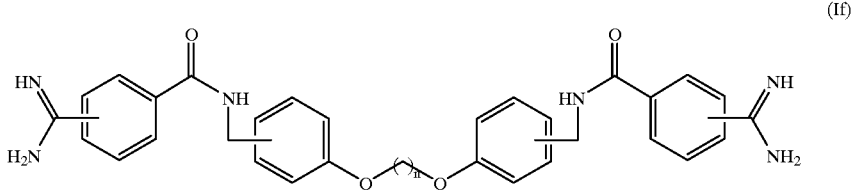

is exemplified by the following general procedure which is provided in detail in Example 54 in which n is 5:

para-nitrile amide of Example 32 to provide the desired bis-amidine (12% yield; 99.2% purity) as a white solid.

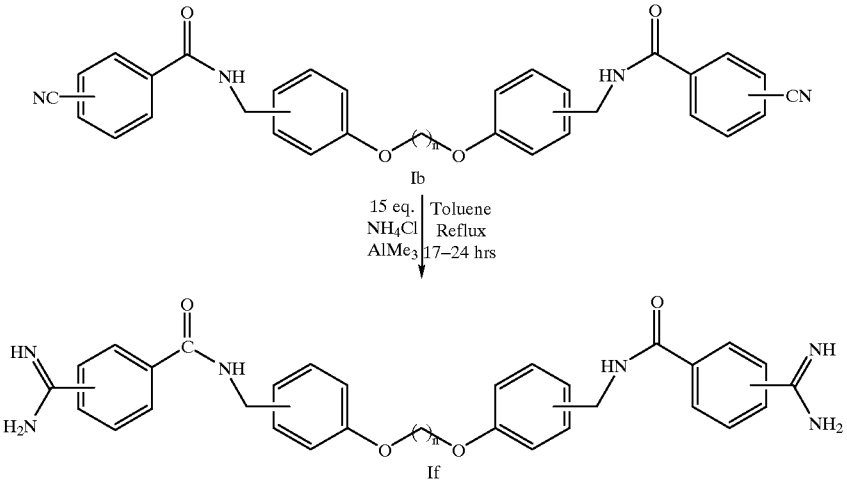

EXAMPLE 54

1,5-Bis-{4-[(4-carbamimidoyl-benzenecarbonylamino)-methyl]-phenoxy}-pentane (Formula (If), n=5)

The Weinreb reagent was prepared as described above in Example 41 using ammonium chloride and trimethylaluminum in anhydrous toluene (instead of benzene). The bis-para-nitrile amide of Example 34 (100 mg, 0.1667 mmol) was added and the solution was refluxed for 16 hours. The mixture was added to a chloroform/silica gel slurry to quench the reaction. The mixture was stirred for 30 min., filtered, washed with 50:50 ethanol/chloroform and evaporated. The crude product mixture was purified by reverse phase HPLC to give 7.5 mg (10.3% yield, 99.9% purity) of the desired bis-amidine as a white solid.

LRMS (electrospray) m/z: 304 (M/2+1); 607 (M+1).
MALDI m/z: 607.24 (M+1).
$^1$H NMR (CD$_3$OD): δ8.03 (d, 4H, J=8.0 Hz), 7.87 (d, 4H, J=8.5 Hz), 7.26 (d, 4H, J=8.5 Hz), 6.87 (d, 4H, J=8.5 Hz), 4.51 (s, 4H), 3.97 (t, 4H, J=6.0 Hz), 1.81 (m, 4H), 1.62 (m, 2H).

EXAMPLE 55

1,5-Bis-{4-[(3-carbamimidoyl-benzenecarbonylamino)-methyl]-phenoxy}-pentane (Formula (If), n=5)

The noted compound was prepared according to the procedure outlined in Example 54 using the bis-meta-nitrile amide of Example 35 to provide the desired bis-amidine as a white solid (13% yield; 99.2% purity).

LRMS (electrospray) m/z: 304 (M/2+1); 607 (M+1).
MALDI m/z: 607.56 (M+1).
$^1$H NMR (CD$_3$OD): δ8.27 (d, 2H, J=2.0 Hz)), 8.17 (dd, 2H, J=8.0, 1.0 Hz), 7.93 (d, 2H, J=7.6 Hz), 7.70 (t, 2H, J=7.0 Hz), 7.27 (d, 4H, J=8.6 Hz), 6.87 ( d, 4H, J=8.5 Hz), 4.51 (s, 4H), 3.97 (t, 4H, J=6.0 Hz), 1.82 (m, 4H) , 1.63 (m, 2H)

EXAMPLE 56

1,6-Bis-{4-[(4-carbamimidoyl-benzenecarbonylamino)-methyl]-phenoxy}-hexane (Formula (If), n=6)

The noted compound was prepared according to the general procedure provided in Example 54 using the bis- LRMS (electrospray) m/z: 311 (M/2+1).
MALDI m/z: 621.24 (M+1).
$^1$H NMR (DMSO—d$_6$): δ9.39 (br s ), 9.20 (br s , 2H), 9.09 (br s), 8.08 (d, 4H, J=8.5 Hz), 7.90 (d, 4H, J=8.5 Hz), 7.25 (d, 4H, T=8.5 Hz), 6.89 (d, 4H, J=8.5 Hz), 4.44 (d, 4H, J=4.5 Hz), 3.95 (t, 4H, J=6.0 Hz), 1.71 (m, 4H), 1.46 (m, 4H).

EXAMPLE 57

1,6-Bis-{4-[(3-carbamimidoyl-benzenecarbonylamino)-methyl]-phenoxy}-hexane (Formula (If), n=6)

The noted compound was prepared according to the procedure of Example 54 using the bis-meta-nitrile amide of Example 33 to provide the desired bis-amidine as a white solid (23% yield; 99.9% purity).

LRMS (electrospray) m/z: 311 (M/2+1); 621 (M+1)
MALDI m/z: 621.05(M+1).
$^1$H NMR (CD$_3$OD): δ8.32 (s, 2H), 8.23 (d, 2H, J=7.5 Hz), 7.98 (d, 2H, J=7.6 Hz), 7.76 (t, 2H, J=7.6 Hz), 7.32 (d, 4H, J=8.0 Hz), 6.92 (d, 4H, J=8.0 Hz), 4.57 (s, 4H), 4.01 (t, 4H, J=6.6 Hz), 1.82 (m, 4H), 1.58 (m, 4H).

EXAMPLE 58

1,7-Bis-{4-[(4-carbamimidoyl-benzenecarbonylamino)-methyl]-phenoxy}-heptane (Formula (If), n=7)

The noted compound was prepared according to the procedure of Example 54 using the bis-para-nitrile amide of Example 30 to provide the desired bis-amidine (12% yield; 98% purity) as a white solid.

LRMS (electrospray) m/z: 318 (M/2+1); 635 (M+1)
MALDI m/z: 635.53 (M+1).
$^1$H NMR (CD$_3$OD): δ8.03 (d, 4H, J=8.0 Hz), 7.87 (d, 4H, J=8.0 Hz), 7.26 (d, 4H, J=8.5 Hz), 6.86 (d, 4H, J=8.5 Hz), 4.51 (s, 4H), 3.96 (t, 4H, J=6.5 Hz), 1.77 (m, 4H), 1.51 (m, 6H).

EXAMPLE 59

1,7-Bis-{4-[(3-carbamimidoyl-benzenecarbonylamino)-methyl]-phenoxy}-heptane (Formula (If), n=7)

The noted compound was prepared according to the procedure of Example 54 using the bis-meta-nitrile amide of Example 31 to provide the desired bis-amidine as a white solid (7% yield, 99.9% purity).

LRMS (electrospray) m/z: 318 (M/2+1); 635 (M+1).

MALDI m/z: 635.26 (M+1).

$^1$H NMR (CD$_3$OD): δ8.27 (s, 2H), 8.18 (d, 2H, J=8.0 Hz), 7.93 (d, 2H, J=8.0 Hz), 7.71 (t, 2H, J=8.0 Hz), 7.27 (d, 4H, J=8.4 Hz), 6.86 (d, 4H, J=8.4 Hz), 3.94 (t, 4H, J=6.5 Hz), 1.76 (m, 4H), 1.48 (m, 6H).

EXAMPLE 60

1,4-Bis-{4-[(4-carbamimidoyl-benzenecarbonylamino)-methyl]-phenoxy}-butane (Formula (If), n=4)

The noted compound was prepared according to the general procedure of Example 54 using the bis-para-nitrile amide of Example 36 to provide the desired bis-amidine (18% yield; 99.6% purity) as a white solid.

LRMS (electrospray) m/z: 297(M/2+1); 593 (M+1).

$^1$H NMR (CD$_3$OD): δ8.04 (d, 4H, J=6.0 Hz), 7.88 (d, 4H, J=6.0 Hz), 7.27 (d, 4H, J=8.0 Hz), 6.88 (d, 4H, J=8.0 Hz), 4.51 (s, 4H), 4.02 (br s , 4H), 1.93 (br s , 4H).

EXAMPLE 61

1,4-Bis-{4-[(3-carbamimidoyl-benzenecarbonylamino)-methyl]-phenoxy}-butane (Formula (If), n=4)

The noted compound was prepared according to the general procedure outlined in Example 54 using the bis-meta-nitrile amide of Example 37 to provide the bis-amidine as a white solid (5% yield; 99.9% purity).

LRMS (electrospray) m/z: 297 (M/2+1); 593 (M+1).

$^1$H NMR (DMSO—d$_6$): δ9.38 (br, s), 9.08 (t, 2H, J=6.5 Hz), 8.27 (s, 2H), 8.19 (d, 2H, J=7.6 Hz), 7.92 (d, 2H, J=8.0 Hz), 7.73 (t, 2H, J=8.0 Hz), 7.25 (d, 4H, J=8.5 Hz), 6.89 (d, 4H, J=8.5 Hz), 4.43 (d, 4H, J=6.5 Hz), 3.99 (br s, 4H), 1.83 (m, 4H).

EXAMPLE 62

1,3-Bis-{4-[(4-carbamimidoyl-benzoylamino)-methyl]-phenoxy}-propane (Formula (If), n=3)

The noted compound was prepared according to the procedure described in Example 54 using the bis-para-nitrile amide of Example 29 to provide the desired bis-amidine as a yellow solid (25% yield).

LRMS (electrospray) m/z: 290 (M/2+1).

MALDI m/z: 578.97 (M+1).

$^1$H NMR (DMSO—d$_6$): δ9.25 (br s, 2H), 8.08 (d, 4H, J=8.3 Hz), 7.91 (d, 4H, J=8.3 Hz), 7.25 (d, 4H, J=8.8 Hz), 6.91 (d, 4H, J=8.5 Hz), 4.43 (d, 4H, J=5.3 Hz), 4.11 (t, 4H, J=6.4 Hz), 2.14 (c, 2H).

EXAMPLE 63

1,3-Bis-{4-[(3-carbamimidoyl-benzoylamino)-methyl]-phenoxy}-propane (Formula (If), n=3)

The noted compound was prepared according to the procedure described in Example 54 using the bis-meta-nitrile amide of Example 28 to provide the desired bis-amidine as a white solid (41% yield).

LRMS (electrospray) m/z: 290 (M/2+1).

MALDI m/z: 579.40 (M+1).

$^1$H NMR (DMSO—d$_6$): δ 9.27 (br s, 2H) 8.42 (s, 2H), 8.19 (s, 2H), 8.20 (d, 2H, J=7.8 Hz), 7.97 (d, 2H, J=7.8 Hz), 7.72 (t, 2H, J=7.8 Hz), 7.27 (d, 4H, J=8.5 Hz), 6.91 (d, 4H, J=8.5 Hz), 4.42 (s, 4H), 4.11 (c, 4H), 2.14 (c, 2H).

EXAMPLE 64

1,2-Bis-{4-[(4-carbamimidoyl-benzoylamino)-methyl]-phenoxy}-ethane (Formula (If), n=2)

The noted compound was prepared according to the general procedure of Example 54 using the bis-para-nitrile amide prepared according to Example 38 to provide, following reverse phase HPLC, the desired bis-amidine as a white solid (18% yield).

LRMS (electrospray) m/z: 283.2 (M/2+1), 564.9 (M+1).

MALDI m/z: 565.69 (M+1).

$^1$H NMR (DMSO—d$_6$) δ9.40 (br s, 3H), 9.26 (t, 2H, J=4.6 Hz), 9.06 (br s, 3H), 8.07 (d, 4H, J=8.3 Hz), 7.89 (d, 4H, J=8.3 Hz), 7.27 (d, 4H, J=8.8 Hz), 6.95 (d, 4H, J=8.3 Hz), 4.44 (d, 4H, J=5.8 Hz), 4.28 (s, 4H).

EXAMPLE 65

1,2-Bis-{4-[(3-carbamimidoyl-benzoylamino)-methyl]-phenoxy}-ethane (Formula (If), n=2)

The indicated compound was prepared according to the procedure of Example 54 using the bis-meta-nitrile amide prepared according to Example 39 to provide, following reverse phase HPLC, the desired bis-amidine as a white solid (9% yield).

LRMS (electrospray) m/z: 283.2 (M/2+1), 565.2 (M+1).

MALDI m/z: 565.32 (M+1).

$^1$H NMR (DMSO—d$_6$): δ9.39 (br s, 2H) 9.18 (t, 2H, J=5.9 Hz), 9.05 (br s, 3H), 8.29 (s, 2H), 8.21 (d, 2H, J=8.0 Hz), 7.93 (d, 2H, J=8.5 Hz), 7.74 (t, 2H, J=7.8 Hz), 7.28 {d, 4H, J=8.8 Hz), 6.95 (d, 4H, J=8.8 Hz), 4.45 (d, 4H, J=5.8 Hz), 4.28 (s, 4H).

EXAMPLE 66

1,3-Bis-{4-[(4-carbamimidoyl-benzenecarbonylamino)-methyl]-phenyl}-2-oxapropane

The indicated compound was prepared according to the procedure of Example 54 using the bis-para-nitrile amide prepared according to Example 40 to provide, following reverse phase chromatography, the desired bis-amidine as a white solid (4% yield).

LRMS (positive electrospray) m/z: 275.4 (M/2+1), 549.0 (M+1).

MALDI m/z: 549.67 (M+1).

$^1$H NMR (CD$_3$OD): δ8.08 (d, 4H, J=8.3 Hz) , 7.91 (d, 4H, J=8.3 Hz), 7.38—7.36 (c, 8H), 4.62 (s, 4H),4.55 (s, 4H).

The N-methylsulfonylamino derivatives of the invention are prepared according to the following general scheme outlined in Examples 67 and 68 wherein n of Formula (Ig) and Formula (Ih) is 3:

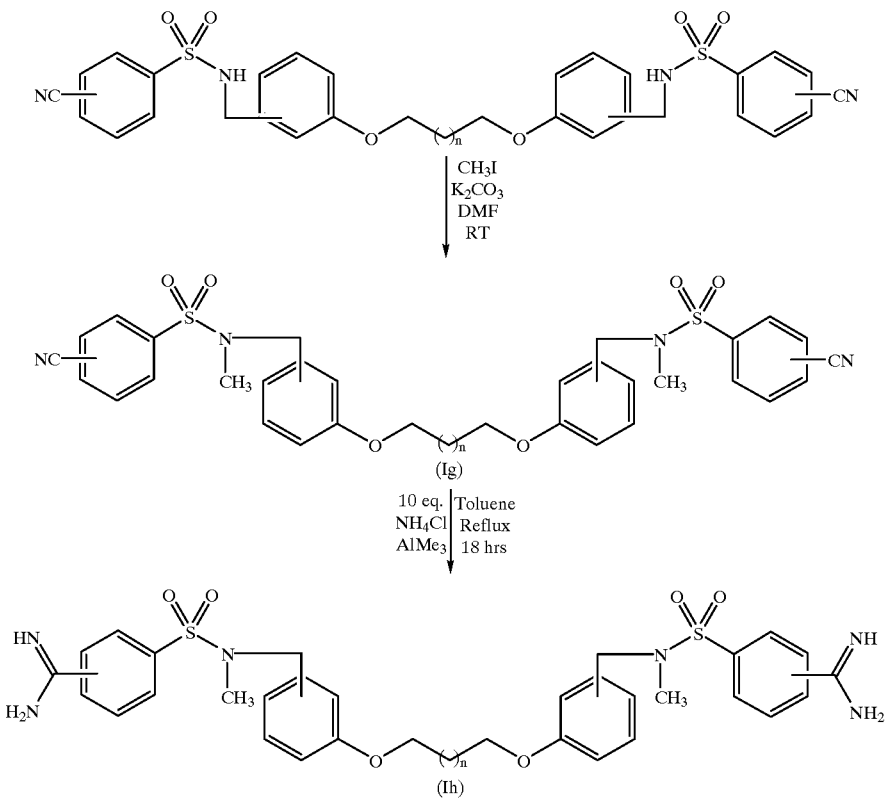

EXAMPLE 67

1,3-Bis-{4-[(3-cyano-benzenesulfonyl-[N-methyl]-amino)-methyl]-phenoxy}-propane (Formula (Ia), n=3)

To a vigorously stirred solution of compound prepared according to Example 24 (0.22 g; 0.36 mmol) in dry dimethylformamide (5 mL) was added finely powdered potassium carbonate (0.49 g; 3.6 mmol) and iodomethane (0.06 mL; 0.96 mmol) at room temperature under an argon atmosphere. The resulting mixture was allowed to stir for 72 hours. The reaction was diluted with ether (50 mL), filtered and washed with water (2×20 mL) and brine (30 mL). The organic layer was then dried (MgSO$_4$), filtered and concentrated in vacuo to provide the crude N-methyl product (~0.17 g). Purification by flash chromatography on silica gel with 50% hexanes in ethyl acetate eluent provided the desired product as a white solid (0.14 g; 46% yield).

$^1$H NMR (CDCl$_3$): δ8.10 (t, 2H, J=1.4 Hz), 8.06 (dt, 2H, J=1.4, 8.0 Hz), 7.90 (dt, 2H, J=1.3, 7.8 Hz), 7.72 (t, 2H, J=7.9 Hz), 7.21 (d, 4H, J=8.5 Hz), 6.89 (d, 4H, J=8.8 Hz), 4.19–4.15 (c, 8H), 2.66 (s, 6H), 2.29 (m, 2H).

EXAMPLE 68

1,3-Bis-{4-[(3-carbamimidoyl-benzenesulfonyl-[N-methyl]-amino)-methyl]-phenoxy}-propane (Formula (Ih), n=3)

The Weinreb reagent was prepared as described above in Example 41 using ammonium chloride and trimethylaluminum in anhydrous toluene (instead of benzene). The bis-nitrile sulfonamide from Example 67 (38 mg, 0.06 mmol) was added and the solution was refluxed for 20 hours. The reaction mixture was added to a methanol/chloroform/silica gel slurry to quench the reaction. The mixture was stirred for 30 min., filtered, washed with 50:50 methanol/chlororform and evaporated. The combined filtrates were concentrated in vacuo to provide the crude bis-amidine, and ammonium chloride. These solids are washed with chloroform (3×100 mL), hot acetonitrile (250 mL) and water (3×3 mL) on a medium glass frit with suction. The residue is dissolved in methanol and concentrated in vacuo to provide the desired bis-amidine as a white solid (37.8 mg; 94% yield).

LRMS (electrospray) m/z: 340.1 (M/2+1), 679.0 (M+1).

MALDI m/z: 679.413 (M+1).

$^1$H NMR (CD$_3$OD): δ8.24 (t, 2H, J=1.5 Hz), 8.20 (dt, 2H, J=7.3, 1.5 Hz), 8.11 (dt, 2H, J=7.8, 1.3 Hz), 7.90 (t, 2H, J=7.9 Hz), 7.25 (d, 4H, J=8.8 Hz), 6.93 (d, 4H, J=8.5 Hz), 4.20—4.16 (c, 8H), 2.67 (s, 6H), 2.29 (m, 2H).

The following scheme may be used to prepare compounds wherein the internal methylene portion ("bridging portion") of the Formula (I) compound is oriented in the meta-position relative to the sulfonamido- or amido- portion of molecule:

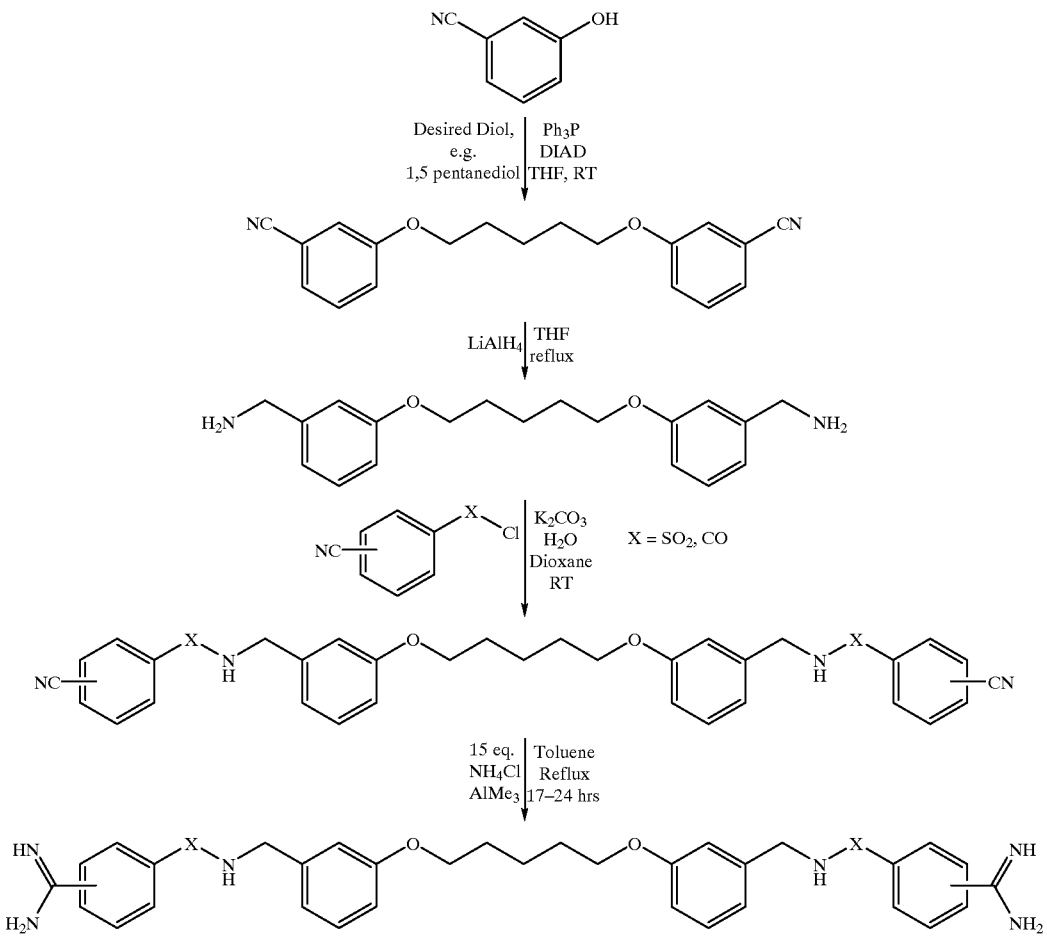

Details of this synthetic scheme are outlined in the procedures defined in Examples 69–77 wherein X is either —SO₂— or —C(O)—, as indicated.

EXAMPLE 69

A. 3,3'-Pentanediyldioxy-dibenzonitrile

The noted starting material in which n is 5 is prepared according to the above procedure described in Example 1 using 1,5-pentanediol and 3-cyanophenol to provide the pure diether as a white solid (62% yield).

¹H NMR (CDCl₃): δ7.36—7.08 (m, 8H), 3.98 (t, 4H, J=6.0 Hz), 1.86 (m, 4H), 1.65 (m, 2H).

B. 3-[5-(3-Aminomethyl-phenoxy)-pentyldioxy]-benzylamine

The noted compound is prepared according to the procedure of Example 8 using the dibenzonitrile prepared in paragraph A with lithium aluminum hydride to provide the diamine as a viscous liquid. The liquid was treated with HCl in diethyl ether and evaporated to dryness to give the amine hydrochloride salt as a white solid (1.3 g, 68% yield).

LRMS (electospray) m/z: 315 (M+1).

¹H NMR (DMSO—d₆) δ7.30 (t, 2H, J=8.0 Hz), 7.15 (d, 2H, J=2.0 Hz), 7.02 (d, 2H, J=8.0 Hz), 6.92 (dd, 2H, J=8.0, 2.0 Hz), 4.00 (t, 4H, J=6.5 Hz), 3.96 (m, 4H), 1.78 (m, 4H), 1.55 (m, 2H).

EXAMPLE 70

1,5-Bis-{3-[(4-cyano-benzenesulfonylamino)-methyl]-phenoxy}-pentane

The noted compound was prepared according to the procedure of Example 15 using the bis-benzylamine of Example 69 and 4-cyanobenzene sulfonyl chloride to provide the disulfonamide as a pale yellow solid (288 mg, 89% yield).

¹H NMR (DMSO—d₆): δ8.5 (s, 2H), 8.04 (d, 4H, J=8.4 Hz), 7.92 (d, 4, J=8.4 Hz), 7.18 (t, 2H, J=8.0 Hz), 6.80—6.73 (m, 6H), 4.06 (s, 4H), 3.92 (t, 4H, J=6.0 Hz), 1.76 (m, 4H), 1.60 (m, 2H).

EXAMPLE 71

1,5-Bis-{3-[(3-cyano-benzenesulfonylamino)-methyl]-phenoxy}-pentane

The noted compound is prepared according to the procedure of Example 15 using the bis-Benzylamine of Example 69 and 3-cyanobenzene sulfonyl chloride to provide the disulfonamide as a pale yellow solid (260 mg, 81% yield).

¹H NMR (DMSO—d₆): δ8.41 (s, 2H), 8.06 (s, 2H), 8.04 (d, 2H, J=8.0 Hz), 8.02 (d, 2H, J=8.0 Hz), 7.73 (t, 2H, J=8.0 Hz), 7.13 (t, 2H, J=8.0 Hz), 6.76—6.72 (m, 6H), 4.05 (s, 4H), 3.89 (t, 4H, J=6.0 Hz), 1.74 (m, 4H), 1.49 (m, 2H).

EXAMPLE 72

1,5-Bis-{3-[(4-cyano-benzenecarbonylamino)-methyl]-phenoxy}-pentane

The noted compound is prepared according to the procedure of Example 28 using 4-cyanobenzoyl chloride and the bis-benzylamine of Example 69 to provide the diamide as white solid (285 mg, 99% yield). $^1$H NMR (DMSO—d$_6$): δ9.32 (t, 2H, J=4 Hz), 8.06 (d, 4H, J=8.0 Hz), 7.96 (d, 4H, J=8.0 Hz), 7.19 (t, 2H, J=8.0 Hz), 6.86 (s, 2H), 6.85 (d, 2H, J=8.0 Hz), 6.77 (d, 2H, J=8.0), 4.43 (d, 4H, J=4.3 Hz), 3.92 (m, 4H), 1.72 (m, 4H), 1.50 (m, 2H).

EXAMPLE 73

1,5-Bis-{3-[(3-cyano-benzenecarbonylamino)-methyl]-phenoxy}-pentane

The noted compound is prepared according to the procedure described in Example 28 using 3-cyanobenzoyl chloride and the bis-benzylamine of Example 69 to provide the desired diamide as white solid (270. mg, 94% yield).

$^1$H NMR (DMSO—d$_6$): δ9.22 (t, 2H), 8.31 (s, 2H), 8.19 (d, 2H, J=8.0 Hz), 8.01 (d, 2H, J=8.0 Hz), 7.70 (t, 2H, J=8.0 Hz), 7.22 (t, 2H, J=8.0 Hz), 6.89—6.87 (m, 6H), 4.45 (d, 4H, J=5.4 Hz), 3.95 (t, 4H, J=6.0 Hz), 1.74 2 (m, 4H), 1.50 (m, 2H)).

EXAMPLE 74

1,5-Bis-{3-[(4-carbamimidoyl-benzenesulfonylamino)-methyl]-phenoxy}-pentane

The noted compounds is prepared according to the procedure described in Example 41 using the bis-para-nitrile sulfonamide of Example 70 to provide the desired bis-amidine, following purification by RP-HPLC, as a white solid (48% yield).

LRMS (electrospray) m/z: 340 (M/2+1).

$^1$H NMR (CD$_3$OD): δ8.06 (d, 4H, J=8.0 Hz), 7.96 (d, 4H, J=8.0 Hz), 7.16 (t, 2H, J=8.0 Hz), 6.82-6.77 (m, 6H), 4.11 (s, 4H), 3.97 (t, 4H, J=6.0 Hz), 1.85 (m, 4H), 1.66 (m, 2H).

EXAMPLE 75

1,5-Bis-{3[-(3-carbamimidoyl-benzenesulfonylamino)-methyl]-phenoxy}-pentane

The noted compound is prepared according to the procedure described in Example 41 using the bis-meta-nitrile sulfonamide prepared in Example 71 to provide the desired bis-amidine, following purification by RP-HPLC, as a white solid (44% yield).

LRMS (electrospray) m/z: 340 (M/2+1).

$^1$H NMR (CD$_3$OD): δ8.25–8.04 (m, 6H), 7.85 (t, 2H, J=8.0 Hz), 7.20 (t, 2H, J=8.0 Hz), 6.89–6.81 (m, 6H), 4.20 (s, 4H), 3.39 (br s, 4H), 1.90 (m, 4H), 1.71 (m, 2H).

EXAMPLE 76

1,5-Bis-{3-[(4-carbamimidoyl-benzenecarbonylamino)-methyl]-phenoxy}-pentane

The noted compound is prepared according to the procedure described in Example 54 using the bis-para-nitrile amide of Example 72 to provide the bis-amidine, following purification by RP-HPLC, as a white solid (29% yield).

LRMS (electrospray) mfz: 304(M/2+1); 607 (M+1).

$^1$H NMR (CD$_3$OD): 5 8.04 (d, 4H, J=8.0 Hz), 7.87 (d, 4H, J=8.0 Hz), 7.22 (t, 2H, J=8.0 Hz), 6.91–6.80 (m, 6H), 4.55 (s, 4H), 3.98 (t, 4H, J=6.0 Hz), 1.81 (m, 2H).

EXAMPLE 77

1,5-Bis-{3-[(3-carbamimidoyl-benzenecarbonylamino)-methyl]-phenoxy}-pentane

The noted compound is prepared according to the procedure described in Example 54 using the bis-meta-nitrile amide of Example 73 to provide the bis-amidine, following purification by RP-HPLC, as a white solid (32% yield).

LRMS (electrospray) m/z: 304(M/2+1); 607 (M+1).

$^1$H NMR (CD$_3$OD): δ8.30 (s, 2H), 8.20 (d, 2H, J=8.0 Hz), 7.95 (d, 2H, J=8.0 Hz), 7.73 (t, 2H, J=8.0 Hz), 7.24 (t, 2H, J=8.0 Hz), 6.93–6.81 (m, 6H), 4.00 (t, 4H, J=6.0 Hz), 1.83 (m, 4H), 1.65 (m, 2H).

Also contemplated within the scope of the present invention are those compounds of Formula (I) in which one portion of the molecule is asymmetric relative to the other portion of the molecule. That is, although preferred compounds of Formula (I) are symmetrical, this is not a requirement. The following non-limiting examples and synthetic procedures further illustrate this embodiment of the invention:

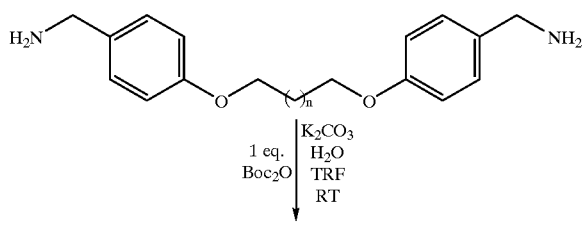

-continued

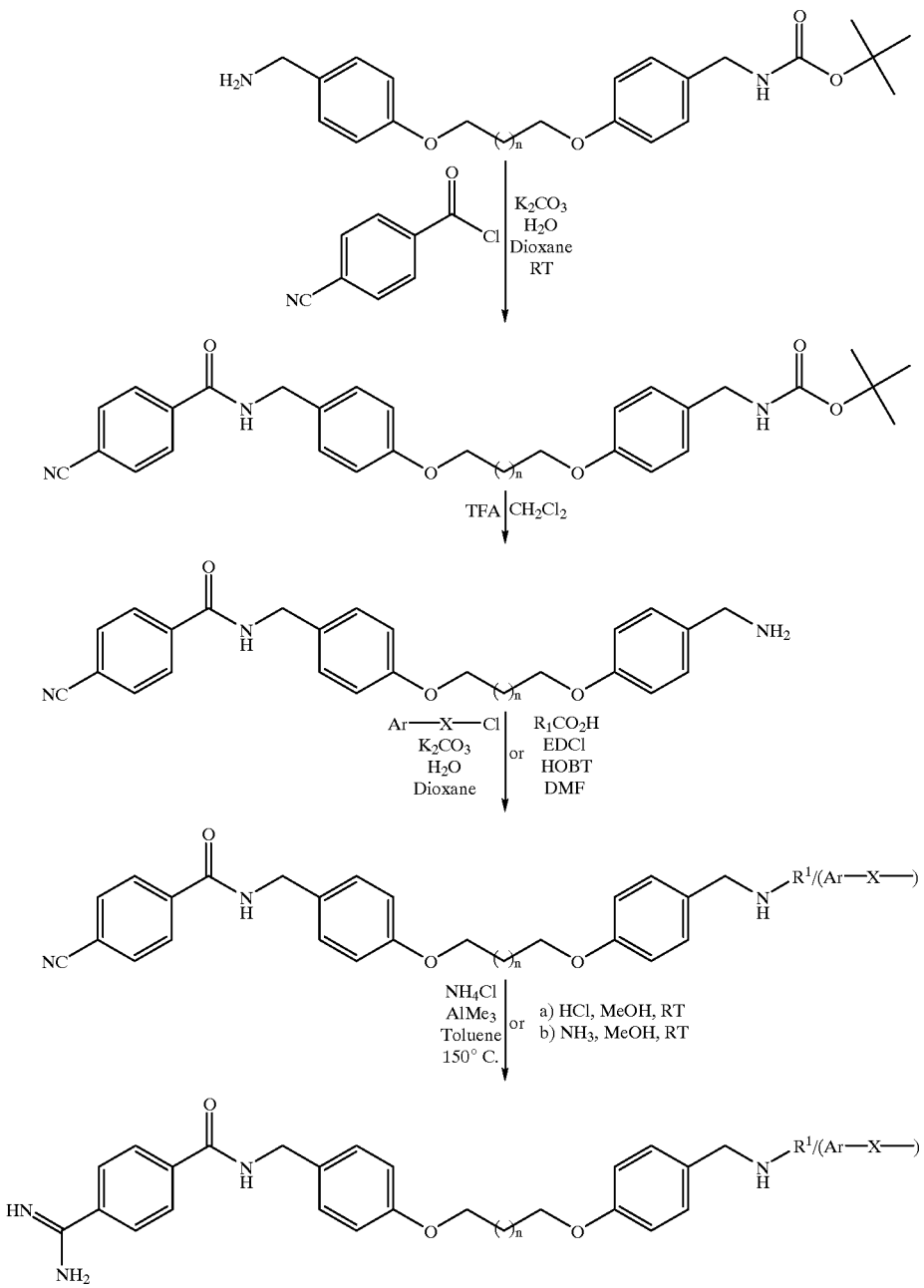

EXAMPLE 78

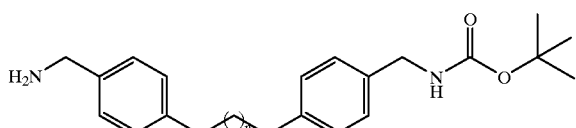

{4-[3-(4-aminomethyl-phenoxy)-propoxyl-benzyl}-carbamic acid tert-butyl ester (Formula (I), n=3)

To a suspension of 4-[3-(4-Aminomethyl-phenoxy)-propoxy]-benzylamine prepared in accordance with Example 12 (1.0 g; 3.49 mmol) in THF (70 mL) was added 10% aqueous potassium carbonate solution (9.70 mL; 6.98 mmol). Di-tert-butyl dicarbonate (0.76 g; 3.49 mmol) in 5 mL of THF was then added by syringe and the reaction mixture was stirred at room temperature for 20 hours. The reaction mixture was then diluted with EtOAc (100 mL) and washed with water (2×100 mL), dried over $MgSO_4$, and concentrated to the crude product. Purification by silica gel chromatography (dichloromethane to 8% MeOH/dichloromethane) afforded the noted product as a yellow solid (319 mg, 24% yield).

LRMS (electrospray) m/z: 387 (M+1)

$^1$H NMR ($CD_3OD$) : δ7.26 (d, 2H, J=8.53 Hz), 7.18 (d, 2H, J=8.03 Hz), 6.93 (d, 2H, J=8.53 Hz), 6.87 (d, 2H, J=8.54 Hz), 4.14–4.18 (m, 6H), 3.77 (s, 2H), 2.14–2.24 (m, 2H), 1.46 (s, 9H).

EXAMPLE 79

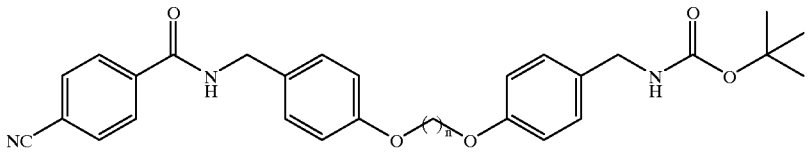

[4-(3-{4-(4-cyano-benzoylamino-methyl]-phenoxy}-propoxy)-benzyl]-carbamic acid tert-butyl ester (Formula (I), n=3)

To a suspension of {4-[3-(4-aminomethyl-phenoxy)-propoxy]-benzyl}-carbamic acid tert-butyl ester prepared in Example 78 (3.00 g, 7.76 mmol) in THF (30 mL) was added a 10% aqueous solution of potassium carbonate (53.90 mL, 38.81 mmol). 4-Cyanobenzoyl chloride (1.29 g, 7.76 mmol) was then added in one portion and the reaction mixture was stirred at room temperature for 16 hours. The mixture was then diluted with EtOAc (150 mL), washed with 1N aqueous HCl (2×150 mL), dried over $MgSO_4$, and concentrated to provide the desired compound as a yellow solid (2.41 g, 60% yield) which did not require any further purification.

LRMS (electrospray) m/z: 516 (M+1), 533 (M+18)

$^1$H NMR ($CDCl_3$) δ7.89 (d, 2H, J=8.53 Hz), 7.75 (d, 2H, J=8.53 Hz), 7.24 (m, 2H), 7.21 (d, 2H, J=8.42 Hz), 6.91 (d, 2H, J=8.53 Hz), 6.88 (d, 2H, J=8.53 Hz), 6.39 (br s, 1H), 4.79 (br s, 1H), 4.60 (d, 2H, J=5.53 Hz), 4.25 (d, 2H, J=4.51 Hz), 4.13–4.20 (m, 4H), 2.27 (m, 2H), 1.48 (s, 9H).

$^1$H NMR (DMSO-$d_6$): δ8.03 (d, 2H, J=8.53 Hz), 7.97 (d, 2H, J=8.53 Hz), 7.24 (d, 2H, J=8.53 Hz), 7.23 (d, 2H, J=8.53 Hz), 6.91 (d, 2H, J=8.54 Hz), 6.88 (d, 2H, J=8.54 Hz), 4.42 (d, 2H, J=4.02 Hz), 4.08–4.12 (m, 4H), 3.65 (s, 2H), 2.11–2.17 (m, 2H).

EXAMPLE 81

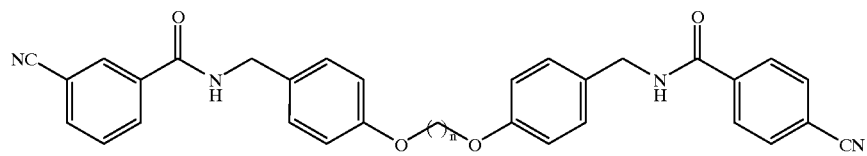

EXAMPLE 80

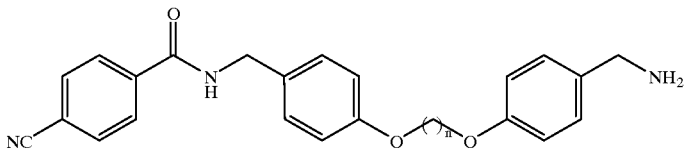

-{4-[3-(4-Aminomethyl-phenoxy)-propoxyl-benzyl}-4-cyano-benzamide (Formula (I), n=3)

To a suspension of [4-(3-{4-[(4-cyano-benzoylamino-methyl]-phenoxy}-propoxy)-benzyl]-carbamic acid tert-butyl ester (2.30 g, 4.46 mmol) of Example 79 in dichloromethane (75 mL) was added trifluoroacetic acid (75 mL). The resulting solution was stirred at room temperature for 15 minutes, and then concentrated under reduced pressure to an orange oil. This oil was taken up in EtOAc (100 mL) and washed twice with 10% aqueous potassium carbonate. The organics were dried over $MgSO_4$, and concentrated to provide the noted compound as a white solid. (725 mg, 40%).

LRMS (electrospray) m/z: 416 (M+1)

3-Cyanobenzoyl-{4-[3-(4-aminomethyl-phenoxy)-propoxyl-benzyl}-4-cyanobenzamide (Formula (I), n=3)

The noted compound is prepared according to the procedures previously described using N-{4-[3-(4-aminomethyl-phenoxy)-propoxy]-benzyl}- 4-cyano-benzamide of Example 80 and 3-cyanobenzoyl chloride to provide the asymmetrical bis-nitrile as a yellow solid (310 mg, 95%).

$^1$H NMR (DMSO-$d_6$): δ9.24 (t, 1H, J=6.02 Hz), 9.18 (t, 1H, J=6.02 Hz), 8.29–8.31 (m, 1H), 8.16–8.20 (im, 1H), 8.00–8.04 (m, 3H), 7.98 (d, 2H, J=8.53 Hz), 7.70 (t, 1H, J=8.03 Hz), 7.25 (d, 2H, J=8.54 Hz), 7.24 (d, 2H, J=8.54 Hz), 4.41 (m, 4H), 4.10 (t, 4H, J=6.02 Hz), 2.14 (m, 2H).

EXAMPLE 82

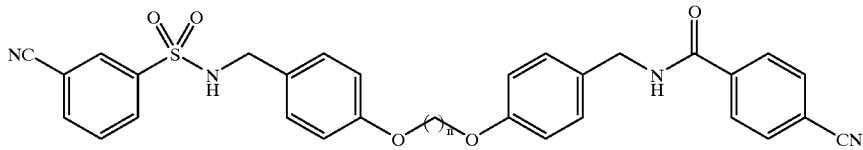

3-Cyanobenzene-sulfonyl-{4-(3-(4-aminomethyl-phenoxy)-propoxy]-benzyl}-4-cyanobenzamide (Formula (I), n=3)

The noted compound is prepared according to the procedures previously provided using N-{4-[3-(4-aminomethyl-phenoxy)-propoxy]-benzyl}-4-cyano-benzamide of Example 80 and 3-cyanobenzene sulfonyl chloride to provide the asymmetrical bis-nitrile as a yellow solid (300 mg, 86%).

LRMS (electrospray) m/z: 581 (M+1), 598 (M+18)

$^1$H NMR (DMSO-$d_6$): δ7.95–8.05 (m, 6H), 7.22–7.28 (m, 3H), 7.08 (d, 2H, J=8.53 Hz), 6.90–6.95 (m, 3H), 6.80 (d, 2H, J=8.53 Hz), 4.40–4.44 (m, 2H), 3.99–4.11 (m, 6H), 2.10–2.16 (m, 2H).

EXAMPLE 83

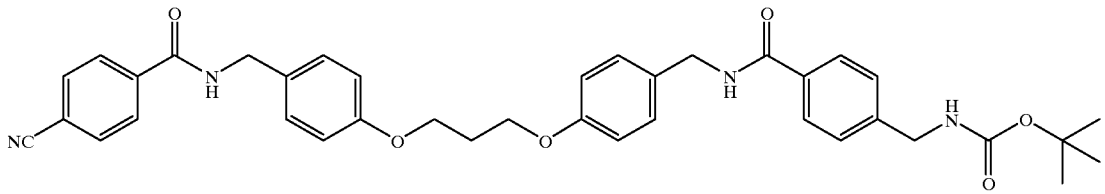

{[4-(3-{4-[(4-cyano-benzoylamino)-methyl]-phenoxy}- propoxy) -benzylcarbamoyl]-benzyl}-carbamic acid tert-butyl ester To a solution of 4-(tert-butoxycarbonylaminomethyl)-benzoic acid (106.9 mg, 0.43 mmol) in DMF (2 mL) were added 1-(3-dimethylaminopropyl)-3-ethyl carbodiimide hydrochloride (81.7 mg, 0.43 mmol) and 1-hydroxybenzotriazole (57.6 mg, 0.43 mmol). This mixture was stirred at room temperature for 20 minutes, and N-{4-[3-(4-aminomethyl-phenoxy)-propoxy]-benzyl}-4-cyanobenzamide from Example 80 was then added in one portion. After stirring at room temperature for 48 hours, the reaction mixture was diluted with EtOAc (75 mL), washed with 1N HCl (2×75 mL), dried over MgSO$_4$, and concentrated to provide the noted compound as a tan solid (244.00 mg, 87% yield).

LRMS (electrospray) m/z: 647 (M−1)

$^1$H NMR (DMSO-$d_6$): δ9.24 (t, 1H, J=6.02 Hz), 8.93 (t, 1H, J=5.52 Hz), 8.03 (d, 2H, J=8.53 Hz), 7.97 (d, 2H, J=8.53 Hz), 7.82 (d, 2H, J=8.04 Hz), 7.31 (d, 2H, J=8.03 Hz), 7.24 (d, 2H, J=8.53 Hz), 7.23 (d, 2H, J=8.53 Hz), 6.91 (d, 2H, J=8.54 Hz), 6.90 (d, 2H, J=8.53 Hz), 4.38–4.42 (m, 4H), 4.09 (t, 4H, J=6.02 Hz), 2.14 (m, 2H), 1.39 (s, 9H).

EXAMPLE 84

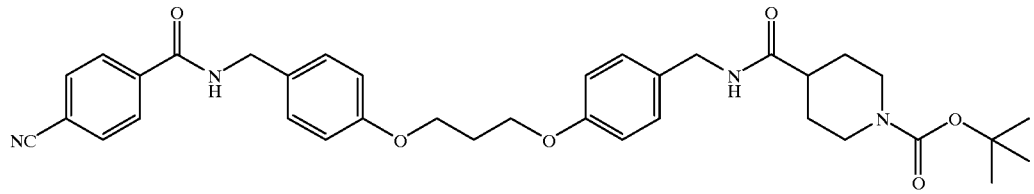

4- [4-(3-{4-[(4-cyano-benzoylamino)-methyl]-phenoxy}-propoxy)-benzylcarbamoyl]-piperidine-1-carboxylic acid tert-butyl ester The noted compound is prepared according to procedures outlined previously using N-{4-[3-(4-aminomethyl-phenoxy)-propoxy]-benzyl}-4-cyano-benzamide from Example 80 and N-boc-isonipecotic acid giving the desired product as a white solid (37 mg, 15% yield)

LRMS (electrospray) m/z: 627 (M+1), 644 (M+18), 625 (M−1)

¹H NMR (CDCl₃): δ7.89 (d, 2H, J=8.53 Hz), 7.71 (d, 2H, J=8.53 Hz), 7.26 (d, 2H, J=8.53 Hz), 7.16 (d, 2H, J=8.53 Hz), 6.89 (d, 2H, J=8.53 Hz), 6.86 (d, 2H, J=8.53 Hz), 6.72 (m, 1H), 5.83 (m, 1H), 4.57 (d, 2H, 5.52 Hz), 4.34 (d, 2H, 5.52 Hz), 4.15 (m, 4H) , 2.72 (br s, 2H), 2.26 (m, 3H), 1.57–1.85 (m, 6H), 1.46 (s, 9H).

EXAMPLE 85

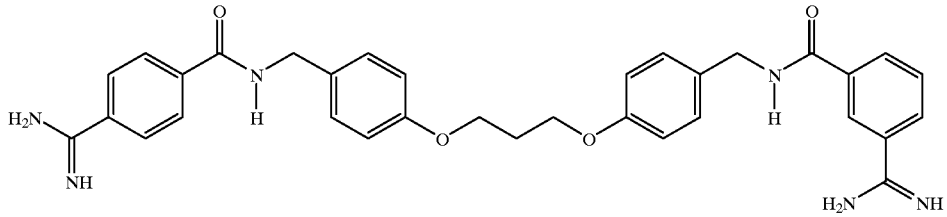

4-Carbamimidoyl-N-[4-(3-{4-[(3-carbamimidoyl-benzoylamino)-methyl]-phenoxy}-propoxy)-benzyl]-benzamide The noted compound is prepared according to procedures noted previously using the bis-nitrile prepared in accordance with Example 81, ammonium chloride and trimethyl aluminum in anhydrous toluene in a sealed tube at 150° C. for 16 hours. Workup as noted previously and reverse phase HPLC purification provided the TFA salt of the desired compound as a white solid (3% yield).

LRMS (electrospray) m/z: 308.4 (M/2+1), 615.2 (M+1)
MALDI m/z: 615.28 (M+1).
¹H NMR (CD₃OD): δ8.14–7.88 (c, 7H), 7.72 (t, 1H, J=8.5 Hz), 7.30 (d, 2H, J=6.0 Hz), 7.10, (d, 2H, J=5.5 Hz), 6.93 (d, 2H, J=7.0 Hz), 6.80 (d, 2H, J=6.5 Hz), 4.53 (S, 2H), 4.15–4.08 (c, 6H), 2.22 (m, 2H).

EXAMPLE 87

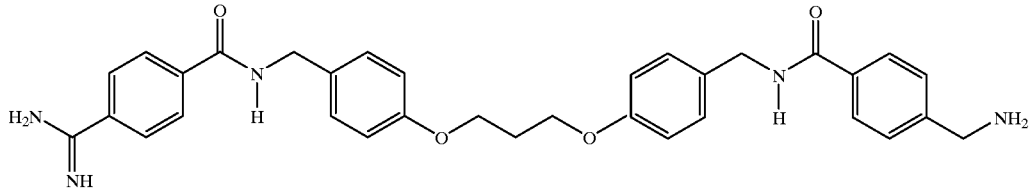

N-[4-(3-{4-[(4-Aminomethyl-benzoylamino)-methyl]-phenoxy}-propoxy)-benzyl]-4-carbamimidoyl-benzamide The noted compound is prepared according to above procedures using nitrile of Example 83 in a two step Pinner reaction (See, e., A. Pinner, et al., *Ber.* 10, 1889 (1877); *Ber.* 11, 4, 1475 (1878); and *Ber.* 16, 352, 1643 (1883)) which effected the conversion to the amidine and removed the t-butyl carbamate (Boc) protecting group. Anhydrous HCl in methanol returned the crude imidate which was further reacted in anhydrous ammonia in methanol at room temperature. Subsequent purification via reverse phase HPLC provided the TFA salt of the noted compound as a tan solid (7% yield).

LRMS (electrospray) m/z: 283.8 (M/2+1), 566.1(M+1)

purification provided the TFA salt of the noted product as a white solid (2% yield).
MALDI m/z: 579.72 (M+1).
¹H NMR (CD₃OD): δ8.29 (d, 1H, J=1.5 Hz), 8.20 (d, 1H, J=8.0 Hz), 8.06 (d, 2H, J=8.0 Hz), 7.96 (d, 1H, J=8.0 Hz), 7.90 (d, iH, J=8.5 Hz), 7.34 (t, 1H, J=7.8 Hz), 7.31 (d, 4H, J=8.5 Hz), 6.93 (d, 4H, J=8.5 Hz), 4.92 (s, 4H), 4.17 (t, 4H, J=6.0 Hz), 2.23 (m, 2H).

EXAMPLE 86

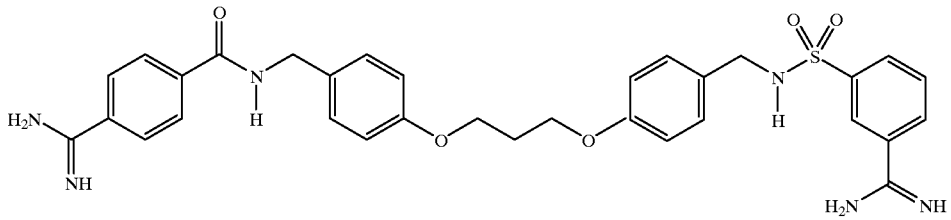

4-Carbamimidoyl-N-[4-(3-{4-[(3-carbamimidoyl-benzenesulfonylamino)-methyl]-phenoxy}-propoxy)-benzyl]-benzamide The noted compound was prepared according to above procedures using the bis-nitrile prepared in Example 82, ammonium chloride and trimethyl aluminum in anhydrous toluene in a sealed tube at 150° C. for 16 hours. Workup as MALDI m/z: 566.25 (M+1).

$^1$H NMR (CD$_3$OD): δ8.06 (d, 2H, J=8.0 Hz), 7.93 (d, 2H, J=8.5 Hz), 7.90 (d, 2H, J=8.5 Hz), 7.56 (d, 2H, J=8.0 Hz), 7.29 (dd, 4H, J=5.5, 8.5 Hz), 6.92 (dd, 4H, J=3.0, 9.0 Hz), 4.52 (d, 4H, J=7.5 Hz), 4.20–4.14 (c, 6H), 2.22 (m, 2H).

EXAMPLE 88

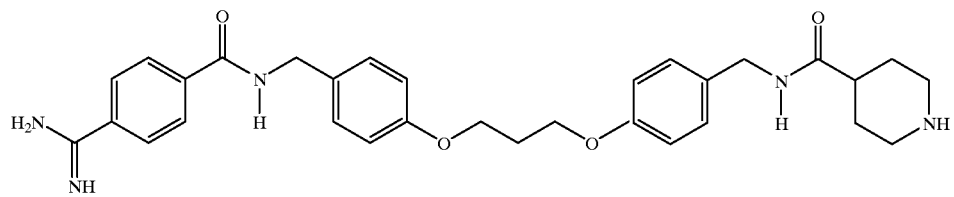

Piperidine-4-carboxylic acid 4-(3-{4-[(4-carbamimidoyl-benzoylamino)-methyl]-phenoxy}-propoxy)-benzylamide The noted compound is prepared according to above procedures using the nitrile of Example 84 in a two step Pinner reaction (See, e.g., A. Pinner, et al., Ber. 10, 1889 (1877); Ber. 11, 4, 1475 (1878); and Ber. 16, 352, 1643 (1883)) which effected the conversion to the amidine and removed the t-butyl carbamate (Boc) protecting group. Anhydrous HCl in methanol returned the crude imidate which was further reacted in anhydrous ammonia in methanol at room temperature. Subsequent purification via reverse phase HPLC provided the TFA salt of the desired compound as a white solid (24% yield).

LRMS (electrospray) m/z: 544.2 (M+1)

$^1$H NMR (CD$_3$OD): δ8.06 (d, 2H, J=8.5 Hz), 7.90 (d, 2H, J=8.5 Hz), 7.30 (d, 2H, J=8.5 Hz), 7.20 (d, 2H, J=8.5 Hz), 6.92 (t, 4H, J=8.7 Hz), 4.54 (s, 2H), 4.30 (s, 2H), 4.18–4.14 (c, 4H), 3.45 (br d, 2H, J=9.0 Hz), 3.03 (br s, 2H), 2.57 (m, 1H), 2.23 (m, 2H), 1.99–1.89 (c, 4H).

Also encompassed within the scope of the present invention are those compounds of Formula (I) in which the bridging portion of the molecule (i.e. that portion of the molecule between the two Ar' moieties) is conformationally restricted. A general procedure for the preparation of such compounds is outlined in the following scheme in which the bridging portion comprises a cyclobutyl substituent:

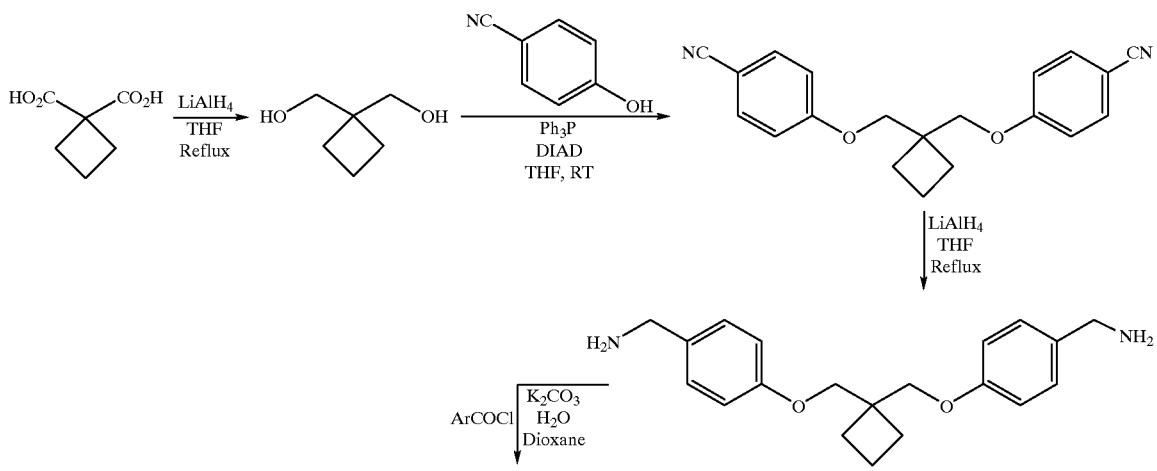

-continued

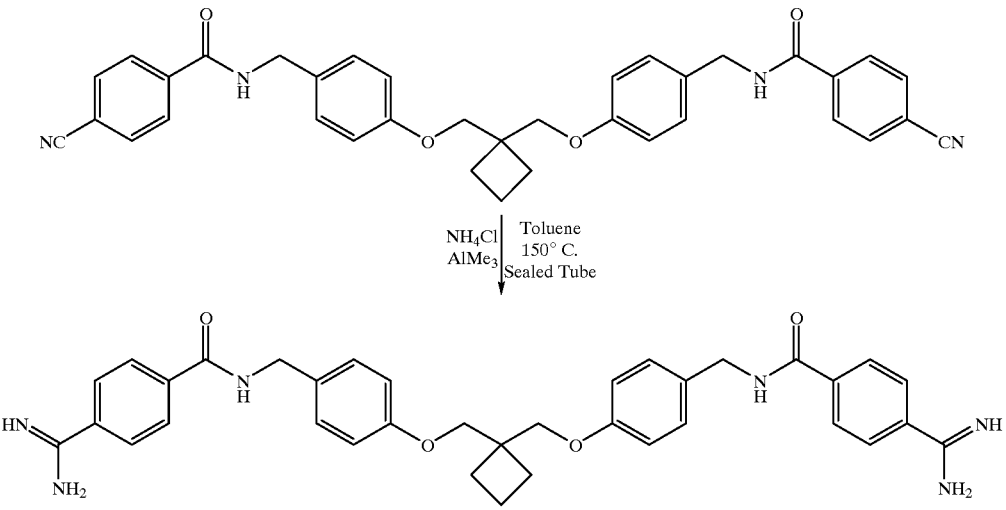

The following non-limiting examples and synthetic procedures further illustrate this embodiment of the invention:

EXAMPLE 89

1-Hydroxymethylcyclobutyl methanol 1,1-cyclobutanedicarboxylic acid (3.00 g, 20.8 mmol) was suspended in 80 mL of anhydrous THF under an atmosphere of argon. A 1M solution of LAH in THF (83.26 mL, 83.26 mmol) was carefully added by syringe and this mixture was refluxed for three hours followed by stirring at room temperature for 16 hours. The mixture was carefully quenched by the successive addition of 3.2 mL of water, 3.2 mL of 15% aqueous NaOH, and 9.6 mL of water. This mixture was then diluted with diethyl ether, filtered, and the filtrate concentrated under reduced pressure to yield the product as a clear oil (2.0 g, 83% yield).

LRMS (electrospray) m/z: 117 (M+1)

$^1$H NMR (CDCl$_3$): δ3.77 (s, 4H), 2.41 (s, 2H), 1.92–1.99 (m, 2H), 1.79–1.83 (m, 4H).

EXAMPLE 90

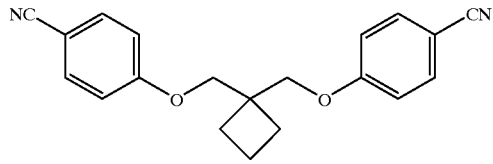

4,4'-(2-cyclobutylpropanediyldioxy)-di-benzonitrile

The noted compound was prepared according to the procedures outlined above using 1-hydroxymethyl-cyclobutyl methanol of Example 89, 4-cyanophenol, diisopropyl diazodicarboxylate and triphenylphosphine to provide, following purification via flash chromatography, the pure diether as a white solid (37%).

LRMS (electrospray) m/z: 117 (M+1)

$^1$H NMR (CDCl$_3$): δ7.59 (d, 4H, J=9.0 Hz), 6.98 (d, 4H, J=8.5 Hz), 4.12 (s, 4H), 2.06–2.10 (m, 6H).

EXAMPLE 91

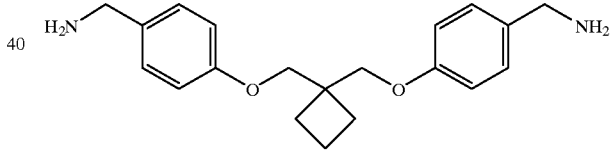

4-[1-(4-aminomethyl-phenoxymethyl)-cyclobutylmethoxy]-benzylamine

The noted compound was prepared according to the rocedures above using 4,4'-(2-cyclobutylpropane-diyldioxy)-di-benzonitrile from Example 90 and lithium aluminum hydride to provide the desired diamine as a yellow oil (83%).

LRMS (electrospray) m/z: 327 (M+1)

$^1$H NMR (CD$_3$OD): δ7.23 (d, 4H, J=8.5 Hz), 6.91 (d, 4H, J=9.0 Hz), 4.07 (s, 4H), 4.07 (s, 4H), 3.71 (s, 4H), 2.04–2.09 (m, 6H).

EXAMPLE 92

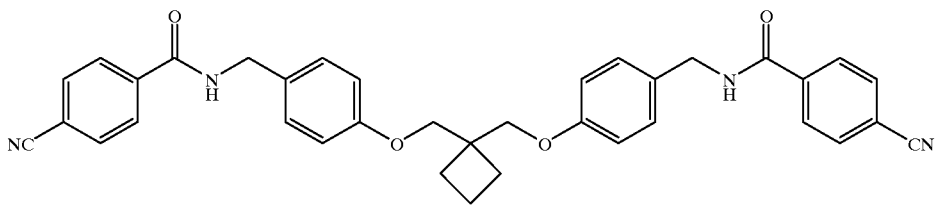

1,1-Bis-{4-[(4-cyanobenzoyl-amino)-methyl]-phenoxy-methyl}-cyclobutane

The noted compound was prepared according to procedures above using 4-[1-(4-aminomethyl-phenoxymethyl)-cyclobutylmethoxy]-benzylamine from Example 91 and 4-cyanobenzoyl chloride to yield a yellow foam (1.4 g, 78% yield).

LRMS (electrospray) m/z: 585 (M+1), 602 (M+18)

$^1$H NMR (CDCl$_3$): δ7.88 (d, 4H, J=8.5 Hz), 7.74 (d, 4H, J=8.5 Hz), 7.26 (d, 4H, J=9.0 Hz), 6.91 (d, 4H, J=9.0 Hz), 6.45 (m, 1H), 4.58 (d, 4H, J=5.5 Hz), 4.07 (s, 4H), 2.04–2.08 (m, 6H).

EXAMPLE 93

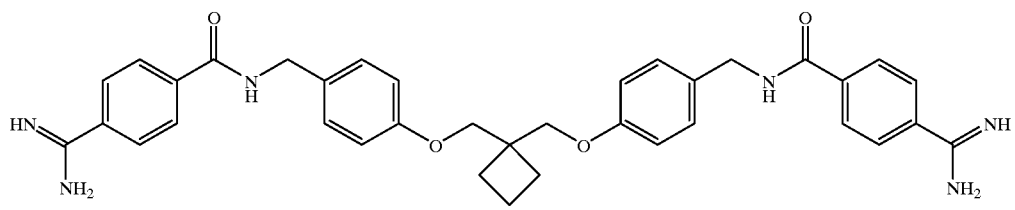

1,1-Bis-{4-[(4-carbamimidoyl-benzoyl-amino)-methyl]-phenoxy-methyl}-cyclobutane The noted compound was prepared according to the procedures above using the bis-nitrile of Example 92, ammonium chloride and trimethyl aluminum in anhydrous toluene in a sealed tube at 150° C. for 16 hours. Workup as indicated previously and reverse phase HPLC purification provided the TFA salt of the desired product as a white solid (5% yield).

MALDI m/z: 619.16 (M+1).

$^1$H NMR (CD$_3$OD): δ8.05 (d, 2H, J=8.5 Hz), 7.98 (d, 2H, J=8.0 Hz), 7.89 (d, 2H, J=8.5 Hz), 7.84 (d, 2H, J=8.5 Hz), 7.27 (dd, 4H, J=4.0, 8.5 Hz), 6.92 (dd, 4H, J=2.0, 8.5 Hz), 4.51 (d, 4H, J=7.0 Hz), 4.08 (s, 4H), 2.06 (br s, 6H).

Also encompassed by the compounds of the present invention are those compounds in which Ar is aryl or heteroaryl. The preparation of a representative compound of Formula (I) in which Ar is a naphthalene moiety is provided below:

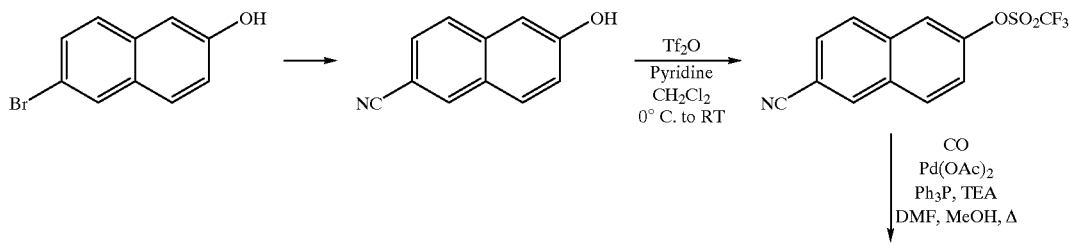

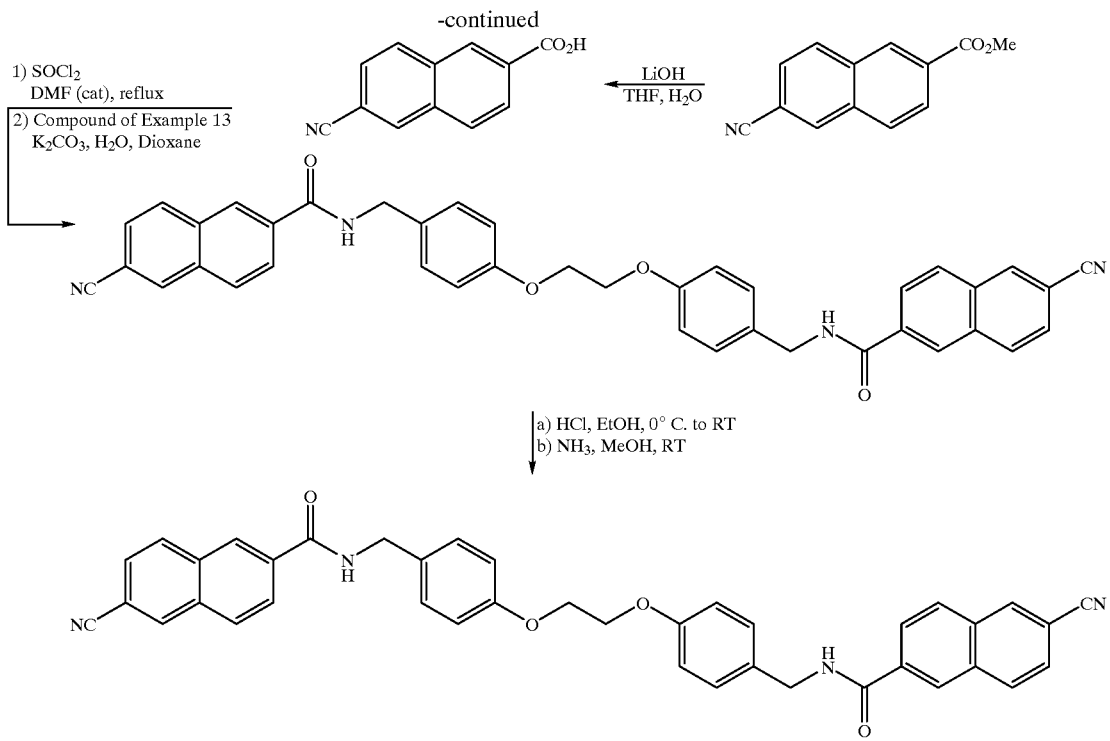

EXAMPLE 94

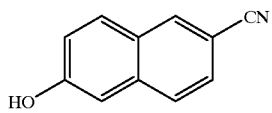

6-Cyano-2-naphthol

The noted compound was prepared from 6-bromo-2-naphthol according to the procedure of Aoyama et al., *Chem. Pharm. Bull.*, 33, 1458 (1985) in 56% yield after flash chromatography.

EXAMPLE 95

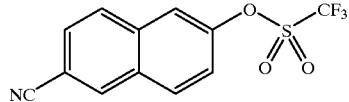

Trifluoromethanesulfonic acid 6-cyano -naphthalen-2-yl ester

A flame dried flask equipped with a stir bar and rubber septum was charged with dry dichlorornethane (35 mL) and 6-cyano-2-naphthol (3.00 g, 17.73 mmol) fromn Example 94 under an argon atmosphere. To this mixture was added pyridine (7.17 mL, 88.61 mmol), and the resulting solution was chilled to 0° C. Triflic anhydride (3.59 mL, 21.28 mmol) was added slowly by syringe, and the reaction mixture was stirred at 0° C. for 1.5 hours. one half equivalent of triflic anhydride was then added and the reaction mixture was allowed to gradually warm to room temperature over a 16 hour period. The solvents were then removed by rotary evaporation, and the residue was taken up in 200 mL of 1:1 EtOAc and 1N HCl. The organics were washed once more with 1N HCl (100 mL), dried over $MgSO_4$, and concentrated. Flash chromatography (hexane to 15% EtOAc/hexane) afforded the desired product as a white solid (3.98 g, 75%).

LRMS (electrospray) m/z: 319 (M+18)

$^1$H NMR (CDCl$_3$) δ8.32 (s, 1H), 8.05 (d, 1H, J=9.04 Hz), 8.01 (d, 1H, J=8.54 Hz), 7.85 (d, 1H, J=2.51 Hz), 7.76 (dd, 1H, J=9.04, 1.51 Hz), 7.54 (dd, 1H, J=9.03, 2.51 Hz).

EXAMPLE 96

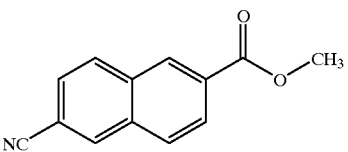

6-Cyano-naphthalene-2-carboxylic acid methyl ester

To a solution of trifluoromethanesulfonic acid 6-cyano-naphthalen-2-yl ester from Example 95 (1.50 g, 4.98 mmol) in 20 mL of anhydrous DMF was added palladium(II) acetate (33.53 mg, 0.15 mmol), triphenylphosphine (78.36 mg, 0.30 mmol), triethylamine (1.39 mL, 9.96 mmol) and 5 mL of methanol. This mixture was purged with carbon monoxide for ten minutes. The reaction mixture was then placed under balloon pressure of carbon monoxide and heated to 60° C. for 16 hours. The mixture was then diluted with brine, extracted with EtOAc (3×100 mL), extracts washed with 1N HCl (2×100 mL), dried over $MgSO_4$, and concentrated under reduced pressure. Flash chromatography (hexane to 20% EtOAc/hexane) afforded the desired product as a white solid (525 mg, 50%).

LRMS (electrospray) m/z: 229 (M+18)

¹H NMR (CDCl₃): δ8.66 (s, 1H), 8.29 (s, 1H), 8.20 (dd, 1H, J=8.54, 1.51 Hz), 8.06 (d, 1H, J=8.54 Hz), 7.98 (d, 1H, J=8.53 Hz), 7.70 (dd, 1H, J=8.53, 1.50 Hz), 4.03 (s, 3H).

EXAMPLE 97

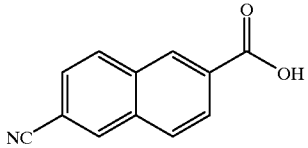

6-Cyano-naphthalene-2-carboxylic acid

A solution of 6-cyano-naphthalene-2-carboxylic acid methyl ester from Example 96 (2.00 g, 9.47 mmol) in THF (19 mL) and 1M aqueous LiOH (18.94 mL, 18,94 mmol) was vigorously stirred at room temperature for 3 hours. The reaction mixture was then diluted with 150 mL of 1:1 dichloromethane/water, and the organics were discarded. The aqueous material was acidified to pH 2 with 1N HCl, extracted with EtOAc (2×150 mL), extracts dried over MgSO₄, and concentrated to provide the desired compound as a white solid (1.61 g, 86%).

LRMS (electrospray) m/z: 196 (M−1)

¹H NMR (DMSO-d₆) δ13.40 (s, 1H), 8.73 (s, 1H), 8.69 (s, 1H), 8.34 (d, 1H, J=9.03 Hz), 8.17 (d, 1H, J=8.53 Hz), 8.12 (m, 1H), 7.89 (m, 1H).

EXAMPLE 98

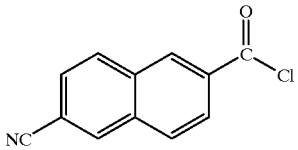

6-Cyano-naphthalene-2-carbonyl chloride

A mixture of 6-cyano-naphthalene-2-carboxylic acid (250.00 mg, 1.27 mmol), thionyl chloride (15 mL), and a few drops of DMF was refluxed for two hours under a condenser equipped with a drying tube containing anhydrous calcium sulfate. The thionyl chloride was then removed by high vacuum distillation, yielding a quantitative yield of a yellow solid. This material was not characterized, and was carried on without further purification.

EXAMPLE 99

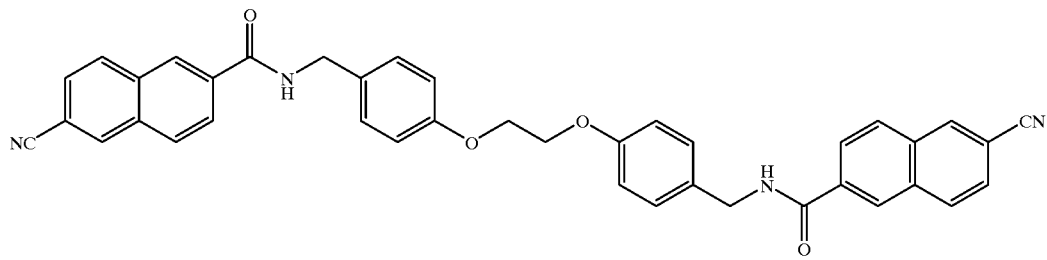

1,2-Bis-{4-[(6-cyano-naphthalene-2-carbonylamino)-methyl]-phenoxy}-ethane

The noted compound was prepared according to procedures outlined previously using bis-benzyl amine from Example 13 and the acid chloride of Example 98 to provide the desired diamide as a yellow/tan solid (275 mg, 40% yield).

LRMS (electrospray) m/z: 648 (M+18)

¹H NMR (DMSO-d₆) : δ9.29 (t, 2H, J=6.02 Hz), 8.66 (s, 2H), 8.59 (s, 2H), 8.22 (d, 2H, J=9.04 Hz), 8.15 (d, 2H, J=8.53 Hz), 8.10 (dd, 4H, J=8.53, 1.50 Hz), 7.87 (dd, 2H, J=8.53, 1.50 Hz), 7.30 (d, 4H, J=8.53 Hz), 6.96 (d, 4H, J=9.03 Hz), 4.48 (m, 4H), 4.26 (s, 4H).

EXAMPLE 100

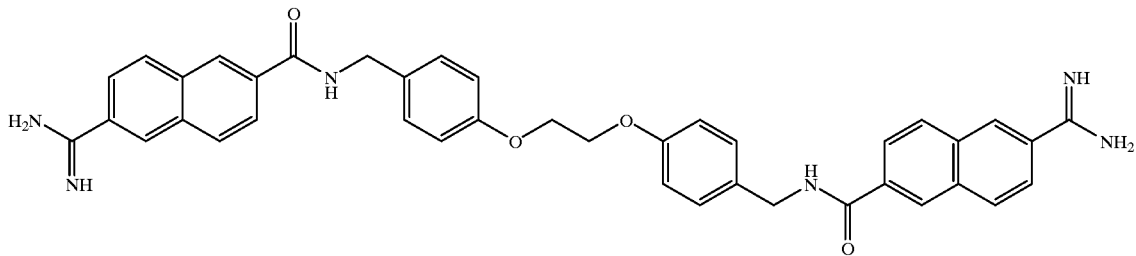

1,2-Bis-{4-[(6-carbamimidoylnaphthalene-2-carbonylamino)-methyl]-phenoxy}-ethane The noted compound was prepared according to the procedures outlined above using the bis-nitrile from

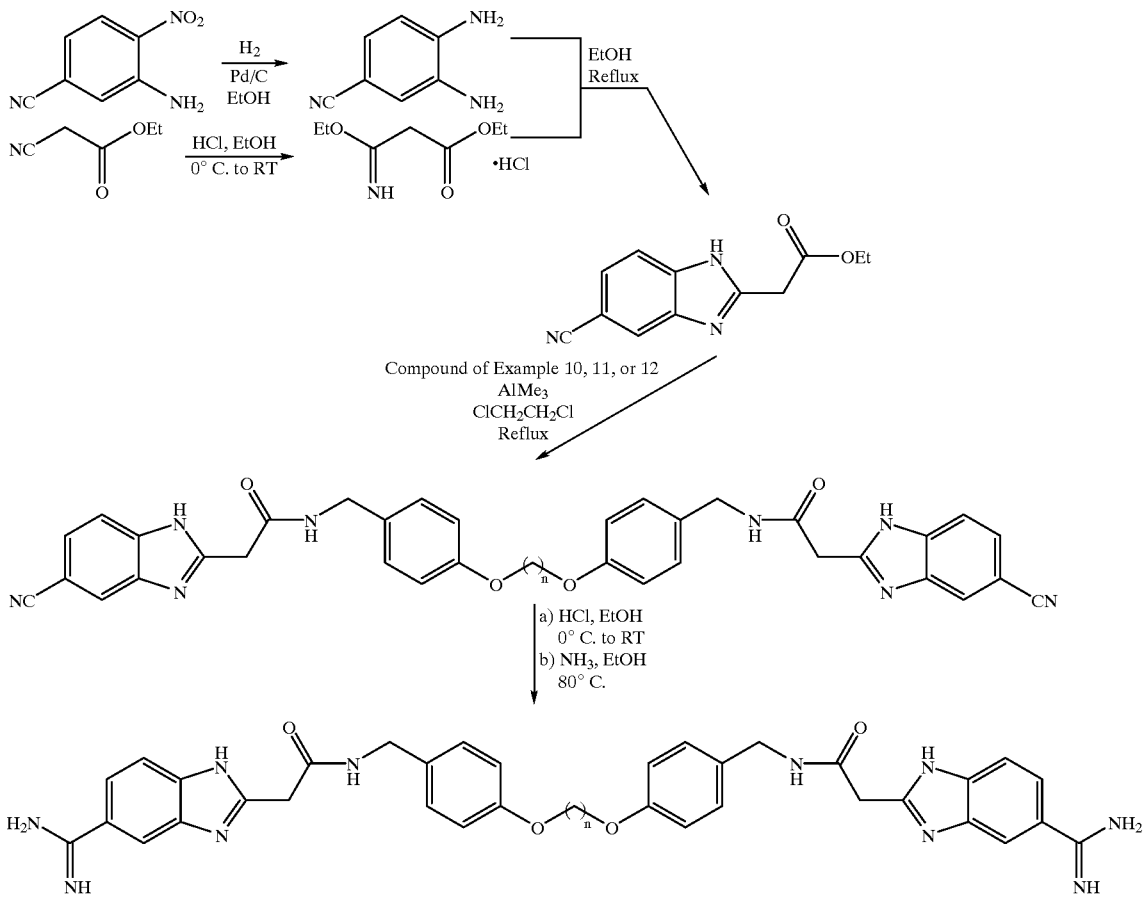

Example 99 to provide, after HPLC purification, the desired bis-amidine as a white solid (bis-TFA salt) (8 mg, 4% yield).

LRMS (electrospray) m/z: 665 (M+1)

$^1$H NMR (CD$_3$OD): δ 8.53 (s, 2H), 8.50 (s, 2H), 8.24 (d, 2H, J=8.53 Hz), 8.18 (d, 2H, J=8.54 Hz), 8.09 (d, 2H, J=9.04 Hz), 7.88 (d, 2H, J=8.53 Hz), 7.36 (d, 4H, J=8.53 Hz), 6.99 (d, 4H, 8.54 Hz), 4.60 (s, 4H), 4.33 (s, 4H).

As noted, also encompassed by the compounds of the present invention are those compounds in which Ar is heteroaryl. The preparation of a representative compounds of Formula (I) in which Ar is a benzimidazole moiety is provided below:

EXAMPLE 101

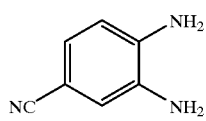

3,4-diaminobenzonitrile

3-Amino-4-nitrobenzonitrile (20.00 g, 0.042 mol) was hydrogenated under 50 psi of hydrogen gas in 250 mL of anhydrous ethanol with 1.00 g of 10% Pd/C for 5 hours. The mixture was then filtered through a pad of celite and the filtrate concentrated. Trituration of the resulting solid with diethyl ether afforded 11.40 g of the desired product as a tan solid (70%).

$^1$H NMR (CD$_3$OD): δ7.96 (d, 1H, J=1.50 Hz), 7.69 (d, 1H, J=8.03 Hz), 7.56 (dd, 1H, J=8.03, 1.51 Hz), 4.24 (q, 2H, J=7.03 Hz), 1.29 (t, 3H, J=7.03 Hz).

EXAMPLE 104

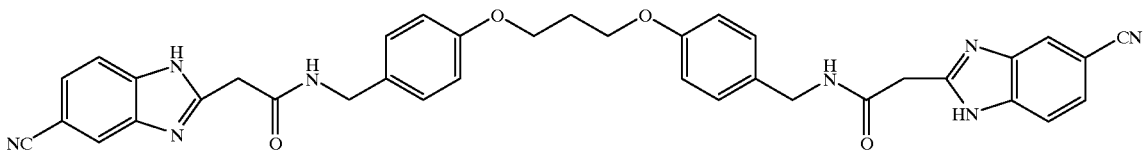

$^1$H NMR (CD$_3$OD): δ6.88 (m, 2H), 6.65 (d, 2H, J=8.53 Hz).

EXAMPLE 102

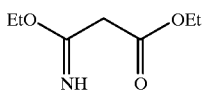

2-(5-Cyano-1H-benzoimidazol-2-yl)-N-{4-[3-(4-{[2-(5-cyano-1H-benzoimidazol-2-yl)-acetylaminol-methyl}-phenoxy)-propoxyl-benzyl}-acetamide

Ethoxycarbonimidoyl-acetic acid ethyl ester

A solution of ethyl cyanoacetate (10.00 g, 0.088 mol) in 100 mL of anhydrous ethanol was chilled to 0° C. and HCl gas was bubbled into the solution for 15 minutes. The reaction vessel was capped and allowed to stir at room temperature for 16 hours. The reaction mixture was then purged with argon for 20 minutes, and the solvent removed under reduced pressure. The resulting white solid was triturated with diethyl ether, filtered, and dried under high vacuum yielding 15.8 g (92%) of imidate as a hydrochloride salt.

LRMS (electrospray) m/z: 160 (M+1)

$^1$H NMR (CD$_3$OD): δ4.54 (q, 2H, J=7.03 Hz), 4.20 (q, 2H, J=7.03 Hz), 1.51 (t, 3H, J=7.03 Hz), 1.28 (t, 3H, J=7.03 Hz).

A flame dried flask was charged with bis-benzylamine prepared in accordance with Example 12 (239.23 mg, 0.84 mmol) and 5 mL of anhydrous 1,2-dichloroethane under an argon atmosphere. This solution was chilled to 0° C. and a 1M solution of dimethylaluminum chloride in hexane (1.67 mL, 1.67 mol) was added by syringe. The ice bath was removed and this mixture was stirred at room temperature for 1.5 hours. At this time, the benzimidazole ester of Example 103 was added in one portion to the aluminate, followed by 5 mL of 1,2-dichloroethane. This mixture was refluxed for 16 hours, and then poured into a slurry of silica gel/dichloromethane. The slurry was filtered, the silica gel rinsed with 10% MeOH/dichloromethane, and the filtrate concentrated. Column flash chromatography (100% dichloromethane to 10% MeOH/dichloromethane) afforded the desired diamide as a white solid (70 mg, 6% yield).

EXAMPLE 103

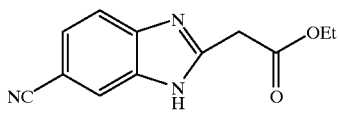

(6-Cyano-1H-benzoimidazol-2-yl)-acetic acid ethyl ester

A mixture of the diaminobenzonitrile from Example 101 (1.00 g, 7.51 mmol) and the imidate from Example 102 (2.94 g, 15.02 mmol) in 50 mL of anhydrous ethanol was refluxed for 16 hours. The solvent was then removed under reduced pressure, and the residue taken up in 1N HCl (75 mL), extracted with dichloromethane (2×75 mL), and the extracts discarded. The aqueous material was brought to pH 12 with concentrated ammonium hydroxide, extracted with dichloromethane (2×100 mL), extracts dried over MgSO$_4$, and concentrated to provide the final product as an off white solid (1.62 g, 94%).

LRMS (electrospray) m/z: 230 (M+1)

LRMS (electrospray) m/z: 653 (M+1)

$^1$H NMR (DMSO-d$_6$): δ8.68 (m, 2H), 8.07 (s, 2H), 7.71 (d, 2H, J=8.53 Hz), 7.64 (d, 2H, J=8.53 Hz), 7.21 (d, 4H, J=8.54 Hz), 6.91 (d, 4H, J=8.54 Hz), 4.26 (d, 4H, J=5.52 Hz), 4.11 (t, 4H, J=6.53 Hz), 3.87 (s, 4H), 2.14 (m, 2H).

EXAMPLE 105

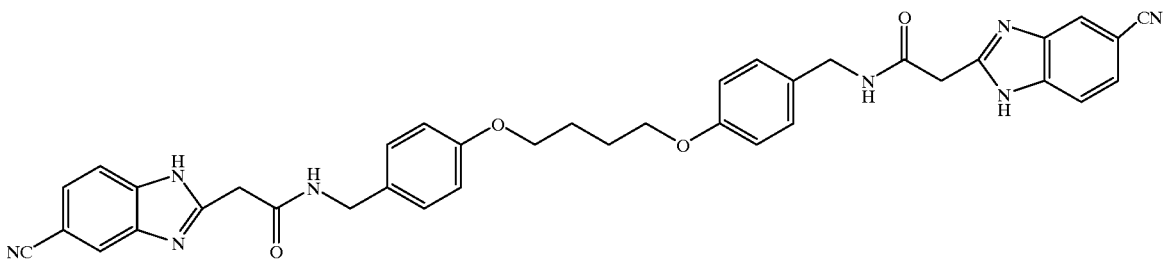

2-(5-Cyano-1H-benzoimidazol-2-yl)-N-{4-[4-(4-{2-(5-cyano-1H-benzoimidazol-2-yl)-acetylaminol-methyl}-phenoxy)-butoxy]-benzyl}-acetamide The noted compound was prepared according to the procedure above using the benzimidazole ester of Example 103 and the bis-benzylamine of Example 11 to give the noted diamide as a white solid (47 mg, 11% yield).

LRMS (electrospray) m/z: 667 (M+1)

¹H 3MR (DMSO-d₆): δ8.73 (t, 2H, J=6.03 Hz), 8.05 (br s, 2H), 7.67 (br s, 2H), 7.55 (d, 2H, J=9.03 Hz), 7.21 (d, 4H, J=8.53 Hz), 6.99 (d, 4H, J=8.54 Hz), 4.25 (d, 4H, J=6.03 Hz), 4.01 (m, 4H), 3.87 (s, 4H), 1.85 m, 4H).

EXAMPLE 106

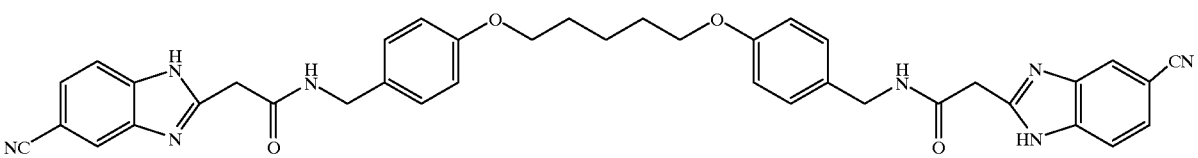

2-(5-Cyano-1H-benzoimidazol-2-yl)-N-{4-[5-(4-{[2-(5-cyano-1H-benzoimidazol-2-yl)-acetylamino]-methyl}-phenoxy)-pentoxy]-benzyl}-acetamide The noted compound was prepared according to the procedure above using the benzimidazole ester of Example 103 and the bis-benzylamine of Example 10 to give the desired diamide as a white solid (47 mg, 11% yield).

LRMS (electrospray) m/z: 681 (M+1)

¹H NMR (DMSO-d₆) : δ8.68 (t, 2H, J=6.02 Hz), 8.04 (s, 2H), 7.67 (d, 2H, J=7.53 Hz), 7.54 (dd, 2H, J=8.03, 1.5 Hz), 7.21 (d, 4H, J=8.53 Hz), 6.88 (d, 4H, J=8.53 Hz), 4.25 (d, 4H, J=6.02 Hz), 3.97 (t, 4H, J=6.02 Hz), 3.87 (s, 4H), 1.77 (m, 4H), 1.55 (m, 2H).

EXAMPLE 107

2-(5-Carbamimidoyl-1H-benzoimidazol-2-yl)-N-{4,-[3-(4-{2-(5-carbamimidoyl-1H-benzoimidazol-2-yl) acetylaminol-methyl}-phenoxy)-propoxy]-benzyl}-acetamide A mixture of the diamide from Example 104 (70.00 mg, 0.11 mmol) in 5 mL of anhydrous ethanol was chilled to 0° C. and HCl gas bubbled in for 15 minutes. The reaction vessel was capped and the mixture stirred at room temperature for 16 hours. The solvent was then removed under reduced pressure and the remaining material was taken up in anhydrous ethanol in a pressure tube, chilled to 0° C. and ammonia bubbled in for 15 minutes. The pressure tube was capped and then heated to 80° C. for 5 hours. This mixture was then concentrated under reduced pressure and purified by reverse phase HPLC, yielding the desired product as a tan solid-TFA salt (3 mg, 4% yield).

LRMS (electrospray) m/z: 687 (M+1)

¹H NMR (CD₃OD): δ8.15 (d, 2H, 1.0 Hz), 7.83 (d, 2H, J=8.53 Hz), 7.77 (dd, 2H, J=8.53, 1.51 Hz), 7.26 (d, 4H, J=9.04 Hz), 6.92 (d, 4H, J=8.53 Hz), 4.38 (s, 4H), 4.17 (t, 4H, J=6.02 Hz), 2.23 (m, 2H).

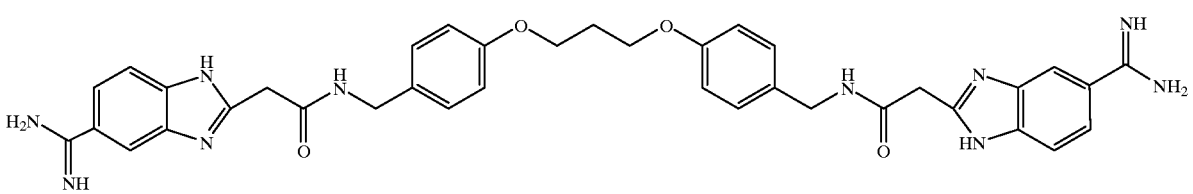

EXAMPLE 108

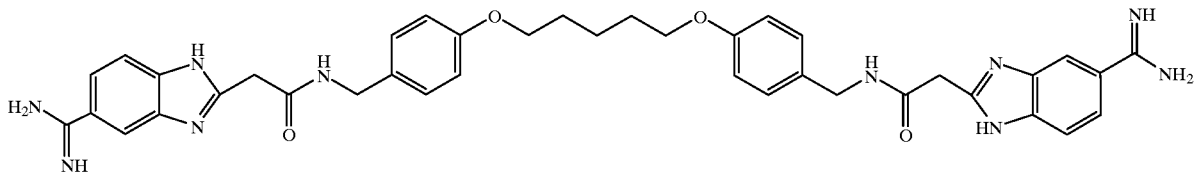

2-(5-Carbamimidoyl-1H-benzoimidazol-2-yl)-N-{4-[5-(4-{2-(5-carbamimidoyl-1H-benzoimidazol-2-yl)acetylamino]-methyl}-phenoxy)-pentoxy]-benzyl}-acetamide The noted compound was prepared according to the procedure above-using the diamide of Example 106 giving 3.5 mg of the desired product as a white solid-TFA salt (4%).

LRMS (electrospray) m/z: 715 (M+1)

$^1$H NMR (CD$_3$OD): δ8.13 (s, 2H), 7.81 (d, 2H, J=8.53 Hz), 7.75 (d, 2H, J=9.03 Hz), 7.25 (d, 4H, J=8.54 Hz), 6.89 (d, 4H, J=8.54 Hz), 4.38 (s, 4H), 4.01 (t, 4H, J=6.02 Hz), 1.86 (m, 4H), 1.67 (m, 2H).

EXAMPLE 109

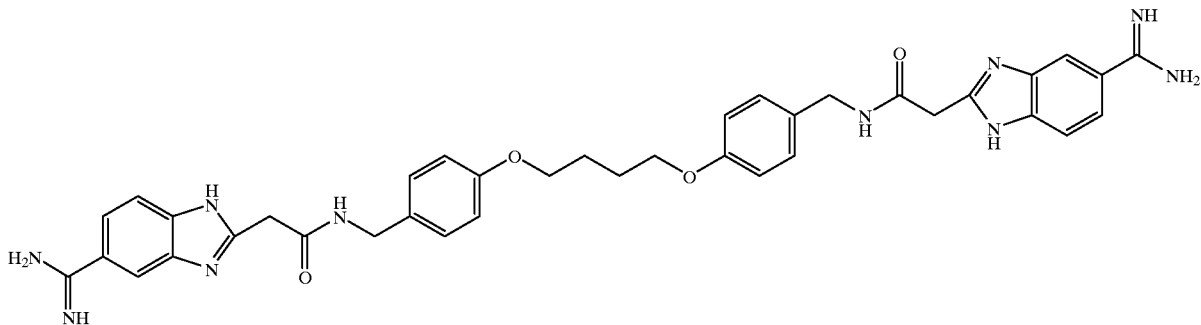

2-(5-Carbamimidoyl-1H-benzoimidazol-2-yl)-N-{4-[4-(4-{2-(5-carbamimidoyl-1H-benzoimidazol-2-yl)acetylamino]-methyl}-phenoxy)-butoxy]-benzyl}-acetamide A flame dried flask equipped with a stir bar and rubber septum was charged with anhydrous benzene (5 mL) and ammonium chloride (54.55 mg, 1.02 mmol). Trimethylaluminum (2M solution in toluene, 0.510 mL, 1.02 mmol) was then added by syringe dropwise (gas evolution observed) and the mixture stirred at room temperature for two hours under an argon atmosphere. The diamide of Example 105 was then added in one portion and the mixture refluxed for 16 hours. The mixture was then poured into a slurry of silica gel/dichloromethane, filtered, the silica gel rinsed with methanol, and the filtrate concentrated under reduced pressure. The resulting solid was purified by reverse phase HPLC, giving 1.5 mg of the final diamidine as a tetra-TFA salt (3%).

LRMS (electrospray) m/z: 701 (M+1)

$^1$H NMR (CD$_3$OD): δ8.11 (s, 2H), 7.79 (d, 2H, J=9.03 Hz), 7.73 (d, 2H, J=8.53), 7.25 (d, 4H, J=8.53 Hz), 6.90 (d, 4H, J=8.53 Hz), 4.44 (s, 4H), 4.05 (m, 4H), 1.96 (m, 4H).

Also contemplated within the scope of the present invention are those compounds of Formula (I) in which one portion of the molecule is asymmetric relative to the other portion of the molecule. That is, although the preferred compounds of Formula (I) are symmetrical, this is not a requirement. The following non-limiting examples and synthetic procedures further illustrate embodiments of the invention in which each substituent Y is different from the other within a given compound of Formula (I):

EXAMPLE 110

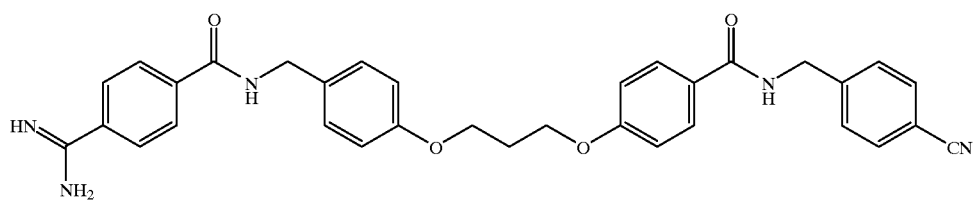

4-Cyano-(3-{4-[(4-carbamimidoyl-benzoylamino)-methyl]-phenoxy}-propoxy)-benzylamide This product was isolated as a by-product from the preparation of the bis-amidine of Example 62 as a white solid (38 mg; 13%).

LRMS (electrospray) m/z: 562.3 (M+1).

$^1$H NMR (DMSO-d$_6$) : δ8.08 (d, 2H, J=8.5 Hz) , 8.03 (d, 2H, J=8.0 Hz), 7.96 (d, 2H, J=8.5 Hz), 7.90 (d, 2H, J=8.5 Hz), 7.23 (dd, 4H, J=4.0, 8.5 Hz), 6.91 (dd, 4H, J=3.1, 8.5 Hz), 4.42 (d, 4H, J=6.5 Hz), 4.10 (t, 4H, J=6.1 Hz), 2.14 (m, 2H).

EXAMPLE 111

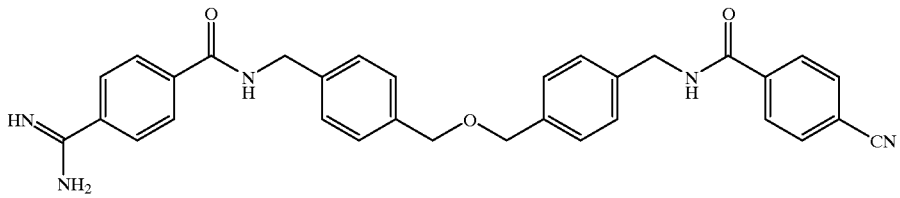

4-Amidino-{4-[(4-cyano-benzoylamino)-methyl]-benzyloxymethyl}-benzylamide

This product was isolated as a by-product from the preparation of bis-amidine of Example 66 as a white solid (4 mg; 4%).

LRMS (electrospray) m/z: 532.0 (M+1).

$^1$H NMR (CD$_3$OD): δ8.07 (d, 2H, J=8.0 Hz), 8.00 (d, 2H, J=8.0 Hz), 7.91 (d, 2H, J=8.5 Hz), 7.86 (d, 2H, J=8.3 Hz), 7.37–7.35 (c, 8H), 4.91 (d, 4H, J=3.0 Hz), 4.60 (s, 4H).

Also provided are representative compounds of Formula (I) in which Ar is a benzothiophene moiety. A general procedure for preparing such compounds is provided below:

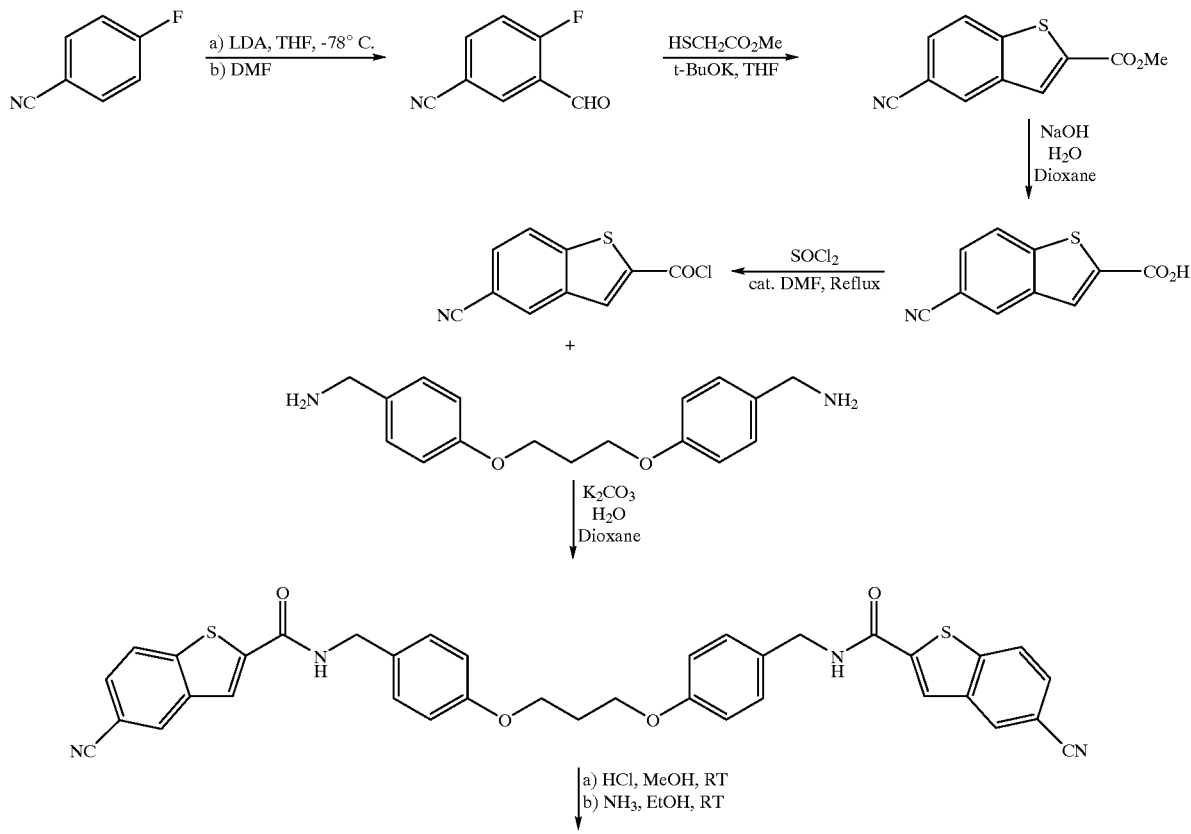

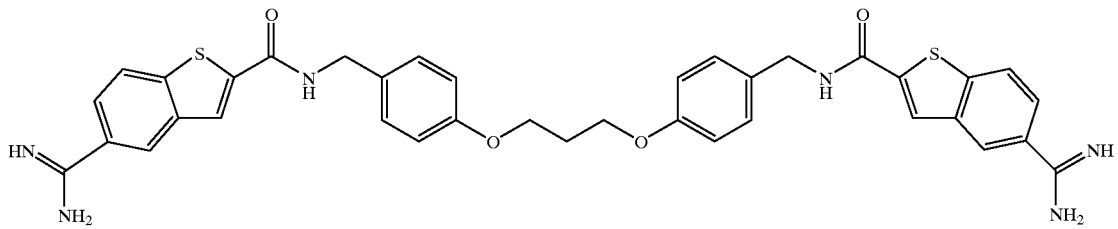

The following chemistry is based upon a literature procedure: A. J. Bridges et al., *Tetrahedron Lett.* 7499–7502 (1992).

EXAMPLE 112

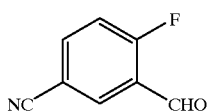

2-Fluoro-5-cyano-benzaldehyde

To a stirred, cooled solution (0° C.) of diisopropylamine (15.4 mL, 0.11 mol) in anhydrous tetrahydrofuran (200 mL) n-butyllithium (40 mL of 2.5M in hexane, 0.11 mol) was added from a dropping funnel over a period of 30 min. under argon. The mixture was stirred at that temperature for 30 min. and then cooled to −78° C. A solution of 4-fluoro-benzonitrile (12.1g, 0.1 mol) in dry THF (50 mL) was then added dropwise over 15 min. via syringe and stirred for 1 hour at −78° C. Dimethylformamide (8 mL) was added dropwise from a syringe and the stirring was continued for another 20 min. The reaction was quenched by the rapid addition of acetic acid (20 mL) followed by water (500 mL) and the product was extracted with diethyl ether (2×500 mL). The combined organic layers were washed with 1N HCl, water, saturated sodium chloride and then dried over anhydrous magnesium sulfate, and evaporated to give 2-fluoro-5-cyano-benzaldehyde (11.8 g, 79% yield) as a light yellow solid.

$^1$H NMR (CDCl$_3$): δ10.32 (s, 1H), 8.18 (dd, 1H, J=6.5, 2.5 Hz), 7.88 (m, 1H), 7.33 (t, 1H, J=9.5 Hz).

EXAMPLE 113

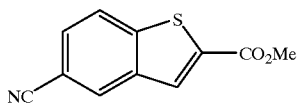

Methyl 5-cyano-benzthiophene-2-carboxylate

Methylthioglycollate was added to t-BuOK (43 mL, 1M in THF) in a flame dried flask cooled in ice-water bath. An additional 100 mL of dry THF was added and the mixture was stirred at room temperature for 30 min. A solution of 2-fluoro-5-cyano-benzaldehyde from Example 112 (6g, 0.04 mol) in 100 mL of dry THF was added dropwise via a syringe over a period of 30 min. The reaction was exothermic and a considerable darkening of the reaction mixture was observed. The reaction mixture was stirred for another 30 min. at room temperature. The mixture was carefully added to an ice-water mixture and the precipitated was removed by filtration. The precipitate was dissolved in chloroform and dried over magnesium sulfate. The solution was filtered and evaporated to give methyl 5-cyano-benzthiophene-2-carboxylate (7.5 g, 86.4% yield).

$^1$H NMR (CDCl$_3$): d 8.16 (s, 1H), 8.04 (s, 1H), 7.92 (d, 1H, J=8.5 Hz), 7.62 (d, 1H, J=8.5 Hz).

EXAMPLE 114

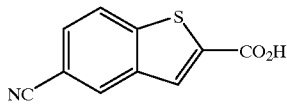

5-Cyano-benzthiophene-2-carboxylic acid

5-Cyano-benzthiophene-2-carboxylic acid from Example 113 (6.8 g, 0.0314 mol) was dissolved in dioxane (250 mL), and water (500 ml). Sodium hydroxide (10 N in water, 6.6 mL) was added slowly to the above solution at room temperature for 3 hours. The reaction mixture was then neutralized with concentrated HCl and the product was extracted with ethyl acetate (3×500 mL), dried over sodium sulfate and evaporated to give the 5-cyano-benzthiophene-2-carboxylic acid (6.28 g, 98.7% yield) as a white solid.

$^1$H NMR (CDCl$_3$): δ13.85 (br s, 1H), 8.58 (s, 1H), 8.33 (d, 1H, J=8.5 Hz), 8.22 (s, 1H), 7.90 (d, 1H, J=8.5 Hz).

EXAMPLE 115

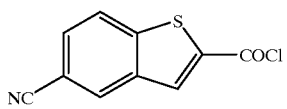

5-Cyano-2-benzthiophenoyl chloride

The product of Example 114 (450 mg) was refluxed with thionyl chloride (10 mL) and a few drops of dimethylformamide for 3 hours. The solvent was evaporated and the residue was vacuum dried to give the desired acid chloride as a pale yellow solid (535 mg, 91.8% yield).

$^1$H NMR (CDCl$_3$): δ8.35 (s, 1H), 8.33 (s, 1H), 8.04 (d, 1H, J=8.5 Hz), 7.77 (d, 1H, J=8.5 Hz).

EXAMPLE 116

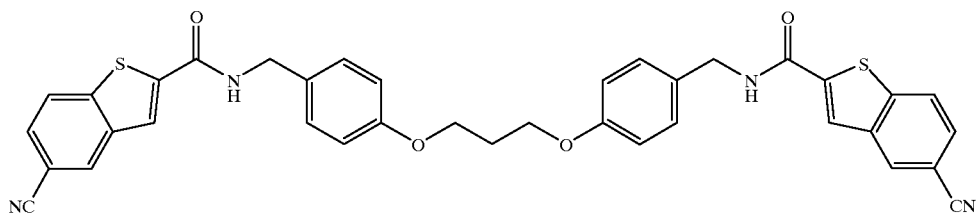

1,3-Bis-{4-[(5-cyano-2-benzthiophenyl-carboxamido)-methyl]-phenoxy}-propane

The noted compound was prepared according to the procedures above using the bis-benzylamine of Example 12 and the 5-cyano-2-benzthiophenoyl chloride of Example 115 to provide the diamide as a light yellow solid (57% yield).

$^1$H NMR (DMSO-d$_6$): δ9.43 (br s, 2H), 8.55 (s, 2H), 8.27 (d, 2H, J=8.5 Hz), 8.21 (s, 2H), 7.81 (d, 2H, J=8.5 Hz), 7.26 (d, 4H, J=8.5 Hz), 6.92 (d, 4H, J=8.5 Hz), 4.41 (s, 4H), 4.10 (t, 4H, J=6.0 Hz), 2.14 (m, 2H).

EXAMPLE 117

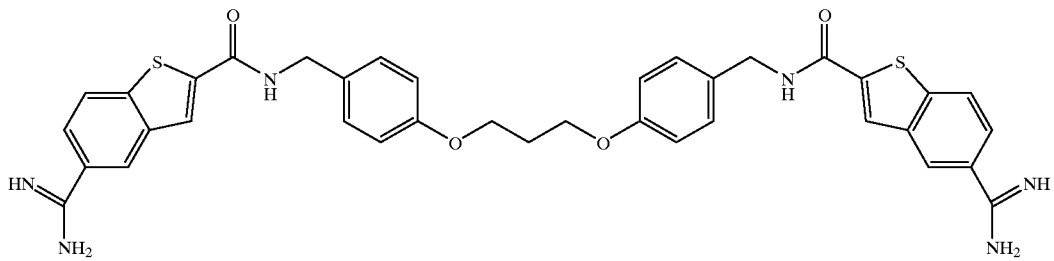

1,3-Bis-{4-[(5-carbamidoyl-2-benzthiophenyl-carbamido)-methyl]-phenoxy}-propane The bis-nitrile amide of Example 116 was subjected to room temperature Pinner reaction (See, e.g., A. Pinner, et al., *Ber.* 10, 1889 (1877); *Ber.* 11, 4, 1475 (1878); and *Ber.* 16, 352, 1643 (1883)) (MeOH/HCl, RT, overnight; EtOH/NH$_3$, RT, overnight) to provide the desired bis-amidine as a white solid after RP-HPLC purification (10% yield).

LRMS (electrospray) m/z: 346 (M/2+1).

$^1$H NMR (CD$_3$OD): δ8.39 (s, 2H), 8.18 (d, 2H, J=8.5 Hz), 8.12 (s, 2H), 7.80 (d, 2H, J=8.5 Hz), 7.30 (d, 4H, J=8.5 Hz), 6.92 (d, 4H, J=8.5 Hz), 4.52 (s, 4H), 4.15 (t, 4H, J=6.0 Hz), 2.21 (m, 2H).

Also encompassed by the present invention are those compounds of Formula (I) in which D is —NH—. The preparation of such compounds is described in the following reaction scheme in which Z is —(CH$_2$)$_m$ wherein m is 2:

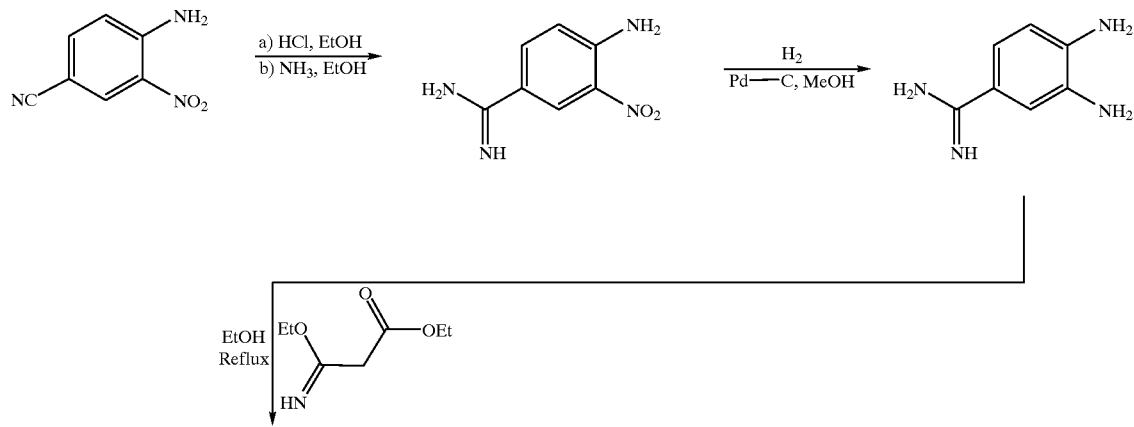

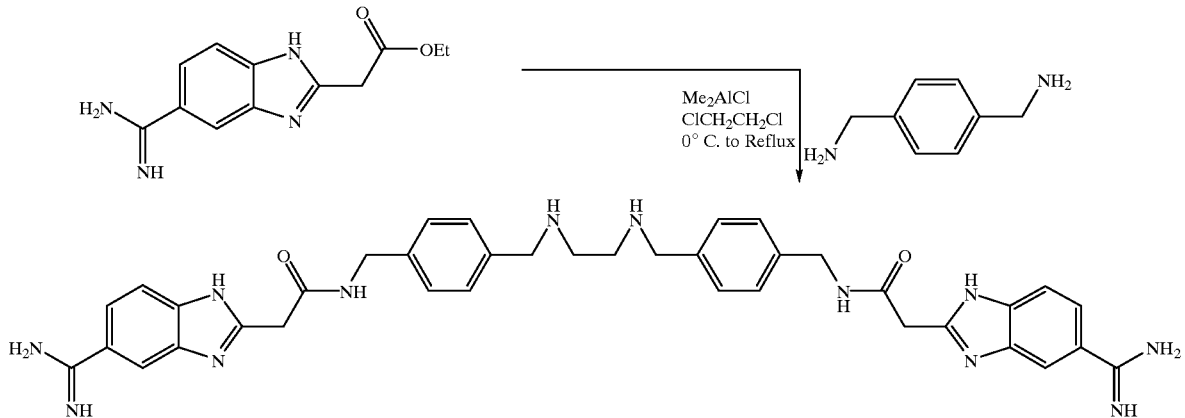

EXAMPLE 118

5-Carbamimidoyl-1H-benzimidazol-2-yl)-acetic acid ethyl ester

4-Amino-3-nitrobenzonitrile (30 g, 0.184 mol) was dissolved in anhydrous methanol (750 mL) and cooled in an ice-bath. Hydrogen chloride gas was bubbled into the solution for 15 min. and the reaction mixture was stirred overnight at room temperature. The solvent was evaporated in a rotary evaporator and the residue was dissolved in anhydrous ethanol (750 mL) and cooled in an ice-bath. Ammonia gas was bubbled into the solution for 15 min and the mixture was transferred to pressure tubes (three different tubes) and heated at 80° C. in an oil-bath overnight behind a blast shield. The reaction mixture was allowed to cool and was concentrated to half the volume and an equal volume of cold ether was added. The precipitate was removed by filtration, washed with ether and dried under vacuum to give crude 4-amino-3-nitro-benzamidine which was used in subsequent procedures without further purification.

$^1$H NMR (CD$_3$OD): δ8.46 (d, 1H, J=2.0 Hz), 7.58 (dd, 1H, J=8.8, 2.0 Hz), 7.08 (d, 1H, J=8.8 Hz).

The crude amino-nitro-benzamidine was dissolved in methanol (400 mL), treated with 10% palladium on carbon (1.2 g) and shaken under an atmosphere of hydrogen gas (50 psi) for 15 hours. The reaction mixture was filtered through a pad of celite and evaporated to give 3,4-diamino-benzamidine as a light brown solid (26 g, 94% yield). This material was used without further purification.

$^1$H NMR (CD$_3$OD): δ7.12 (dd, 1H, J=8.3, 2.2 Hz), 7.08 (d, 1H, J=2.2 Hz), 6.75 (d, 1H, J=8.3 Hz).

The crude benzamidine-diamine (5 g; 0.0203 mol) then was refluxed in absolute ethanol (300 mL) for 20 min. The imidate of Example 102 (12 g; 0.061 mol) was then added and the reaction mixture was refluxed for an additional six hours. The mixture was evaporated to dryness and the residue was treated with 1N HCl until the solution was acidic (pH~5). The aqueous layer was extracted with dichloromethane (3×100 mL) to remove diethyl malonate. The aqueous layer was neutralized with 30% ammonium hydroxide (ice-bath temperature) and evaporated to dryness. The residue was treated with a 3:1 mixture of ethanol:dichloromethane (500 mL), dried over anhydrous sodium sulfate, filtered and evaporated to give an amber oil which solidified under vacuum to give the desired ester as a tan color powder (7.6 g: 94% yield).

$^1$H NMR (CD$_3$OD): δ8.08 (s, 1H), 7.84 (d, 1H, J=8.5 Hz), 7.78 (d, 1H, J =8.5 Hz), 4.22 (q, 2H, J=7.1 Hz), 1.27 (t, 3H, J=7.1 Hz).

EXAMPLE 119

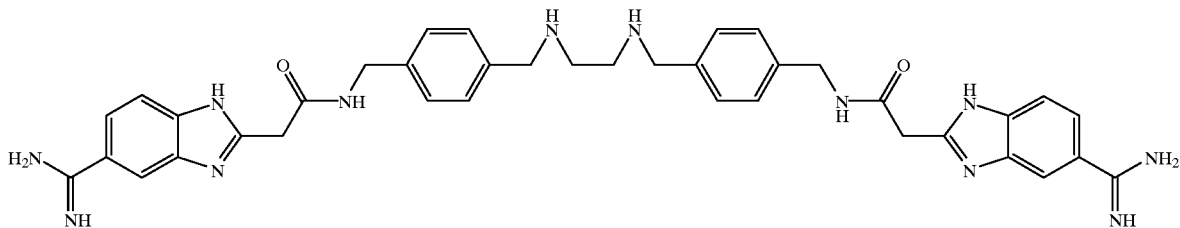

2-(5-Carbamimidoyl-1H-benzimidazol-2-yl)-N-(4-{[2-(5-carbamimidoyl-1H-benzimidazol-2-yl)-acetylamino]-methyl}-benzylamino)-ethylamino]-methyl}-benzyl)-acetamide A solution of dimethylaluminum chloride (7.5 mL, 1.0 M in hexanes) was added to a cooled suspension of p-xylylenediamine (1.020 g, 7.5 mmol) in 20 mL of anhydrous 1,2-dichloroethane under argon. The mixture was stirred at room temperature for two and a half hours. The benzimidazole amidine ester of Example 118, (615 mg, 2.5 mmol) was added in portions followed by the addition of 50 mL of anhydrous 1,2-dichloroethane. The mixture was refluxed under argon for 41 hours. The reaction mixture was cooled and made basic by the addition dropwise of aqueous ammonia. The mixture was filtered, washed with chloroform and then with ethanol. The ethanol fraction was evaporated to dryness and purified by RP-HPLC to give 11 mg (1% yield) of the noted compound as a tan white solid.

LRMS: m/z 350.2 (M/2+1).

$^1$H NMR (DMSO-d$_6$): δ9.96 (br s, 1H), 9.53 (s, 2H), 9.26 (s, 2H), 9.18 (s, 1H), 8.26 (s, 1H), 7.90 (d, 1H, J=9.0 Hz), 7.84 (d, 1H, J=9.0 Hz), 7.56 (d, 2H, J=8.0 Hz), 7.38 (d, 2H, J=8.0 Hz), 4.38 (d, 2H, J=5.5 Hz), 4.21 (s, 2H), 4.17 (m, 2H), 3.39 (br s, 2H).

Assay Procedures—K$_i$ Determinations of Proteases

Protease inhibition was assayed according to published procedures with minor modifications using various proteases and specific chromogenic peptide p-nitroanilide substrates. Assays were performed in Costar ultra-low cluster 96-well microtiter plate (Costar Corning Corp., Cambridge Mass.). Each protease was incubated with various concentrations of the test compound for 15 min. at 37° C. or as otherwise indicated, in specific assay buffer, and the residual activity was then measured by addition of the substrate. p-Nitroaniline produced by the proteolysis was determined by measuring the change in absorbance at 405 nm on a SpectraMAX 340 plate reader (Molecular devices, Sunnyvale, Calif.).

K$_i$ Determinations

1. The inhibition constant, K$_i$ is calculated from individual data points using the equation for a tight-binding inhibitor (See Beith, "Proteinase Inhibitors-Proceedings of 2nd Int. Res. Conference", Fritz, et al. eds, New York, p.4463–4469 (1974)):

$$v_i/v_o[((K_i'+[I]+[E]_o)^2-4\,[I]_o[E]_o)^{1/2}(K_i'+[I]_o-[E]_o)]/2[E]_o$$

where K$_i$' is apparent inhibition constant; v$_i$ and v$_o$ are the inhibited and uninhibited rates, respectively; [I]$_o$ and [E]$_o$ are the total concentrations of inhibitor and enzyme, respectively.

[note: [E]$_o$ is determined by active site titration of enzyme]

The K$_i$ values are obtained by correcting K$_i$' values for the effect of substrate concentration according to:

$$K_i = \frac{K_i'}{1+\frac{[S]}{K_m}}$$

(See Beith, *Biochem. Med.* 32, 387–397 (1984))

2. Other inhibition data (K$_i$>>[E]$_o$), the K$_i$ is calculated from using the equations for a competitive inhibitor:

$$K_i = \frac{IC_{50}}{1+\frac{[S]}{K_m}}$$

(See Segel, I. H. (1993) in "Enzyme Kinetics", Wiley Interscience, New York, pp. 106–107)

IC$_{50}$ is determined by fitting the individual inhibition data point to Sigmoid or four-parameter curve-fit equations.

A. Human Luna Tryptase

Human lung tryptase purchased from Cortex Biochem (San Leandro, Calif.) was purified further on a Superdex 200 gel-filtration column. The active-site concentration of the enzyme was determined by spectrophotometric titration with 4-nitrophenyl 4'-guanidinobenzoate according to Schwartz, et al., *J. Immunol.*, 114, 2304–2311 (1990).

Tryptase activity was measured according to the procedures of Schwartz, et al., *J. Biol. Chem.*, 261, 7372–7379 (1986) (See also, Schwartz, L. B., *Methods In Enzymology,* 244, 88 (1994)) with minor modifications, using Tosyl-Gly-Pro-Arg-p-nitroanilide ("GPR-pNA", Sigma Chemical Co., St. Louis, Mo., T-1637) as a chromogenic substrate. The reaction was performed in 50 mM Tris-HCl, pH 8.0, containing 150 mM NaCl and 0.02% Triton X-100 at 37° C. in Costar ultra-low cluster 96-well microtiter plates (Costar Corning Corp., Cambridge, Mass.). The amount of pNA produced by tryptase was determined by measuring the change in absorbance at 405 nm on a SpectraMAX 340 plate reader (Molecular devices, Sunnyvale, Calif.). The K$_m$ for the substrate was determined by Lineweaver-Burk analysis from initial velocities of substrate hydrolysis. The inhibition assay was carried out in a total volume of 200 μL. Tryptase (30 μL-final concentration 1 nM) was incubated with various concentrations of sample compound (50 μL) to be tested in the above assay buffer for 5 min. The reaction was started by the addition of substrate GPR-pNA (40 μL-final concentration 320 μM), and the residual activity was measured after 15 min. of incubation. The inhibition constant, K$_i$, was determined by fitting the inhibition data to a two-site competitive binding equation using data analysis program GraphPad PRISM (GraphPad Software, Inc., San Diego, Calif.).

B. Human Neutrophil Elastase

Human Neutrophil elastase activity was determined by using pyroGlu-Pro-Val-pNA in 100 mM Tris-HCl, pH 8.3, 0.96 M NaCl, 1% BSA (See Kramps, et al. *Scand. J. Clin. Lab. Invest.* 43, 427–432 (1983)).

C. Bovine pancreatic Trysin

Bovine pancreatic Trypsin (TPCK-treated) activity was determined by using N-a-Benzoyl-L-Arg-pNA in 50 mM Tris-HCl, pH 8.2, 20 mM CaCl$_2$ (See Somorin, et al., *J. Biochem.* 85, 157–162 (1979)).

D. Bovine Pancreatic Chymotrypsin

Bovine Pancreatic Chymotrypsin activity was determined by using N-Suc-Ala-Ala-Pro-Phe-pNA in 100 mM Tris-HCl, pH 7.8, 10 mM CaCl$_2$ (See Delmar, et al., *J. Biochem.* 85, 157–162 (1979)).

E. Human Neutrophil Cathepsin G

Human Neutrophil Cathepsin G activity was determined by using N-Suc-Ala-Ala-Pro-Phe-pNA in 625 mM Tris-HCl, pH 7.5, 2.5 mM MgCl$_2$, 0.125% Brij 35 (See Groutas et al., *Arch. Biochem. Biophys.* 294, 144–146 (1992)).

F. Human Plasma Plasmin

Human plasma plasmin activity was determined by using Tosyl-Gly-Pro-Lys-pNA in 100 mM Tris-HCl, pH 7.4, 100 mM NaCl, 0.05% Triton X-100 (See Lottenberg, et al., *Meth. Enzymol.* 80, 341–361 (1981)).

G. Human Plasma Factor Xa

Human plasma factor Xa activity was determined by using N-Benzoyl-Ile-Glu-Gly-Arg-pNA in 50 mM Tris-HCl, pH 7.8, 200 mM NaCl, 0.05% BSA (See Lottenberg, et al. *Meth. Enzymol.* 80, 341–361 (1981)).

H. Human Plasma Thrombin

Human plasma thrombin activity was determined by using H-D-Phe-Pip-Arg-pNA in 50 mM Tris-HCl, pH 8.3, 100 mM NaCl, 1% BSA (See Lottenberg, et al. *Meth. Enzymol.* 80, 341–361 (1981)).

I. Human Plasma and r-Tissue Kallikrein

Human plasma and r-tissue kallikrein activity were determined in 50 mM Tris-HCl, pH 7.8, 200 mM NaCl, 0.05% BSA by using H-D-Prolyl-Phe-Arg-pNA and DL-Val-Leu-Arg-pNA, respectively (See Lottenberg, et al., *Meth. Enzymol.* 80, 341–361 (1981)).

The inhibition constant (K$_i$) of the test compounds against each proteolytic enzyme was determined according to Zitnik et al., *Biochem. Biophys. Res. Commun.* 232, 687–697 (1997)). The results are provided in Table I.

In order to evaluate antigen-induced airway hyperresponsiveness in guinea pigs, a baseline histamine bronchoprovo-

TABLE I

Experimentally Determined $K_i$ (in $\mu$M)

| Ex. No. | Tryptase | Trypsin | Thrombin | Factor Xa | Tissue Kallikrein | Plasma Kallikrein | Plasmin | Elastase | Cathepsin G | Chymotrypsin |
|---|---|---|---|---|---|---|---|---|---|---|
| 46 | 1.5 | N.D.* | N.D. | N.D. | N.D. | N.D. | N.D. | N.D. | N.D. | N.D. |
| 44 | 3.2 | 8.0 | N.D. | N.D. | N.D. | N.D. | N.D. | N.D. | N.D. | N.D. |
| 42 | 0.25 | N.D. | >100 | 47.0 | N.D. | N.D. | >100 | >100 | >100 | N.D. |
| 48 | 12.5 | 4.2 | N.D. | N.D. | N.D. | N.D. | N.D. | N.D. | N.D. | N.D. |
| 50 | 0.80 | N.D. | >100 | >100 | >100 | >100 | 6.1 | >100 | >100 | 6.3 |
| 52 | 1.5 |  | N.D. | N.D. | N.D. | N.D. | N.D. | N.D. | N.D. | N.D. |
| 58 | 0.001 | 1.5 | >100 | 20.0 | >100 | 46.0 | 3.8 | >100 | >100 | >100 |
| 56 | <0.00001 | 1.3 | >100 | N.D. | >100 | N.D. | 1.6 | >100 | >100 | >100 |
| 54 | <0.00001 | 0.91 | >100 | >100 | >100 | 16.0 | 4.1 | >100 | >100 | >100 |
| 60 | 0.0002 | 1.5 | >100 | 17.7 | >100 | 6.3 | 12.0 | >100 | >100 | >100 |
| 62 | 0.0005 | 2.4 | >100 | 35.0 | >100 | 2.9 | 11.6 | >100 | >100 | >100 |
| 64 | 0.05 | 1.4 | >100 | 35.3 | >100 | 7.3 | 6.5 | >100 | >100 | >100 |
| 66 | 0.38 | 0.51 | >100 | 25.7 | >100 | 0.70 | 10.1 | >100 | >100 | >100 |
| 45 | 0.80 | 12.0 | >100 | 7.6 | >100 | 34.0 | 10.0 | >100 | >100 | >100 |
| 43 | 0.11 | 3.6 | >100 | 15.6 | >100 | >100 | 2.6 | >100 | >100 | 20.0 |
| 41 | 0.08 | 2.5 | >100 | 6.4 | >100 | 18.0 | 0.93 | >100 | >100 | >100 |
| 47 | 0.03 | 1.8 | >100 | 2.9 | >100 | 2.5 | 0.06 | >100 | >100 | >100 |
| 49 | 0.02 | 2.8 | >100 | 7.4 | >100 | 6.0 | 0.74 | >100 | >100 | >100 |
| 51 | 0.03 | 5.2 | >100 | 6.1 | >100 | 12.0 | 2.0 | >100 | >100 | >100 |
| 53 | 0.10 | 3.0 | >100 | 16.0 | >100 | 8.8 | 10.0 | >100 | >100 | >100 |
| 59 | 0.08 | 1.1 | >100 | 8.3 | >100 | 72.0 | 8.7 | >100 | >100 | >100 |
| 57 | 0.01 | 1.7 | >100 | N.D. | >100 | N.D. | 10.7 | >100 | >100 | >100 |
| 55 | 0.01 | 0.9 | >100 | 1.8 | >100 | 11.0 | 7.6 | >100 | >100 | >100 |
| 61 | 0.01 | 1.2 | >100 | 1.0 | >100 | 7.7 | 6.0 | >100 | >100 | >100 |
| 63 | 0.02 | 2.4 | >100 | N.D. | >100 | N.D. | 28.0 | >100 | >100 | >100 |
| 65 | 0.35 | 2.2 | >100 | 2.6 | >100 | 24.0 | 46.0 | >100 | >100 | >100 |
| 68 | 0.02 | 3.2 | >100 | 20.0 | >100 | 4.3 | 10.0 | >100 | >100 | >100 |
| 74 | 0.44 | 1.4 | >100 | 40.0 | 16.0 | 9.0 | 3.7 | >100 | >100 | >100 |
| 75 | 0.05 | 3.0 | >100 | 6.0 | >100 | 2.9 | >100 | >100 | >100 | >100 |
| 76 | 0.005 | 0.83 | 21.0 | >100 | 5.0 | 2.8 | >100 | >100 | >100 | >100 |
| 77 | 0.01 | 1.4 | >100 | 1.9 | 32.0 | 2.9 | 4.3 | >100 | >100 | >100 |
| 85 | 0.003 | 1.1 | >100 | 2.2 | >100 | 1.7 | 5.2 | >100 | >100 | >100 |
| 86 | 0.003 | 2.1 | >100 | 10.0 | >100 | 1.4 | 0.34 | >100 | >100 | >100 |
| 87 | 0.002 | 2.8 | >100 | 19.0 | >100 | 3.5 | 7.6 | >100 | >100 | >100 |
| 88 | N.D. | N.D. | N.D. | N.D. | N.D. | N.D. | N.D. | N.D. | N.D. | N.D. |
| 93 | 0.001 | 1.5 | >100 | 15.0 | 14.0 | 3.9 | 6.7 | >100 | >100 | >100 |
| 100 | 0.0002 | 0.15 | >100 | >100 | >100 | >100 | 0.74 | >100 | >100 | 18.0 |
| 108 | 0.009 | 3.6 | >100 | 19.0 | >100 | 4.3 | 1.4 | >100 | >100 | >100 |
| 109 | 0.008 | 11.4 | >100 | 40.0 | >100 | 2.5 | 0.11 | >100 | >100 | 14.7 |
| 107 | 0.012 | 4.8 | >100 | 27.0 | >100 | 12.0 | 2.1 | >100 | >100 | 26.0 |
| 110 | 1.2 | N.D. | N.D. | N.D. | N.D. | N.D. | N.D. | N.D. | N.D. | N.D. |
| 111 | 1.1 | N.D. | N.D. | N.D. | N.D. | N.D. | N.D. | N.D. | N.D. | N.D. |
| 117 | 0.012 | 13.0 | >100 | 59.0 | >100 | >100 | 50.0 | >100 | >100 | 40.0 |
| 119 | 0.002 | N.D. | N.D. | N.D. | N.D. | N.D. | N.D. | N.D. | N.D. | N.D. |

*N.D. = not determined

As noted the compounds of the invention are useful in the treatment of inflammatory disease states, particularly those which are mediated by mast cell degranulation and activation. A particularly preferred embodiment of the invention relates to the treatment of disorders of the pulmonary system, for example, allergic rhinitis, chronic obstructive pulmonary disease, emphysema and most preferably, asthma. The compounds of the invention were tested for their ability to inhibit hyperresponsiveness in a guinea pig airway hyperresponsiveness screen according to the following protocol:

Male Hartley guinea pigs (Charles River Laboratories Inc., Wilmington, Mass.) were sensitized to ovalbumin by intraperitoneal injection with a 0.5 mL solution of 10 $\mu$g ovalbumin and 10 mg aluminum hydroxide in phosphate-buffered saline. Booster injections were administered on weeks three and five to ensure high titers of IgE and IgG1 (Andersson, P., *Int. Arch. Allergy Appl. Immunol.* 64, 249–258 (1981)). Seven to nine weeks after the initial injection, the animals were used to evaluate antigen-induced guinea pig airway responses.

cation was initially conducted in unrestrained animals. Guinea pigs (450–600 g) were placed in a whole body plethysmograph (Buxco Electronics, Troy, N.Y.). The animals were exposed to 5 second bursts of histamine aerosol generated by a DeVilbis ultrasonic nebulizer (Somerset, Pa.). The peak bronchoconstrictor response, expressed as Pause$_{enhanced}$ (Chand, N., et al., *Allergy* 48, 230–235 (1993)) in response to rising histamine concentrations of 0, 25, 50, 100, and 200 mg/ml in phosphate-buffered saline (PBS) (GIBCO, Grand Island, N.Y.) administered at ten minute intervals was determined. Three days after the histamine baseline determination, the guinea pigs were again placed in the whole body plethysmograph and challenged with a 3 second aerosolized burst of 0.1% ovalbumin in phosphate-buffered saline. Six hours after antigen exposure, the development of hyperresponsiveness was evaluated by repeating the histamine bronchoprovocation. Comparisons between treatment groups were based on areas under the histamine dose response curves (AUC).

Test compounds were administered by intratracheal instillation at a dose of 1 mg/kg in PBS (pH 7.2), 1 hour before the antigen challenge. After anesthetizing a guinea pig with inhaled methoxyflurane, an endotracheal tube (18 gauge Teflon® sheath) was visually passed into the trachea with the aid of a fiberoptic light source. Test agents (or PBS for control animals) was dosed through the tube followed by a bolus of air to facilitate dispersion.

Two-way analysis of variance (ANOVA) followed by the Fisher PLSD test was used to evaluate areas under the curve ("AUC") for histamine dose responses in guinea pigs. Significance was accepted for p<0.05. The results are provided in Table II.

TABLE II

Guinea Pig Airway Hyperresponsiveness Inhibition

| Example No. | Dose (mg/kg, i.t.) | Hyperresponsiveness AUC % Inhibition | Significance vs. Antigen-stimulated control |
|---|---|---|---|
| 108 | 1 | 68 | p < 0.05 |
| 41 | 1 | 95 | p < 0.05 |
| 47 | 1 | 29 | not significant |
| 54 | 1 | 53 | p < 0.05 |
| 55 | 1 | 107 | p < 0.05 |
| 50 | 1 | 50 | p < 0.05 |
| 56 | 1 | 62 | p < 0.05 |

It is to be understood that the above description is intended only to be illustrative of the invention and not restrictive. As will be apparent to one skilled in the art upon reading the description, other embodiments may be prepared and tested using other methods, reagents and procedures familiar to the skilled artisan. The scope of the invention, therefore, should not be determined solely based upon the specific teaching of the description. Instead, the scope of the invention should be determined based upon the teachings of the description along with reference to the appended claims and the full scope of equivalents to which the claims are entitled based upon the knowledge of one of ordinary skill in the art.

We claim:

1. A compound of Formula (I):

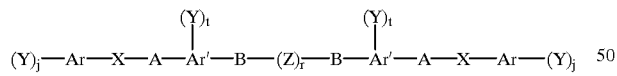

(I)

wherein at least one of Ar or Ar' is phenyl;

A is $-NR^2-(CH_2)_m-$;

B is $-[(D)-(CH_2)_m]$;

D is $-O-$, $-S-$, or $-SO_2-$;

X is $-SO_2-$;

Y is $R^1HN-C(=NH)-$, $R^1HN-CO-NH-$, or $R^1HN-(CH_2)_v-$, $CH_3SO_2NH-(CH_2)_v-$, $-OH$, $-SH$, $-CF_3$, $-F$, $-Cl$, $-Br$, $-I$, $-H$, $-O(C_1-C_4)$alkyl, aryl, $(C_1-C_4)$acyloxy, $(C_1-C_4)$alkyl, $(C_1-C_4)$alkylthio, $-NO_2$, wherein at least one Y is $R^1HN-C(=NH)-$, Z is $-(CH_2)_n-$, $-(CH_2)_v-C=C-(CH_2)_v-$, or

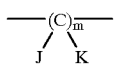

in which J and K, independently, are $-H$, $-(C_1-C_6)$alkyl, a $-(C_3-C_6)$carbocyclic ring wherein the $-(C_3-C_6)$ carbocyclic ring optionally is substituted with one or more $-O(C_1-C_4)$alkyl groups, or J and K, when taken together with the carbon to which they are attached, form a 3-membered to 8-membered carbocyclic ring;

$R^1$ is $-H$, $(C_1-C_4)$alkyl$-O-$ or $HO-$;

$R^2$ is $-H$ or $-(C_1-C_4)$alkyl;

j is an integer from 1 to 5, inclusive;

m is an integer between 0 and 10, inclusive;

n is an integer between 0 and 10, inclusive;

r is 1;

t is an integer from 1 to 5, inclusive;

v is an integer between 0 and 6, inclusive;

wherein which each Y, Ar, Ar', X, A, B, j, m, r, n, t or v is the same or different; or, a pharmaceutically acceptable salt, ester, or solvate thereof.

2. A compound as claimed in claim 1 wherein at least one $R^1$ is hydrogen.

3. A compound as claimed in claim 2 wherein at least one Ar is phenyl and is para- or meta- substituted.

4. A compound as claimed in claim 3 wherein at least one Ar is phenyl and is para- substituted.

5. A compound as claimed in claim 3 wherein at least one Ar is phenyl and is meta- substituted.

6. A compound as claimed in claim 2 wherein at least one Ar' is phenyl and is para- or meta- substituted.

7. A compound as claimed in claim 6, wherein at least one Ar' is phenyl and is para- substituted.

8. A compound as claimed in claim 6 wherein at least one Ar' is phenyl and is meta- substituted.

9. A compound as claimed in claim 1 wherein $R^2$ is hydrogen; and m is an integer between 2 and 7, inclusive.

10. A compound of Formula (I):

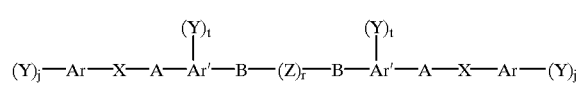

(I)

wherein

Ar or Ar' is aryl, or a 5-membered to 7-membered carbocyclic ring;

A is $-NR^2-(CH_2)_m$;

B is $-[(D)_{[r]}-(CH_2)_m]-$;

D is $-O-$, $-S-$, or $-SO_2-$;

X is $-SO_2-$;

Y is $R^1HN-C(=NH)-$, $R^1HN-CO-NH-$, or $R^1HN-(CH_2)_v-$, $CH_3SO_2NH-(CH_2)_v-$, $-OH$, $-SH$, $-CF_3$, $-F$, $-Cl$, $-Br$, $-I$, $-H$, $-O(C_1-C_4)$ alkyl, aryl, $(C_1-C_4)$acyloxy, $(C_1-C_4)$alkyl, $(C_1-C_4)$ alkylthio, $-NO_2$;

Z is —(CH$_2$)$_n$—, —(CH$_2$)$_v$—C=C—(CH$_2$)$_v$—, or

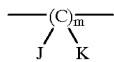

in which J and K, independently, are —H, —(C$_1$–C$_6$)alkyl, a —(C$_3$–C$_6$)carbocyclic ring wherein the —(C$_3$–C$_6$) carbocyclic ring optionally is substituted with one or more —O(C$_1$–C$_4$)alkyl groups, or J and K, when taken together with the carbon to which they are attached, form a 3-membered to 8-membered carbocyclic ring;

R$^1$ is —H, (C$_1$–C$_4$)alkyl—O— or HO—;
R$^2$ is —H or —(C$_1$–C$_4$)alkyl;
j is an integer from 1 to 14, inclusive;
m is an integer between 0 and 10, inclusive;
n is an integer between 1 and 10, inclusive;
r is 1;
t is an integer from 1 to 14, inclusive;
v is an integer between 0 and 6, inclusive;
wherein which each Y, Ar, Ar', X, A, B, j, m, r, n, t or v is the same or different;
or, a pharmaceutically acceptable salt, ester, or solvate thereof.

11. A compound as claimed in claim 10 wherein at least one of Ar or Ar' is phenyl.

12. A compound as claimed in claim 10 wherein R$^2$ is hydrogen.

13. A compound chosen from the group consisting of:

1,5-Bis-{4-[(3-carbamimidoyl-benzenesulfonylamino)-methyl]-phenoxy}-pentane;
1,5-Bis-{4-[(4-carbamimidoyl-benzenesulfonylamino)-methyl]-phenoxy}-pentane;
1,6-Bis-{4-[(3-carbamimidoyl-benzenesulfonylamino)-methyl]-phenoxy}-hexane;
1,6-Bis-{4-[(4-carbamimidoyl-benzenesulfonylamino)-methyl]-phenoxy}-hexane;
1,7-Bis-{4-[(3-carbamimidoyl-benzenesulfonylamino)-methyl]-phenoxy}-heptane;
1,7-Bis-{4-[(4-carbamimidoyl-benzenesulfonylamino)-methyl]-phenoxy}-heptane;
1,4-Bis-{4-[(3-carbamimidoyl-benzenesulfonylamino)-methyl]-phenoxy}-butane;
1,4-Bis-{4-[(4-carbamimidoyl-benzenesulfonylamino)-methyl]-phenoxy}-butane;
1,3-Bis-{4-[(3-carbamimidoyl-benzenesulfonylamino)-methyl]-phenoxy}-propane;
1,3-Bis-{4-[(4-carbamimidoyl-benzenesulfonylamino)-methyl]-phenoxy}-propane;
1,2-Bis-{4-[(3-carbamimidoyl-benzenesulfonylamino)-methyl]-phenoxy}-ethane;
1,2-Bis-{4-[(4-carbamimidoyl-benzenesulfonylamino)-methyl]-phenoxy}-ethane;
1,3-Bis-{4-[(3-carbamimidoyl-benzenesulfonylamino)-methyl]-phenoxy}-2-oxa-propane; and
1,3-Bis-{4-[(3-carbamimidoyl-benzenesulfonyl-[N-methyl]-amino)-methyl]-phenoxy}-propane.

14. A formulation which comprises a compound of Formula (1) in combination admixture, or associated with a pharmaceutically acceptable carrier, diluent or excipient therof:

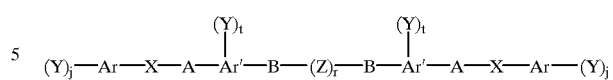

Ar or Ar' is aryl, or a 5-membered to 7-membered carbocyclic ring;
A is —NR$^2$—(CH$_2$)$_m$;
B is —[(D)$_{[r]}$—(CH$_2$)$_m$]—;
D is —O—, —S—, or —SO$_2$—;
X is —SO$_2$—;
Y is R$^1$HN—C(=NH)—, R$^1$HN—CO—NH—, or R$^1$HN—(CH$_2$)$_v$—, CH$_3$SO$_2$NH—(CH$_2$)$_v$—, —OH, —SH, —CF$_3$, —F, —Cl, —Br, —I, —H, —O(C$_1$–C$_4$) alkyl, aryl, (C$_1$–C$_4$)acyloxy, (C$_1$–C$_4$)alkyl, (C$_1$–C$_4$) alkylthio, —NO$_2$;
Z is —(CH$_2$)$_n$—, —(CH$_2$)$_v$—C=C—(CH$_2$)$_v$—, or

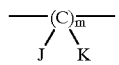

in which J and K, independently, are —H, —(C$_1$–C$_6$)alkyl, a —(C$_3$–C$_6$)carbocyclic ring wherein the —(C$_3$–C$_6$) carbocyclic ring optionally is substituted with one or more —O(C$_1$–C$_4$)alkyl groups, or J and K, when taken together with the carbon to which they are attached, form a 3-membered to 8-membered carbocyclic ring;

R$^1$ is —H, (C$_1$–C$_4$)alkyl—O— or HO—;
R$^2$ is —H or —(C$_1$–C$_4$)alkyl;
j is an integer from 1 to 14, inclusive;
m is an integer between 0 and 10, inclusive;
n is an integer between 1 and 10, inclusive;
r is 1;
t is an integer from 1 to 14, inclusive;
v is an integer between 0 and 6, inclusive;
wherein which each Y, Ar, Ar', X, A, B, j, m, r, n, t or v is the same or different;
or, a pharmaceutically acceptable salt, ester, or solvate thereof.

15. A formulation as claimed in claim 14 wherein at least one of Ar or Ar' is phenyl.

16. A formulation as claimed in claim 15 wherein at least one Y is R$^1$HN—C(=NH)—.

17. A formulation as claimed in claim 16 wherein at least one R$^1$ is hydrogen.

18. A formulation as claimed in claim 17 wherein at least one Ar is phenyl and is para- or meta- substituted.

19. A formulation as claimed in as claim 17 wherein at least one Ar' is phenyl and is para- or meta-substituted.

20. A formulation as claimed in claim 4 wherein R$^2$ is hydrogen.

21. A formulation as claimed in claim 20 wherein m is an integer between 2 and 7, inclusive.

22. A formulation which comprises a compound chosen from the group consisting of:

1,5-Bis-{4-[(3-carbamimidoyl-benzenesulfonylamino)-methyl]-phenoxy}-pentane;
1,5-Bis-{4-[(4-carbamimidoyl-benzenesulfonylamino)-methyl]-phenoxy}-pentane;
1,6-Bis-{4-[(3-carbamimidoyl-benzenesulfonylamino)-methyl]-phenoxy}-hexane;

1,6-Bis-{4-[(4-carbamimidoyl-benzenesulfonylamino)-methyl]-phenoxy}-hexane;

1,7-Bis-{4-[(3-carbamimidoyl-benzenesulfonylamino)-methyl]-phenoxy}-heptane;

1,7-Bis-{4-[(4-carbamimidoyl-benzenesulfonylamino)-methyl]-phenoxy}-heptane;

1,4-Bis-{4-[(3-carbaminidoyl-benzenesulfonylamino)-methyl]-phenoxy}-butane;

1,4-Bis-{4-[(4-carbamimidoyl-benzenesulfonylamino)-methyl]-phenoxy}-butane;

1,3-Bis-{4-[(3-carbamimidoyl-benzenesulfonylamino)-methyl]-phenoxy}-propane;

1,3-Bis-{4-[(4-carbamimidoyl-benzenesulfonylamino)-methyl]-phenoxy}-propane;

1,2-Bis-{4-[(3-carbamimidoyl-benzenesulfonylamino)-methyl]-phenoxy}-ethane;

1,2-Bis-{4-[(4-carbamimidoyl-benzenesulfonylamino)-methyl]-phenoxy}-ethane;

1,3-Bis-{4-[(3-carbamimidoyl-benzenesulfonylamino)-methyl]-phenoxy}-2-oxa-propane; and 1,3-Bis-{4-[(3-carbamimidoyl-benzenesulfonyl-[-methyl]-amino)-methyl]-phenoxy}-propane.

and a pharmaceutically acceptable carrier, diluent or excipient therefor.

23. A method for treating a warm blooded mammal having an inflammatory disorder which comprises administering to said mammal a compound of Formula (I):

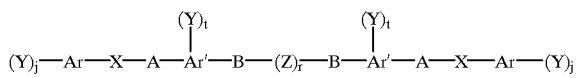

(I)

wherein

Ar or Ar' is aryl, or a 5-membered to 7-membered carbocyclic ring;

A is —NR² —(CH₂)ₘ;

B is —[(D)_{[r]}—(CH₂)ₘ]—;

D is —O—, —S—, or —SO₂—;

X is —SO₂—;

Y is R¹HN—C(=NH)—, R¹HN—CO—NH—, or R¹HN—(CH₂)ᵥ—, CH₃SO₂NH—(CH₂)ᵥ—, —OH, —SH, —CF₃, —F, —Cl, —Br, —I, —H, —O(C₁–C₄) alkyl, aryl, (C₁–C₄)acyloxy, (C₁–C₄)alkyl, (C₁–C₄) alkylthio, —NO₂;

Z is —(CH₂)ₙ—, —(CH₂)ᵥ—C=C—(CH₂)ᵥ—, or

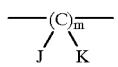

in which J and K, independently, are —H, —(C₁–C₆)alkyl, a —(C₃–C₆)carbocyclic ring wherein the —(C₃–C₆) carbocyclic ring optionally is substituted with one or more —O(C₁–C₄)alkyl groups, or J and K, when taken together with the carbon to which they are attached, form a 3-membered to 8-membered carbocyclic ring;

R¹ is —H; (C₁–C₄)alkyl—O— or HO—;

R² is —H or —(C₁–C₄)alkyl;

j is an integer from 1 to 14, inclusive;

m is an integer between 0 and 10, inclusive;

n is an integer between 1 and 10, inclusive;

r is 1;

t is an integer from 1 to 14, inclusive;

v is an integer between 0 and 6, inclusive;

wherein which each Y, Ar, Ar', X, A, B, j, m, r, n, t or v is the same or different;

or, a pharmaceutically acceptable salt, ester, or solvate thereof.

24. A method as claimed in claim 23 wherein at least one of Ar or Ar' is phenyl.

25. A method as claimed in claim 24 wherein at least one Y is R¹HN—C(=NH)—.

26. A method as claimed in claim 25 wherein at least one R¹ is hydrogen.

27. A method as claimed in claim 26 wherein at least one Ar is phenyl and is para- or meta- substituted.

28. A method as claimed in claim 26 wherein at least one Ar' is phenyl and is para- or meta- substituted.

29. A method as claimed in claim 23 wherein R² is hydrogen.

30. A method as claimed in claim 29 wherein m is an integer between 2 and 7, inclusive.

31. A method as claimed in claim 23 in which the mammal has a mast cell mediated disease.

32. A method for treating a warm blooded mammal having an inflammatory disorder which comprises administering to said mammal a compound which is chosen from the group consisting of:

1,5-Bis-{4-[(3-carbamimidoyl-benzenesulfonylamino)-methyl]-phenoxy}-pentane;

1,5-Bis-{4-[(4-carbamiimidoyl-benzenesulfonylamino)-methyl]-phenoxy}- pentane;

1,6-Bis-{4-[(3-carbamimidoyl-benzenesulfonylamino)-methyl]-phenoxy}-hexane;

1,6-Bis-{4-[(4-carbamimidoyl-benzenesulfonylamino)-methyl]-phenoxy}-hexane;

1,7-Bis-{4-[(3-carbamimidoyl-benzenesulfonylamino)-methyl]-phenoxy}-heptane;

1,7-Bis-{4-[(4-carbamimidoyl-benzenesulfonylamino)-methyl]-phenoxy}-heptane;

1,4-Bis-{4-[(3-carbamimidoyl-benzenesulfonylamino)-methyl]-phenoxy}-butane;

1,4-Bis-{4-[(4-carbamimidoyl-benzenesulfonylamino)-methyl]-phenoxy}-butane;

1,3-Bis-{4-[(3-carbainiidoyl-benzenesulfonylamino)-methyl]-phenoxy}-propane;

1,3-Bis-{4-[(4-carbamimidoyl-benzenesulfonylamino)-methyl]-phenoxy}-propane;

1,2-Bis-{4-[(3-carbamimidoyl-benzenesulfonylamino)-methyl]-phenoxy}-ethane;

1,2-Bis-{4-[(4-carbamimidoyl-benzenesulfonylamino)-methyl]-phenoxy}-ethane;

1,3-Bis-{4-[(3-carbamimidoyl- benzenesulfonylamino)-methyl]-phenoxy}-2-oxa-propane; and 1,3-Bis-{4-[(3-carbamimidoyl-benzenesulfonyl-[N-methyl]-amino)-methyl]-phenoxy}-propane.

33. A method as claimed in claim 32 in which the mammal has a mast cell mediated disease.

34. A method as claimed in claim 33 in which the disease involves tryptase activation.

35. A method as claimed in claim 33 in which the disease is asthma, allergic rhinitis, rheumatoid arthritis, dermatological diseases, multiple sclerosis, conjunctivitis, inflammatory bowel disease, anaphylaxis, osteoarthritis, peptic ulcers, or cardiovascular disease.

36. A method for preventing an inflammatory response in a warm blooded mammal which comprises administering to said mammal a compound of Formula (I):

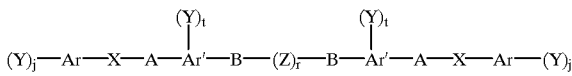
(I)

wherein
Ar or Ar' is aiyl, or a 5-membered to 7-membered carbocyclic ring;
A is —$NR^2$—$(CH_2)_m$;
B is —$[(D)_{[r]}$—$(CH_2)_m]$—;
D is —O—, —S—, or —$SO_2$—;
X is —$SO_2$—;
Y is $R^1HN$—C(=NH)—, $R^1HN$—CO—NH—, or $R^1HN$—$(CH_2)_v$—, $CH_3SO_2NH$—$(CH_2)_v$—, —OH, —SH, —$CF_3$, —F, —Cl, —Br, —I, —H, —$O(C_1$-$C_4)$alkyl, aryl, $(C_1$-$C_4)$acyloxy, $(C_1$-$C_4)$alkyl, $(C_1$-$C_4)$alkylthio, —$NO_2$;
Z is —$(CH_2)_n$—, —$(CH_2)_v$—C=C—$(CH_2)_v$—, or

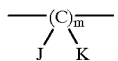

in which J and K, independently, are —H, —$(C_1$-$C_6)$alkyl, a —$(C_3$-$C_6)$carbocyclic ring wherein the —$(C_3$-$C_6)$ carbocyclic ring optionally is substituted with one or more —$O(C_1$-$C_4)$alkyl groups, or J and K, when taken together with the carbon to which they are attached, form a 3-membered to 8-membered carbocyclic ring;
$R^1$ is —H, $(C_1$-$C_4)$alkyl—O— or HO—;
$R^2$ is —H or —$(C_1$-$C_4)$alkyl;
j is an integer from 1 to 14, inclusive;
m is an integer between 0 and 10, inclusive;
n is an integer between 1 and 10, inclusive;
r is 1;
t is an integer from 1 to 14, inclusive;
v is an integer between 0 and 6, inclusive;
wherein which each Y, Ar, Ar', X, A, B, j, m, r, n, t or v is the same or different; or, a pharmaceutically acceptable salt, ester, or solvate thereof.

37. A method as claimed in claim 36 wherein at least one Ar or Ar' is phenyl.

38. A method as claimed in claim 37 wherein at least one Y is $R^1HN$—C(=NH)—.

39. A method as claimed in claim 38 wherein at least one $R^1$ is hydrogen.

40. A method as claimed in claim 39 wherein at least one Ar is phenyl and is para- or meta- substituted.

41. A method as claimed in claim 39 wherein at least one Ar' is phenyl and is para- or meta- substituted.

42. A method as claimed in claim 36 wherein $R^2$ is hydrogen.

43. A method as claimed in claim 42 wherein m is an integer between 2 and 7, inclusive.

44. A method as claimed in claim 36 in which the mammal has a mast cell mediated disease.

45. A method as claimed in claim 44 in which the disease involves tryptase activation.

46. A method as claimed in claim 45 in which the disease is asthma, allergic rhinitis, rheumatoid arthritis, dermatological diseases, multiple sclerosis, conjunctivitis, inflammatory bowel disease, anaphylaxis, osteoarthritis, peptic ulcers, or cardiovascular disease.

47. A method for preventing an inflammatory response in a warm blooded mammal which comprises administering to said mammal a compound which is chosen from the group consisting of:

1,5-Bis-{4-[(3-carbamimidoyl-benzenesulfonylamino)-methyl]-phenoxy}-pentanel
1,5-Bis-{4-[(4-carbamimidoyl-benzenesulfonylamino)-methyl]-phenoxy}-pentanei
1,6-Bis-{4-[(3-carbamimidoyl-benzenesulfonylamino)-methyl]-phenoxy}-hexane;
1,6-Bis-{4-[(4-carbarimidoyl-benzenesulfonylamino)-methyl]-phenoxy}-hexanei
1,7-Bis-{4-[(3-carbamimidoyl-benzenesulfonylamino)-methyl]-phenoxy}-heptane;
1,7-Bis-{4-[(4-carbamimidoyl-benzenesulfonylamino)-methyl]-phenoxy}-heptane;
1,4-Bis-{4-[(3-carbamimidoyl-benzenesulfonylamino)-methyl]-phenoxy}-butanei
1,4-Bis-{4-[(4-carbamimidoyl-benzenesulfonylamino)-methyl]-phenoxy}-butane;
1,3-Bis-{4-[(3-carbamimidoyl-benzenesulfonylamino)-methyl]-phenoxy}-propane;
1,3-Bis-{4-[(4-carbamimidoyl-benzenesulfonylamino)-methyl]-phenoxy}-propane;
1,2-Bis-{4-[(3-carbamimidoyl-benzenesulfonylamino)-methyl]-phenoxy}-ethane;
1,2-Bis-{4-[(4-carbamimidoyl-benzenesulfonylamino)-methyl]-phenoxy}-ethane;
1,3-Bis-{4-[(3-carbamimidoyl-benzenesulfonylamino)-methyl]-phenoxy}-2-oxa-propane; and
1,3-Bis-{4-[(3-carbamimidoyl-benzenesulfonyl-[N-methyl]-amino)-methyl]-phenoxy}-propane.

* * * * *